(12) United States Patent
Zukiwski et al.

(10) Patent No.: US 12,181,485 B2
(45) Date of Patent: Dec. 31, 2024

(54) METHODS OF BLOOD SCREENING

(71) Applicant: CASI Pharmaceuticals, Inc., Rockville, MD (US)

(72) Inventors: Alexander Anthony Zukiwski, Rockville, MD (US); Connie Westhoff, New York, NY (US)

(73) Assignee: CASI Pharmaceuticals, Inc, Rockville, MD (US)

( * ) Notice: Subject to any disclaimer, the term of this patent is extended or adjusted under 35 U.S.C. 154(b) by 346 days.

(21) Appl. No.: 17/471,620

(22) Filed: Sep. 10, 2021

(65) Prior Publication Data

US 2022/0137074 A1 May 5, 2022

Related U.S. Application Data

(60) Provisional application No. 63/076,489, filed on Sep. 10, 2020.

(30) Foreign Application Priority Data

Dec. 22, 2020 (EP) .................................... 20216639

(51) Int. Cl.
*G01N 33/80* (2006.01)
*A61K 39/00* (2006.01)
*C07K 16/28* (2006.01)

(52) U.S. Cl.
CPC ......... *G01N 33/80* (2013.01); *C07K 16/2896* (2013.01); *A61K 2039/505* (2013.01); *C07K 2317/33* (2013.01); *C07K 2317/565* (2013.01); *C07K 2317/92* (2013.01); *G01N 2500/10* (2013.01); *G01N 2800/24* (2013.01)

(58) Field of Classification Search
CPC ............... G01N 33/80; G01N 2500/10; G01N 2800/24; C07K 16/2896; C07K 2317/33; C07K 2317/565; A61K 2039/505
See application file for complete search history.

(56) References Cited

U.S. PATENT DOCUMENTS

| 11,236,173 B2 | 2/2022 | Goubier |
| 2020/0190209 A1 | 6/2020 | Merchiers |
| 2020/0362049 A1 | 11/2020 | Goubier |
| 2021/0277138 A1 | 9/2021 | Merchiers |

FOREIGN PATENT DOCUMENTS

WO 2019030581 A1 2/2019

OTHER PUBLICATIONS

Malhotra (Immunohematology 2020 36:93-98). (Year: 2020).*
Raos et al., "P-498: Challenges of blood compatibility testing and blood transfusion in patients treated with anti-CD38 monoclonal antibody", Vox Sanguinis, 2020, 115 (suppl. s1), 3-387 Abstracts.
Rosner et al., "VS-4-2: First experiences with DaraEx in crossmatching red blood cell concentrates under Daratumumab therapy", Transfus Med Hemother, 2018, 445 (suppl. 1), 1-90 Abstracts.

* cited by examiner

*Primary Examiner* — Changhwa J Cheu
(74) *Attorney, Agent, or Firm* — Riverside Law LLP

(57) ABSTRACT

The present invention relates to methods of identifying suitable donor blood for cancer patients receiving anti-CD38 antibodies as treatment. In particular, the present invention addresses problems associated with crossmatching patient and donor blood when the patient blood comprises anti-CD38 antibodies that interfere with crossmatching methods of the art.

26 Claims, 10 Drawing Sheets
Specification includes a Sequence Listing.

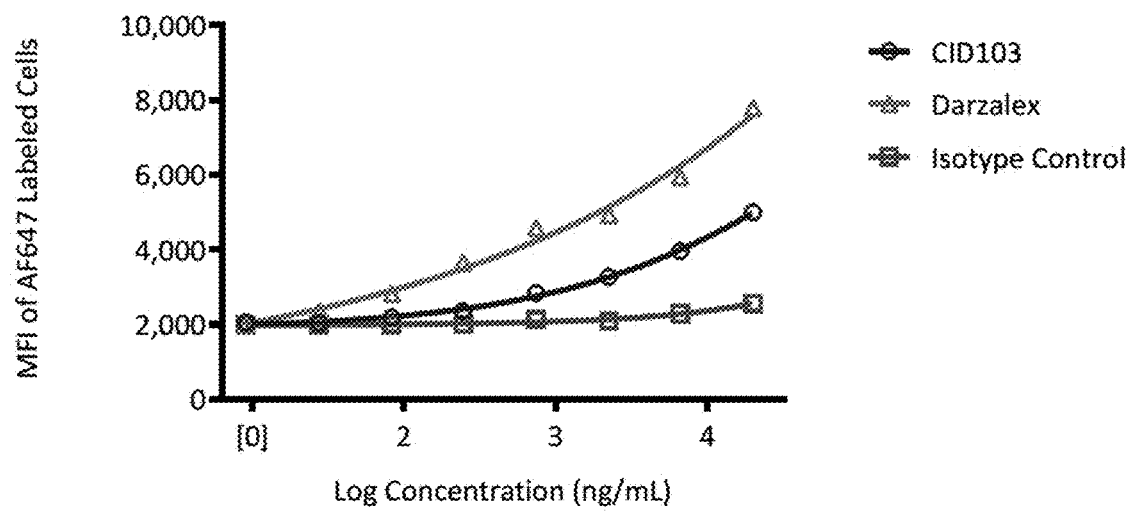
Fig. 4A  CASI02: RBC Binding Donor 1
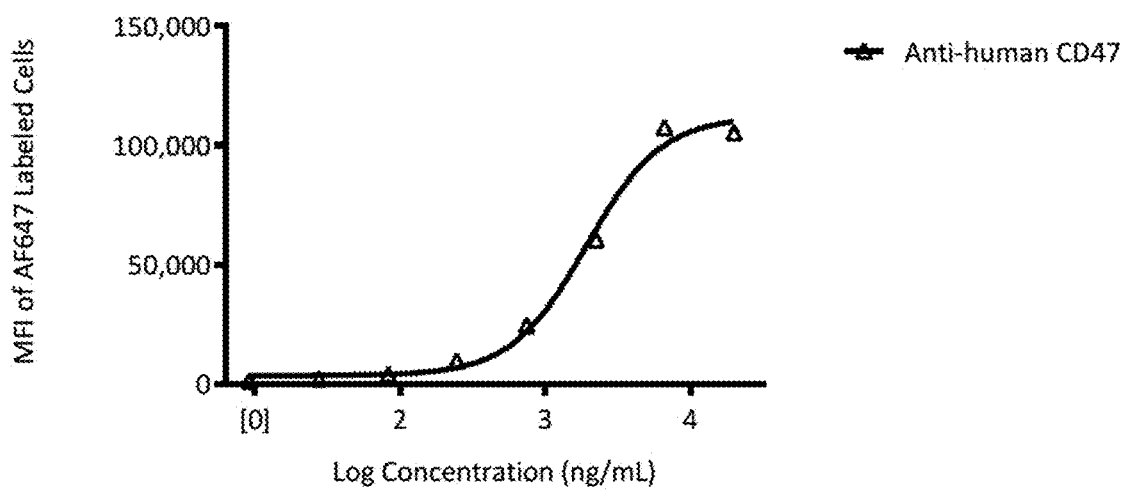
Fig. 4B  CASI02: RBC Binding Donor 1

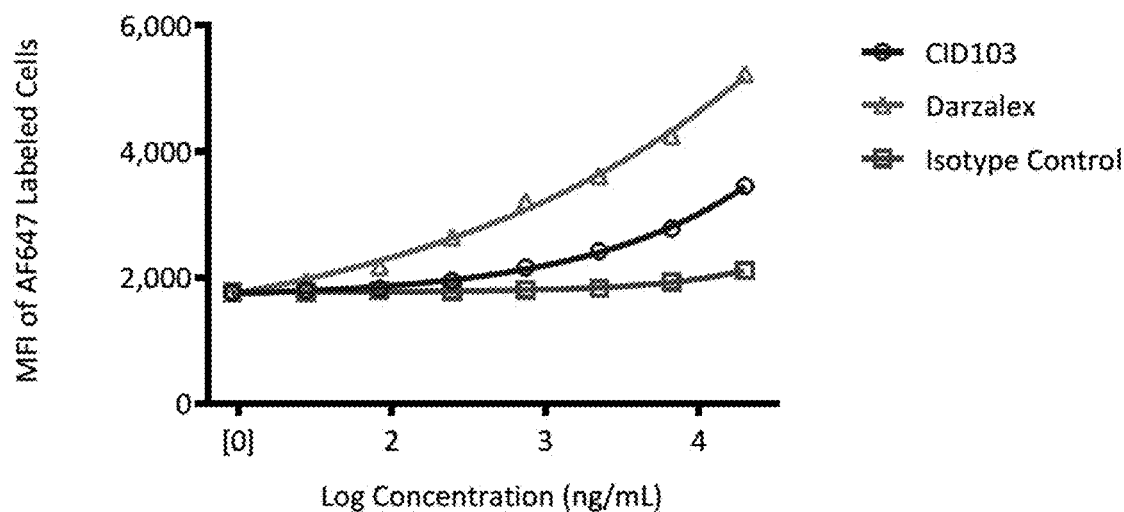
Fig. 5A  CASI02: RBC Binding Donor 2
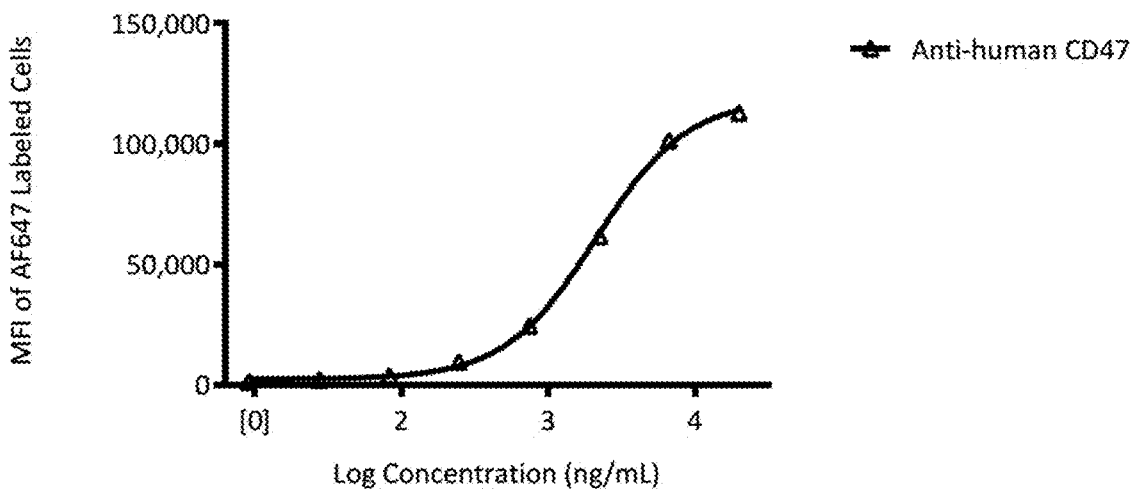
Fig. 5B  CASI02: RBC Binding Donor 2

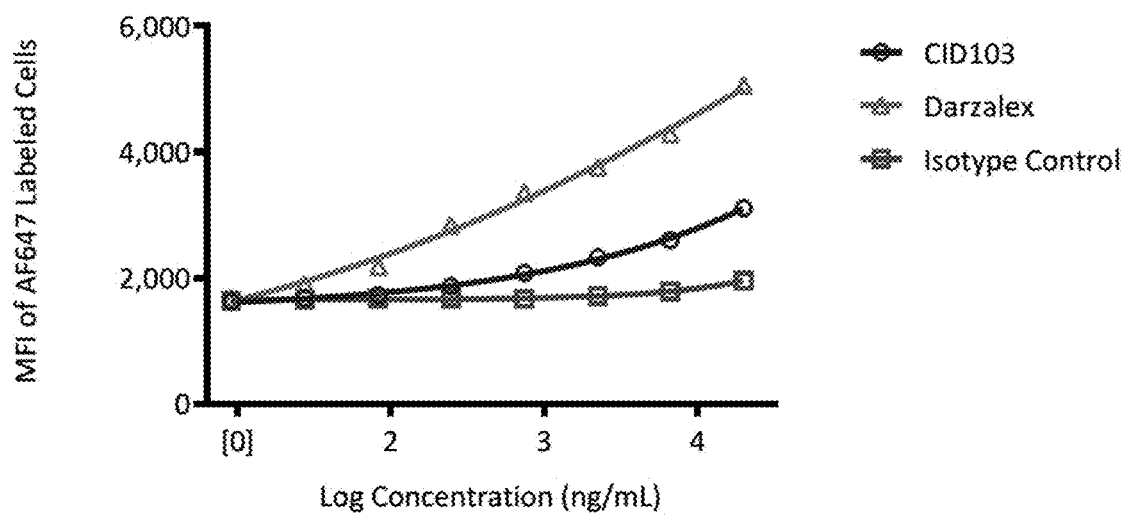
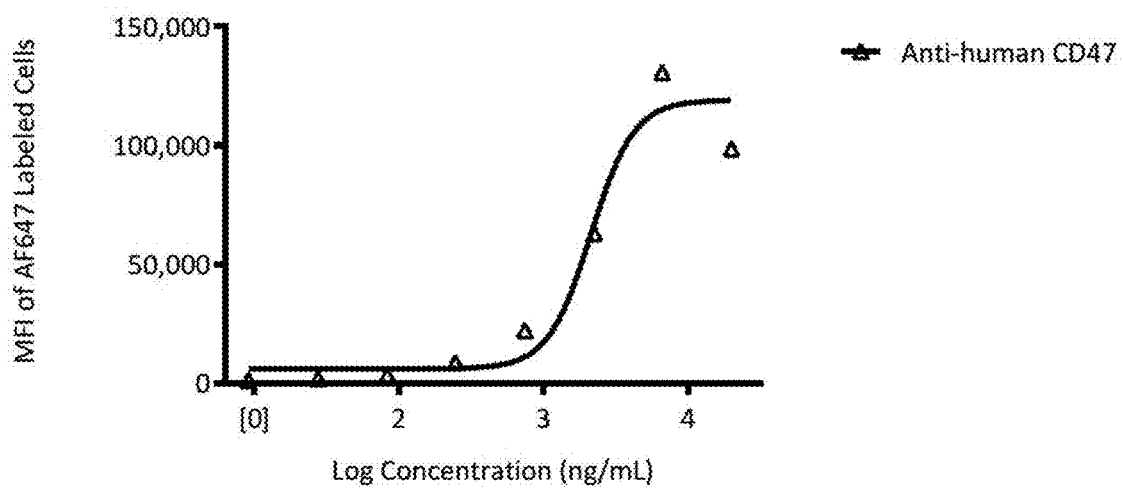

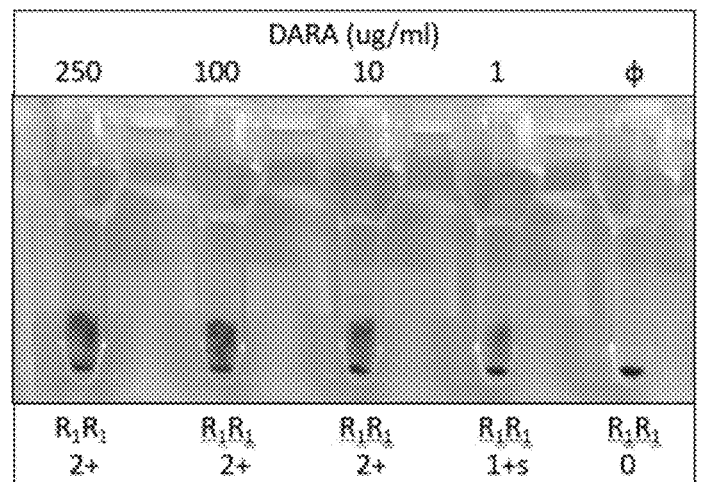
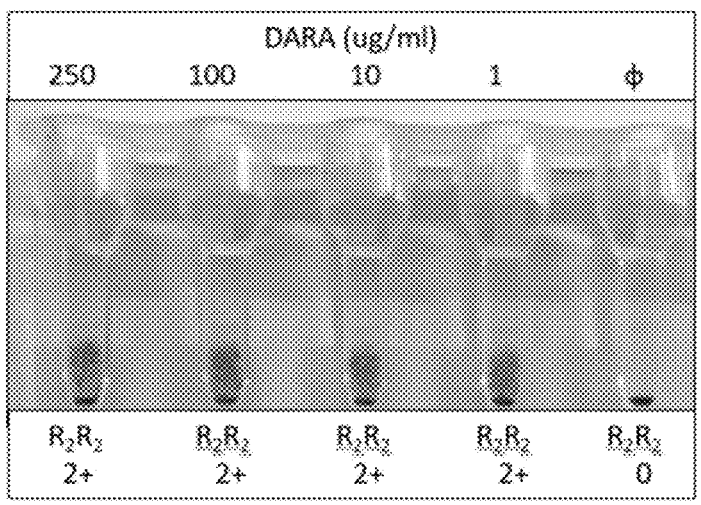
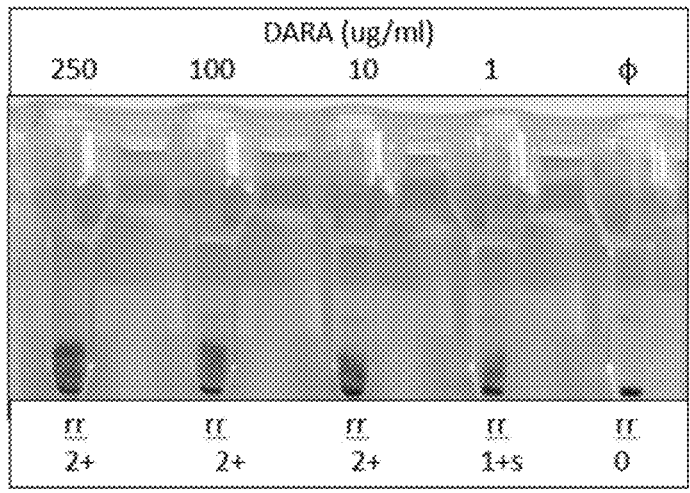

SEQUENCE LISTING

```
<160> NUMBER OF SEQ ID NOS: 34

<210> SEQ ID NO 1
<211> LENGTH: 11
<212> TYPE: PRT
<213> ORGANISM: Homo sapiens

<400> SEQUENCE: 1

Gly Ser Ile Ser Ser Ser Asp Tyr Tyr Trp Gly
1               5                   10

<210> SEQ ID NO 2
<211> LENGTH: 16
<212> TYPE: PRT
<213> ORGANISM: Homo sapiens

<400> SEQUENCE: 2

Ser Ile Tyr Tyr Ser Gly Ser Thr Tyr Tyr Asn Pro Ser Leu Lys Ser
1               5                   10                  15

<210> SEQ ID NO 3
<211> LENGTH: 16
<212> TYPE: PRT
<213> ORGANISM: Homo sapiens

<400> SEQUENCE: 3

Ala Arg Gly Gln Tyr Ser Ser Gly Trp Tyr Ala Tyr Pro Phe Asp Met
1               5                   10                  15

<210> SEQ ID NO 4
<211> LENGTH: 12
<212> TYPE: PRT
<213> ORGANISM: Homo sapiens
```

<400> SEQUENCE: 4

Arg Ala Ser Gln Ser Val Arg Ser Ser Tyr Leu Ala
1               5                   10

<210> SEQ ID NO 5
<211> LENGTH: 7
<212> TYPE: PRT
<213> ORGANISM: Homo sapiens

<400> SEQUENCE: 5

Gly Ala Ser Ser Arg Ala Thr
1               5

<210> SEQ ID NO 6
<211> LENGTH: 8
<212> TYPE: PRT
<213> ORGANISM: Homo sapiens

<400> SEQUENCE: 6

Gln Gln Asp Gly Asn Val Tyr Thr
1               5

<210> SEQ ID NO 7
<211> LENGTH: 124
<212> TYPE: PRT
<213> ORGANISM: Homo sapiens

<400> SEQUENCE: 7

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Asp Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Gln Tyr Ser Ser Gly Trp Tyr Ala Tyr Pro Phe Asp
            100                 105                 110

Met Trp Gly Gln Gly Thr Met Val Thr Val Ser Ser
    115                 120

<210> SEQ ID NO 8
<211> LENGTH: 107
<212> TYPE: PRT
<213> ORGANISM: Homo sapiens

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Gly Asn Val Tyr
                85                  90                  95

Thr Phe Gly Gly Gly Thr Lys Val Glu Ile Lys
            100                 105

<210> SEQ ID NO 9
<211> LENGTH: 8
<212> TYPE: PRT
<213> ORGANISM: Homo sapiens

<400> SEQUENCE: 9

Gln Gln Glu Ala Asn Val Tyr Thr
1               5

<210> SEQ ID NO 10
<211> LENGTH: 8
<212> TYPE: PRT
<213> ORGANISM: Homo sapiens

<400> SEQUENCE: 10

Gln Gln Asp Ser Asn Val Tyr Thr
1               5

<210> SEQ ID NO 11
<211> LENGTH: 8
<212> TYPE: PRT
<213> ORGANISM: Homo sapiens

<400> SEQUENCE: 11

Gln Gln Asp Ala Asn Val Tyr Thr
1               5

<210> SEQ ID NO 12
<211> LENGTH: 8
<212> TYPE: PRT
<213> ORGANISM: Homo sapiens

<400> SEQUENCE: 12

Gln Gln Glu Gly Asn Val Tyr Thr
1               5

<210> SEQ ID NO 13
<211> LENGTH: 107
<212> TYPE: PRT
<213> ORGANISM: Homo sapiens

<400> SEQUENCE: 13

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Glu Ala Asn Val Tyr
                85                  90                  95

```
Thr Phe Gly Gly Gly Thr Lys Val Glu Ile Lys
            100                 105
```

<210> SEQ ID NO 14
<211> LENGTH: 107
<212> TYPE: PRT
<213> ORGANISM: Homo sapiens

<400> SEQUENCE: 14

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Ser Asn Val Tyr
                85                  90                  95

Thr Phe Gly Gly Gly Thr Lys Val Glu Ile Lys
            100                 105
```

<210> SEQ ID NO 15
<211> LENGTH: 107
<212> TYPE: PRT
<213> ORGANISM: Homo sapiens

<400> SEQUENCE: 15

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Ala Asn Val Tyr
                85                  90                  95

Thr Phe Gly Gly Gly Thr Lys Val Glu Ile Lys
            100                 105
```

<210> SEQ ID NO 16
<211> LENGTH: 107
<212> TYPE: PRT
<213> ORGANISM: Homo sapiens

<400> SEQUENCE: 16

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45
```

```
Ile Tyr Gly Ala Ser Ser Arg Ala Thr Gly Ile Pro Asp Arg Phe Ser
            50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Glu Gly Asn Val Tyr
                 85                  90                  95

Thr Phe Gly Gly Gly Thr Lys Val Glu Ile Lys
                100                 105
```

<210> SEQ ID NO 17
<211> LENGTH: 11
<212> TYPE: PRT
<213> ORGANISM: Homo sapiens

<400> SEQUENCE: 17

```
Gly Ser Ile Ser Ser Asp Tyr Tyr Trp Gly
 1               5                  10
```

<210> SEQ ID NO 18
<211> LENGTH: 16
<212> TYPE: PRT
<213> ORGANISM: Homo sapiens

<400> SEQUENCE: 18

```
Ser Ile Tyr Tyr Ser Gly Ser Thr Tyr Tyr Asn Pro Ser Leu Lys Ser
 1               5                  10                  15
```

<210> SEQ ID NO 19
<211> LENGTH: 16
<212> TYPE: PRT
<213> ORGANISM: Homo sapiens

<400> SEQUENCE: 19

```
Ala Arg Gly Gln Tyr Ser Ser Gly Trp Tyr Ala Tyr Pro Phe Asp Met
 1               5                  10                  15
```

<210> SEQ ID NO 20
<211> LENGTH: 12
<212> TYPE: PRT
<213> ORGANISM: Homo sapiens

<400> SEQUENCE: 20

```
Arg Ala Ser Gln Ser Val Arg Ser Ser Tyr Leu Ala
 1               5                  10
```

<210> SEQ ID NO 21
<211> LENGTH: 7
<212> TYPE: PRT
<213> ORGANISM: Homo sapiens

<400> SEQUENCE: 21

```
Gly Ala Ser Ser Arg Ala Thr
 1               5
```

<210> SEQ ID NO 22
<211> LENGTH: 8
<212> TYPE: PRT
<213> ORGANISM: Homo sapiens

<400> SEQUENCE: 22

```
Gln Gln Asp Gly Ala Val Phe Thr
 1               5
```

```
<210> SEQ ID NO 23
<211> LENGTH: 124
<212> TYPE: PRT
<213> ORGANISM: Homo sapiens

<400> SEQUENCE: 23

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asp Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Gln Tyr Ser Ser Gly Trp Tyr Ala Tyr Pro Phe Asp
            100                 105                 110

Met Trp Gly Gln Gly Thr Met Val Thr Val Ser Ser
        115                 120

<210> SEQ ID NO 24
<211> LENGTH: 107
<212> TYPE: PRT
<213> ORGANISM: Homo sapiens

<400> SEQUENCE: 24

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Gly Ala Val Phe
                85                  90                  95

Thr Phe Gly Gly Gly Thr Lys Val Glu Ile Lys
            100                 105

<210> SEQ ID NO 25
<211> LENGTH: 8
<212> TYPE: PRT
<213> ORGANISM: Homo sapiens

<400> SEQUENCE: 25

Gln Gln Asp Glu Ala Val Phe Thr
1               5

<210> SEQ ID NO 26
<211> LENGTH: 8
<212> TYPE: PRT
<213> ORGANISM: Homo sapiens

<400> SEQUENCE: 26
```

```
Gln Gln Asp Ser Ala Val Phe Thr
 1               5
```

```
<210> SEQ ID NO 27
<211> LENGTH: 107
<212> TYPE: PRT
<213> ORGANISM: Homo sapiens

<400> SEQUENCE: 27
```

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Arg Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Asp Glu Ala Val Phe
                 85                  90                  95

Thr Phe Gly Gly Gly Thr Lys Val Glu Ile Lys
            100                 105
```

```
<210> SEQ ID NO 28
<211> LENGTH: 107
<212> TYPE: PRT
<213> ORGANISM: Homo sapiens

<400> SEQUENCE: 28
```

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Arg Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Asp Ser Ala Val Phe
                 85                  90                  95

Thr Phe Gly Gly Gly Thr Lys Val Glu Ile Lys
            100                 105
```

```
<210> SEQ ID NO 29
<211> LENGTH: 300
<212> TYPE: PRT
<213> ORGANISM: Homo sapiens

<400> SEQUENCE: 29
```

```
Met Ala Asn Cys Glu Phe Ser Pro Val Ser Gly Asp Lys Pro Cys Cys
 1               5                  10                  15

Arg Leu Ser Arg Arg Ala Gln Leu Cys Leu Gly Val Ser Ile Leu Val
             20                  25                  30

Leu Ile Leu Val Val Val Leu Ala Val Val Val Pro Arg Trp Arg Gln
         35                  40                  45

Gln Trp Ser Gly Pro Gly Thr Thr Lys Arg Phe Pro Glu Thr Val Leu
```

```
            50                  55                  60
Ala Arg Cys Val Lys Tyr Thr Glu Ile His Pro Glu Met Arg His Val
 65                  70                  75                  80

Asp Cys Gln Ser Val Trp Asp Ala Phe Lys Gly Ala Phe Ile Ser Lys
                     85                  90                  95

His Pro Cys Asn Ile Thr Glu Glu Asp Tyr Gln Pro Leu Met Lys Leu
                100                 105                 110

Gly Thr Gln Thr Val Pro Cys Asn Lys Ile Leu Leu Trp Ser Arg Ile
                115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
                180                 185                 190

Ser Arg Arg Phe Ala Glu Ala Ala Cys Asp Val Val His Val Met Leu
                195                 200                 205

Asn Gly Ser Arg Ser Lys Ile Phe Asp Lys Asn Ser Thr Phe Gly Ser
210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ser Lys Arg Asn Ile Gln
                260                 265                 270

Phe Ser Cys Lys Asn Ile Tyr Arg Pro Asp Lys Phe Leu Gln Cys Val
                275                 280                 285

Lys Asn Pro Glu Asp Ser Ser Cys Thr Ser Glu Ile
290                 295                 300

<210> SEQ ID NO 30
<211> LENGTH: 15
<212> TYPE: PRT
<213> ORGANISM: Homo sapiens

<400> SEQUENCE: 30

Ala Arg Cys Val Lys Tyr Thr Glu Ile His Pro Glu Met Arg His
 1                   5                  10                  15

<210> SEQ ID NO 31
<211> LENGTH: 452
<212> TYPE: PRT
<213> ORGANISM: Homo sapiens

<400> SEQUENCE: 31

Glu Val Gln Leu Leu Glu Ser Gly Gly Gly Leu Val Gln Pro Gly Gly
 1                   5                  10                  15

Ser Leu Arg Leu Ser Cys Ala Val Ser Gly Phe Thr Phe Asn Ser Phe
                 20                  25                  30

Ala Met Ser Trp Val Arg Gln Ala Pro Gly Lys Gly Leu Glu Trp Val
                 35                  40                  45

Ser Ala Ile Ser Gly Ser Gly Gly Thr Tyr Tyr Ala Asp Ser Val
             50                  55                  60

Lys Gly Arg Phe Thr Ile Ser Arg Asp Asn Ser Lys Asn Thr Leu Tyr
```

```
             65                  70                  75                  80
Leu Gln Met Asn Ser Leu Arg Ala Glu Asp Thr Ala Val Tyr Phe Cys
                 85                  90                  95
Ala Lys Asp Lys Ile Leu Trp Phe Gly Glu Pro Val Phe Asp Tyr Trp
                100                 105                 110
Gly Gln Gly Thr Leu Val Thr Val Ser Ser Ala Ser Thr Lys Gly Pro
                115                 120                 125
Ser Val Phe Pro Leu Ala Pro Ser Ser Lys Ser Thr Ser Gly Gly Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
                180                 185                 190
Val Pro Ser Ser Ser Leu Gly Thr Gln Thr Tyr Ile Cys Asn Val Asn
                195                 200                 205
His Lys Pro Ser Asn Thr Lys Val Asp Lys Arg Val Glu Pro Lys Ser
            210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
                260                 265                 270
His Glu Asp Pro Glu Val Lys Phe Asn Trp Tyr Val Asp Gly Val Glu
            275                 280                 285
Val His Asn Ala Lys Thr Lys Pro Arg Glu Glu Gln Tyr Asn Ser Thr
            290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
                340                 345                 350
Val Tyr Thr Leu Pro Pro Ser Arg Glu Glu Met Thr Lys Asn Gln Val
                355                 360                 365
Ser Leu Thr Cys Leu Val Lys Gly Phe Tyr Pro Ser Asp Ile Ala Val
                370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
                420                 425                 430
Met His Glu Ala Leu His Asn His Tyr Thr Gln Lys Ser Leu Ser Leu
            435                 440                 445
Ser Pro Gly Lys
        450

<210> SEQ ID NO 32
<211> LENGTH: 214
<212> TYPE: PRT
<213> ORGANISM: Homo sapiens
```

<400> SEQUENCE: 32

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 33
<211> LENGTH: 450
<212> TYPE: PRT
<213> ORGANISM: Homo sapiens

<400> SEQUENCE: 33

```
Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
                20                  25                  30

Trp Met Gln Trp Val Lys Gln Arg Pro Gly Gln Gly Leu Glu Trp Ile
            35                  40                  45

Gly Thr Ile Tyr Pro Gly Asp Gly Asp Thr Gly Tyr Ala Gln Lys Phe
    50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140
```

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 34
<211> LENGTH: 214
<212> TYPE: PRT
<213> ORGANISM: Homo sapiens

<400> SEQUENCE: 34

Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Gln Lys Pro Gly Gln Ser Pro Arg Arg Leu Ile
        35                  40                  45

Tyr Ser Ala Ser Tyr Arg Tyr Ile Gly Val Pro Asp Arg Phe Thr Gly

```
            50                  55                  60
Ser Gly Ala Gly Thr Asp Phe Thr Phe Thr Ile Ser Ser Val Gln Ala
65                      70                  75                  80

Glu Asp Leu Ala Val Tyr Tyr Cys Gln Gln His Tyr Ser Pro Pro Tyr
                    85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
210
```

METHODS OF BLOOD SCREENING

CROSS-REFERENCE TO RELATED APPLICATIONS

This application claims the benefit of U.S. Provisional Patent Application No. 63/076,489, filed Sep. 10, 2020, and EP patent application No. 20216639.3, filed Dec. 22, 2020, the disclosures of which are incorporated herein by reference in their entirety.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206189-0014-00US_Sequence_Listing.txt" in ASCII format. The text file containing the Sequence Listing of the present application was created on Sep. 7, 2021 and is 27,619 bytes in size.

FIELD OF THE INVENTION

The present invention relates to methods of identifying suitable donor blood for cancer patients receiving anti-CD38 antibodies as treatment. In particular, the present invention addresses problems associated with crossmatching patient and donor blood when the patient blood comprises anti-CD38 antibodies that interfere with crossmatching methods of the art.

BACKGROUND

CD38 is a type II membrane receptor glycoprotein having enzymatic activities, in particular as an important ADP-ribosyl cyclase that produces cyclic adenosine diphosphate ribose (cADPR) from nicotinamide adenine dinucleotide. CD38 is found on the surface of many cell types that are involved in immunological responses (in short referred to as immune cells), including effector cells such as T and B lymphocytes and NK cells, but also immune suppressive cells such as regulatory T and B cells, myeloid derived suppressor cells (MDSCs) or tumour associated macrophages (Chevrier S et al. 2017). CD38 is also expressed on the surface of red blood cells (RBCs).

CD38 is highly expressed by cancer cells in multiple myeloma patients at all stages of disease and in chronic lymphocytic leukemia (CLL) patients with a poor prognosis. Anti-CD38 monoclonal antibody therapies have been developed for targeted, direct killing of CD38-expressing tumor cells. Daratumumab and isatuximab are both anti-CD38 mAbs approved for the treatment of multiple myeloma. However, such anti-CD38 antibodies are known to also bind to CD38 expressed on the surface of RBCs, causing interference on a range of haematological tests performed by blood banks in order to screen and match a patient's blood prior to receiving a red blood cell transfusion. Red blood cell transfusions are of particular importance for multiple myeloma patients, who require frequent RBC transfusions as part of their supportive care.

Anti-CD38 antibodies such as daratumumab and isatuximab are known to cause interference on indirect antiglobulin tests (IATs), antibody detection (screening) tests, antibody identification panels, and antihuman globulin (AHG) crossmatches (Regan & Markowitz; 2016). If a patient has been treated with an anti-CD38 antibody, the interference caused by the anti-CD38 antibodies in the patient's serum can lead to a false indication that the patient's serum contains clinically significant antibodies, i.e. those antibodies that would cause destruction of a donor's red blood cells if transfused (known as haemolytic transfusion reaction). The anti-CD38 antibodies in the patient serum also cause interference on blood crossmatching, the process of matching a patient with compatible donor RBCs. Treating a patient with daratumumab or isatuximab prior to crossmatching can cause compatible crossmatches to appear incompatible. Thus, the interference caused by anti-CD38 antibodies leads to delays in identifying suitable donor red blood cells for transfusions, and can mask the presence of clinically significant antibodies in the serum of the patient, thereby increasing the risk of haemolytic transfusion reactions. Furthermore, the interference can persist for up to six months after treatment with the anti-CD38 antibody is stopped (Darzalex® package insert. Janssen Biotech, 2015; Oostendorp et al. 2015).

Currently available strategies to minimise the interference caused by anti-CD38 antibodies include treating donor or reagent RBCs with antigen stripping agents that remove CD38, such as dithiothreitol (DTT), trypsin or alpha chymotrypsin. In addition, RBC phenotyping or genotyping can be performed on patient RBCs prior to beginning daratumumab. This enables blood banks to provide phenotype or genotype-matched RBCs when a transfusion is urgent or the daratumumab interference cannot be immediately resolved by another method. However, genotyping and phenotyping methods are time-consuming, expensive and may not guarantee a match with donor RBCs. DTT and trypsin can also denature and weaken the reactivity of some RBC antigens, in particular the Kell system antigens, making it difficult to perform an accurate crossmatch. A further strategy to resolve anti-CD38 interference is to neutralise the anti-CD38 antibody in the patient's plasma, for example by treating the plasma or serum sample with soluble CD38 antigen. However, such an approach is expensive and not routinely available. Thus, there is a need for an anti-CD38 antibody that does not cause interference on haematological testing such as crossmatching, and that can be exploited for treating cancer, in particular patients with multiple myeloma.

SUMMARY OF THE INVENTION

In a first aspect, the present invention provides a method of screening a blood sample obtained from a patient, wherein the patient has been administered an anti-CD38 antibody or antigen binding fragment thereof, the method comprising:
  a) providing a blood sample from the patient;
  b) providing a blood sample from a donor, wherein the donor blood sample comprises donor red blood cells; and
  c) screening the patient blood sample, comprising determining the presence or absence of one or more patient antibodies in the patient blood sample from the patient that specifically bind to one or more red blood cell antigens expressed on the surface of the donor red blood cells.

The anti-CD38 antibody or antigen binding fragment thereof is generally an anti-CD38 antibody that, when present in a mixture of patient blood (for example patient serum or plasma) and donor red blood cells, and when the mixture of patient blood (for example patient serum or plasma) and donor red blood cells does not comprise any patient-derived antibodies that bind red blood cell antigens expressed on the donor red blood cells, does not cause agglutination of donor red blood cells when an agglutination agent (such as an anti-human globulin antibody) is added to the mixture. In some embodiments, the anti-CD38 antibody or antigen binding fragment thereof binds an epitope comprising amino acids 65-79 of SEQ ID NO: 29 (human CD38).

The patient antibodies may be alloantibodies. For example, in some embodiments, the antibodies are alloantibodies, in particular alloantibodies that specifically bind to red blood cell antigens. As the antibodies are alloantibodies, they specifically bind to red blood cell antigens other than any red blood cell antigens expressed by the patient's red blood cells.

In some embodiments, the method comprises:
 (a) providing a blood sample from a patient;
 (b) providing a blood sample from a donor, wherein the donor blood sample comprises donor red blood cells;
 (c) contacting the patient blood sample with one or more donor red blood cells from the donor blood sample to provide a patient blood/donor red blood cell mixture;
 (d) optionally incubating the patient blood/donor red blood cell mixture to enable any one or more patient antibodies in the patient blood sample, if present, to bind to one or more red blood cell antigens present on the one or more donor red blood cells, to form one or more patient antibody/donor red blood cell antigen complexes;
 (e) optionally separating, if present, the any one or more patient alloantibody/donor red blood cell antigen complexes from the patient blood/donor red blood cell mixture, optionally wherein the separating step comprises centrifugation; and
 (f) determining the presence or absence of patient antibodies in the patient blood sample that specifically bind to one or more red blood cell antigens expressed on the one or more donor red blood cells.

In a second aspect, the present invention provides a method of treating a cancer in a patient, the method comprising providing a blood sample from the patient, and screening the blood sample according to a screening method of the invention. In some embodiments, the patient has been administered an anti-CD38 antibody or antigen binding fragment thereof (i.e. they have already received the anti-CD38 antibody or antigen binding fragment thereof at an earlier point in time). In other embodiments, the method comprises the set of administration of the anti-CD38 antibody or antigen binding fragment thereof to the patient. In some embodiments, the method may alternatively or additionally comprise a step of obtaining the sample from the patient.

In a third aspect, the present invention provides an anti-CD38 antibody or antigen binding fragment thereof for use in a method of treating a cancer in a patient according to the present invention.

BRIEF DESCRIPTION OF DRAWINGS

FIG. 4A: Dose response curve of CID103 (aCD38-b-348) binding to RBCs of Donor 1 Blood substrate (5% RBC suspension in PBS) from Donor 1 was incubated with various concentrations of the anti-CD38 antibodies CID103 (aCD38-b-348) and daratumumab (Darzalex). An isotype control human IgG1 antibody was used as a negative control. FIG. 4A shows the dose response curve for antibody binding to RBCs. Each data point is presented as mean value from triplicates.

FIG. 4B: Dose response curve of anti-CD47 binding to RBCs of Donor 1 Blood substrate (5% RBC suspension in PBS) from Donor 1 was incubated with various concentrations of Alexa Fluor 647-conjugated anti-CD47 antibody. Anti-CD47 antibody was used as a positive control to demonstrate specific binding to red blood cells. FIG. 4B shows the dose response curve for binding of the control anti-CD47 antibody to RBCs. Each data point is presented as mean value from triplicates.

FIG. 5A: Dose response curve of CID103 (aCD38-b-348) binding to RBCs of Donor 2 Blood substrate (5% RBC suspension in PBS) from Donor 2 was incubated with various concentrations of the anti-CD38 antibodies CID103 (aCD38-b-348) and daratumumab (Darzalex). An isotype control human IgG1 antibody was used as a negative control. FIG. 5A shows the dose response curve for antibody binding to RBCs. Each data point is presented as mean value from triplicates.

FIG. 5B: Dose response curve of anti-CD47 binding to RBCs of Donor 2 Blood substrate (5% RBC suspension in PBS) from Donor 2 was incubated with various concentrations of Alexa Fluor 647-conjugated anti-CD47 antibody. Anti-CD47 antibody was used as a positive control to demonstrate specific binding to red blood cells. FIG. 5B shows the dose response curve for binding of the control anti-CD47 antibody to RBCs. Each data point is presented as mean value from triplicates.

FIG. 6A: Dose response curve of CID103 (aCD38-b-348) binding to RBCs of Donor 3 Blood substrate (5% RBC suspension in PBS) from Donor 3 was incubated with various concentrations of the anti-CD38 antibodies CID103 (aCD38-b-348) and daratumumab (Darzalex). An isotype control human IgG1 antibody was used as a negative control. FIG. 6A shows the dose response curve for antibody binding to RBCs. Each data point is presented as mean value from triplicates.

FIG. 6B: Dose response curve of anti-CD47 binding to RBCs of Donor 3 Blood substrate (5% RBC suspension in PBS) from Donor 3 was incubated with various concentrations of Alexa Fluor 647-conjugated anti-CD47 antibody. Anti-CD47 antibody was used as a positive control to demonstrate specific binding to red blood cells. FIG. 5B shows the dose response curve for binding of the control anti-CD47 antibody to RBCs. Each data point is presented as mean value from triplicates.

FIG. 7: IgG gel cards showing daratumumab interference on testing with Rh positive and Rh negative RBCs Donor RBCs (Rh phenotype: R1R1 (FIG. 7A), R2R2 (FIG. 7B), rr (FIG. 7C)) were incubated with daratumumab (DARA) at various concentrations in inert AB plasma and assayed for interference (i.e. the presence of an agglutination reaction despite no clinically significant alloantibodies being present in the sample) using an IgG gel card assay (Ortho MTS). FIGS. 7A-C show the results at each concentration tested and for each Rh phenotype. Daratumumab concentration is indicated above each microtube, ϕ indicates no drug is present. Rh phenotype is indicated below each well. IgG gel cards were scored by trained personnel according to the degree of agglutination observed, with 4+, 3+, 2+ and 1+ all indicating the presence of an agglutination reaction. A rating of 0 or 0? indicates no agglutination or questionable agglutination. Agglutination ratings are shown below each well.

FIG. 8: IgG gel card testing of CID103 (aCD38-b-348) with Rh positive and Rh negative RBCs Donor RBCs (Rh phenotype: R1R1 (FIG. 8A), R2R2 (FIG. 8B), rr (FIGS. 8C, 8D)) were incubated with CID103 (aCD38-b-348) at various concentrations in inert AB plasma and assayed for interference (i.e. the presence of an agglutination reaction despite no clinically significant alloantibodies being present in the sample) using an IgG gel card assay (Ortho MTS).

FIG. 9: IgG gel card testing of daratumumab and CID103 (aCD38-b-348) with untreated and pre-treated RBCs RhD negative (rr) RBCs were either untreated, or treated with papain, trypsin or ficin prior to incubation with various concentrations of CID103 (aCD38-b-348) or daratumumab (DARA). Samples were assayed for interference (i.e. the presence of an agglutination reaction despite no clinically significant alloantibodies being present in the sample) using an IgG gel card assay (Ortho MTS).

FIG. 10 shows an image of the result. The IH-1000 returned a result of "not interpretable". Following evaluation by trained personnel, the result was determined as having no agglutination.

DETAILED DESCRIPTION

Figure 1:
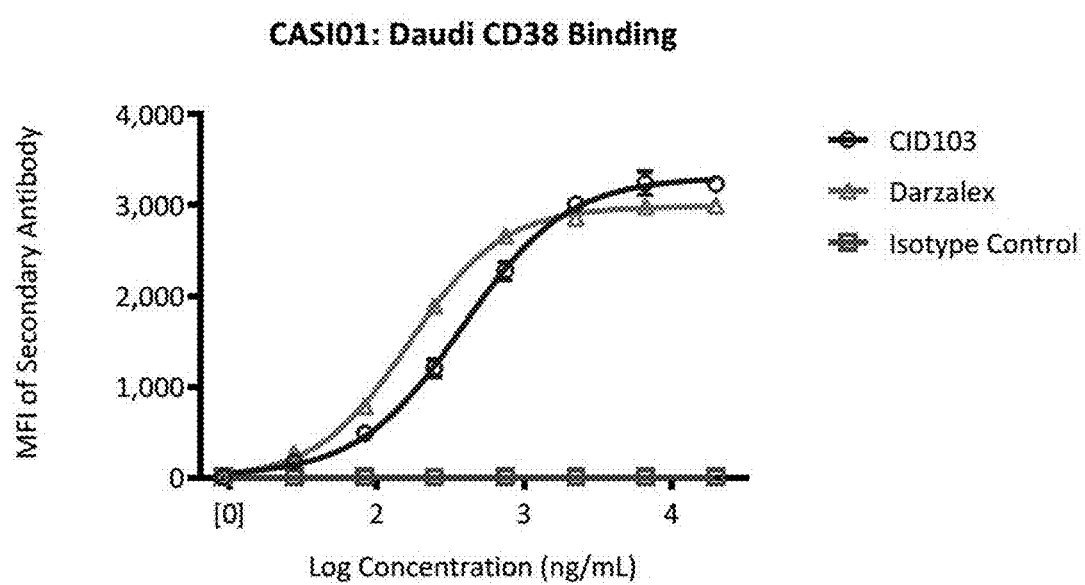
FIG. 1: Dose-response curve of CID103 (aCD38-b-348) binding to Daudi cells Daudi cells were incubated with various concentrations of the anti-CD38 antibodies CID103 or daratumumab (Darzalex) and binding was detected with an Alexa-647-conjugated F(ab')2 secondary antibody. An isotype control human IgG1 mAb was used as a negative control. Each data point is presented as mean value from triplicates, error bars represent SEM.

For the first time, the present invention enables testing of patient blood samples using standard techniques, even when the patient has been treated with anti-CD38 antibodies (also referred to herein as CD38 Modulating Antibody Agents). Most therapeutic anti-CD38 antibodies (including, for example, daratumumab and isatuximab) interfere with tests for identifying antibodies (i.e. clinically significant antibodies) in the patient's blood that may make a given donor blood unsuitable, due to the possibility of haemolysis due to the presence of antibodies in the patient's blood that bind to antigens on the donor red blood cells. Interference occurs because the therapeutic anti-CD38 antibodies bind to CD38 expressed on the surface of the donor red blood cells, which then agglutinate on addition of an anti-human globin reagent or similar. This reagent would usually cause any clinical significant alloantibodies in the patient's serum that have bound to any antigens on the donor red blood cells to bind together and cause agglutination. However, the present of anti-CD38 antibodies in the patient serum causes a false positive result, since agglutination will occur even in the absence of any clinically significant alloantibodies.

In particular, the present inventors have surprisingly discovered that, although most therapeutic antibodies cause this interference, certain anti-CD38 antibodies do not. Without wishing to be bound by theory, the present inventors have found that antibodies binding to particular epitopes of anti-CD38 do not cause interference and thus allow blood typing and crossmatching to take place with standard techniques, without the need for antigen stripping agents or the like.

The methods of the invention detect the presence or absence of clinically significant patient antibodies in the patient blood sample. In some embodiments, the methods of the invention detect the presence or absence of alloantibodies in the patient (for example clinically significant alloantibodies). As used herein, the term "alloantibody" refers to an antibody that specifically binds a red blood cell antigen that is not present on the subject's own red blood cells. The alloantibodies are therefore anti-red blood cell antigen alloantibodies. Alloantibodies are distinguishable from "autoantibodies", which refers to an antibody that specifically binds an antigen present on the subject's own red blood cells. Both alloantibodies and autoantibodies may be detected by the methods of the present invention. For an alloantibody to develop, an individual must be exposed to a non-self RBC antigen and have an HLA-binding motif capable of presenting a portion of the non-self antigen (Tormey & Hendrickson, 2019). Exposure to non-self antigens can occur through pregnancy, transfusion or transplantation, for example. The process of forming an alloantibody is called "alloimmunisation". Alloantibodies may be clinically significant, leading to either destruction (haemolysis) of transfused RBCs or harm to a foetus or newborn, in the case of a mother carrying alloantibodies against an antigen on the baby's red blood cells. Indeed, alloimmunisation can be a direct cause of transfusion-associated mortality. Alloimmunisation also gives rise to further complications in patient treatment, such as transfusion delays, difficulties in locating compatible blood for highly alloimmunised individuals, and delayed or acute haemolytic transfusion reactions. Alloimmunisation is of particular clinical importance for oncology patients, who receive frequent blood transfusions as part of their supportive care and are at greater risk of developing alloantibodies (Hendrickson & Tormey, 2016). As such, it is important that patient samples can be screened for the presence of alloantibodies accurately and quickly. Patients treated with anti-CD38 antibodies, such as daratumumab or isatuximab, may experiences delays on screening for alloantibodies due to the presence of the anti-CD38 antibody or antigen binding fragment thereof in their serum, which binds to CD38 on RBCs and gives the false indication that alloantibodies are present. Antibody screening tests and blood crossmatching, which are used to detect alloantibodies, can be modified to incorporate steps to avoid this interference by anti-CD38 antibodies. For example, RBCs may be treated with an antigen-stripping agent (such as DTT) or the patient sample may be treated with an anti-CD38 neutralising agent (such as soluble CD38). However, such additional reagents result in additional cost and are not widely available, and the extra method steps are time-consuming and introduce delay to antibody screening. The methods of the present invention enable the detection of alloantibodies in a patient sample without the requirement for additional processing of RBCs or patient blood samples. Using the methods of the present invention, the anti-CD38 antibody or antigen binding fragment thereof does not result in interference (for example, agglutination in the absence of clinically significant alloantibodies) on antibody screening or crossmatching, thereby minimising cost and avoiding delay in identifying compatible blood products for transfusion.

Definitions

Below are provided certain definitions of terms, technical means, and embodiments used herein, many or most of which confirm common understanding of those skilled in the art.

Administration:

As used herein, the term "administration" refers to the administration of a composition to a subject. Administration to an animal subject (e.g., to a human) may be by any appropriate route. For example, in some embodiments, administration may be bronchial (including by bronchial instillation), buccal, enteral, intra-arterial, intra-dermal, intra-gastric, intra-medullary, intra-muscular, intra-nasal, intra-peritoneal, intra-thecal, intra-venous, intra-ventricular, within a specific organ or tissue (e.g. intra-hepatic, intra-tumoral, peri-tumoral, etc), mucosal, nasal, oral, rectal, subcutaneous, sublingual, topical, tracheal (including by intra-tracheal instillation), transdermal, vaginal and vitreal. The administration may involve intermittent dosing. Alternatively, administration may involve continuous dosing (e.g., perfusion) for at least a selected period of time. As is known in the art, antibody therapy is commonly administered parenterally, e.g. by intravenous, subcutaneous, or intratumoral injection (e.g., particularly when high doses within a tumor are desired).

Agents that Inhibit Binding of an Anti-CD38 Antibody to Membrane-Bound CD38:

As has already been described, treatment of a patient with an anti-CD38 antibody or antigen binding fragment thereof, such as daratumumab or isatuximab, can lead to inaccurate results on blood screening such as blood antibody screening and crossmatching. For example, daratumumab or isatuximab, when present in a patient sample, cause an agglutination reaction to occur when incubated with RBCs in an indirect antiglobulin test (IAT), falsely indicating the presence of clinically significant antibodies in the patient sample. In order to overcome this problem, steps must be taken to inhibit the binding of the anti-CD38 antibody or antigen binding fragment thereof to membrane-bound CD38. This may involve treating the donor or panel RBCs with an agent that inhibits binding of the anti-CD38 antibody or antigen binding fragment thereof to membrane-bound CD38. Such an agents may be referred to as an "anti-CD38 neutralising agent" or an a "CD38 neutralising agent". Examples of CD38 neutralising agents include an antigen-stripping agents. As used herein, the term "antigen-stripping agent" can refer to any agent used to remove an antigen from the surface of RBCs. In particular, an antigen-stripping agent may be used to remove CD38 from RBCs. In some embodiments, the antigen-stripping agent is a redox reagent or an enzyme. In some embodiments, the antigen-stripping agent is dithiothreitol (DTT). DTT is a thiol-reducing agent that denatures RBC surface CD38 by disrupting the disulphide bonds in the molecule's extracellular domain, therefore preventing anti-CD38 from binding to the RBC. In some embodiments, the antigen-stripping agent is an enzyme. In some embodiments, the antigen-stripping agent is a protease. In some embodiments, the antigen-stripping agent is trypsin. Trypsin is a proteolytic enzyme that is less efficient than DTT treatment at cleaving cell-surface CD38. In some embodiments, the antigen-stripping agent is alpha chymotrypsin. In some embodiments, the antigen-stripping agent is papain. In some embodiments, the antigen-stripping agent is ficin. In some embodiments, the methods of the invention do not comprise a step of treating RBCs with an agent that inhibits binding of an anti-CD38 antibody or antigen binding fragment thereof to membrane-bound CD38, for example they do not comprise a step of contacting the reaction mixture with a CD38 neutralising agent, such as an antigen stripping agent. In some embodiments, the methods of the invention do not comprise a step of treating RBCs with an antigen-stripping agent. In some embodiments, the methods of the invention do not comprise a step of removing CD38 from RBCs.

A patient sample, such as a serum sample or a plasma sample, may also be treated with an "anti-CD38 neutralising agent". As used herein, an anti-CD38 neutralising agent is any substance used to neutralise, through binding or otherwise, an anti-CD38 antibody or antigen binding fragment thereof in a patient sample. An anti-CD38 neutralising agent may be used to bind an anti-CD38 antibody or antigen binding fragment thereof in a serum or plasma or whole blood sample from a patient prior to blood screening. In some embodiments, the anti-CD38 neutralising agent may be a soluble CD38 antigen. In some embodiments, the anti-CD38 neutralising agent may be an anti-CD38 idiotype antibody. In some embodiments, the methods of the invention do not comprise a step of treating a sample from a patient with an anti-CD38 neutralising agent. In some embodiments, the methods of the invention do not comprise a step of treating a sample from a patient with an agent that inhibits binding of anti-CD38 to membrane-bound CD38.

The methods of the invention, incorporating the use of the anti-CD38 antibodies disclosed herein (not daratumumab or isatuximab, but rather the aCD38-b-348 or aCD38-b-329 antibodies or antibodies derived therefrom (such as variants described elsewhere) advantageously do not require the use of any agents that inhibit binding of an anti-CD38 antibody or antigen binding fragment thereof to membrane-bound CD38 (either anti-CD38 neutralising agents or CD38 neutralising agents).

Agglutination:

As used herein, the term "agglutination" or "haemagglutination" refers to any process by which multiple RBCs become bound by an antibody or antibodies and aggregate together. Agglutination is a reversible chemical reaction thought to occur in two stages: 1) sensitization when an antibody attaches to a red cell antigen, and 2) agglutination when the sensitized red cells are bridged together to form a lattice. If a patient sample contains antibodies specific for RBC antigens present on donor RBCs, when the patient sample and donor RBCs are mixed the antibodies will bind the RBC antigens (sensitisation). Some antibodies, such as IgM antibodies, may cause agglutination directly by binding to one another. Other antibodies, such as IgG antibodies, may require the addition of an agglutination agent in order to bridge together or connect the bound antibodies and produce agglutination. The agglutination agent that binds together any antibodies present in the patient blood sample. In particular, the agglutination agent may bind together any patient-derived antibodies and/or any anti-CD38 antibodies. If the agglutinated patient-derived antibodies and/or the anti-CD38 antibodies are bound to the red blood cells, the agglutination agent will also cause the RBCs to agglutinate.

The methods of the invention may use certain agglutination agents such as anti-human globulin agents. The anti-human globulin agents may be anti-human IgG antibodies, since the patient-derived antibodies that specifically bind RBC antigens are usually IgG antibodies. However, the anti-human goblin agent may alternatively or additionally comprise anti-C3 antibodies. Generally, the agglutination agent is an agent that causes any antibodies comprising a human constant region (in particular a human IgG constant region) to bind together. Even though the anti-CD38 antibodies described herein (i.e. aCD38-b-348 and aCD38-b-329 or antibodies derived therefrom) may comprising a human constant region (for example they may of a human IgG isotype), the presence of the agglutination agent surprisingly does not cause in the anti-CD38 antibodies to agglutinate in such a way that causes interference with the screening step.

The agglutination agent (e.g. the anti-human globulin reagent) binds together the patient antibodies that are bound to the donor RBCs. RBCs bound to an antibody may be reduced to a visible pellet when centrifuged, for example in an indirect antiglobulin test (IAT) performed in a tube. Agglutination is assessed on a 0-4+ scale, with 0 representing no agglutination, and 4+ indicating a very strong agglutination reaction. Agglutination is the basis for the majority of tests which determine whether a donor red blood cell sample is compatible with a patient's blood sample and thus whether the donor RBCs are suitable for transfusion. The occurrence of agglutination may indicate an incompatible match between the patient and the donor red blood cells, because the patient sample contains alloantibodies (clinically significant antibodies) that bind to the RBC antigens on the donor's RBCs. An agglutination result of 1+, 2+, 3+ and 4+ may indicate an incompatible match between a patient and donor RBCs, and that the donor RBCs should not be transfused to the patient. An agglutination result of 0 or 0? may indicate a compatible match between a patient and donor RBCs, and that the donor RBCs could be transfused safely to the patient.

Agglutination may also occur when the patient sample contains certain anti-CD38 antibodies, for example when the patient has been treated with daratumumab or isatuximab. When the patient sample is incubated with the donor RBCs, the anti-CD38 antibody or antigen binding fragment thereof present in the patient sample may bind to CD38 expressed on the surface of the donor RBCs. Agglutination may occur when the agglutination agent (e.g. an anti-human globulin reagent) is added to the patient sample/donor RBC mixture. The agglutination caused by the presence of an anti-CD38 antibody or antigen binding fragment thereof in the patient sample in combination with the agglutination agent may occur irrespective of the presence of clinically significant patient antibodies in the patient sample against RBC antigens on the donor RBCs. In this way, the presence of an anti-CD38 antibody or antigen binding fragment thereof such as daratumumab or isatuximab in the patient sample causes interference on blood crossmatching, such that donor RBCs may appear incompatible for transfusion to the patient, even though the patient does not have alloantibodies against the donor RBC antigens. The use of the anti-CD38 antibodies described herein (i.e. aCD38-b-348 or aCD38-b-329 or antibodies derived therefrom) avoids this problem.

Antibody:

As used herein, the term "antibody" refers to a polypeptide that includes canonical immunoglobulin sequence elements sufficient to confer specific binding to a particular target antigen, such as CD38, human CD38 in particular, and human CD38 extracellular. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long), an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally produced antibodies are also glycosylated, typically on the CH2 domain, and each domain has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3; as understood in the art, for example determined according to Kabat numbering scheme) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen-binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification that can improve the developability of the antibody (Jarasch A et al., 2015).

In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal or oligoclonal, that is generated as a panel of antibodies, each associated to a single antibody sequence and binding a more or less distinct epitopes within an antigen (such as different epitopes within human CD38 extracellular domain that are associated to different reference anti-CD38 antibodies).

Polyclonal or oligoclonal antibodies can be provided in a single preparation for medical uses as described in the literature (Kearns J D et al., 2015). In some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation, for instance as antigen-binding fragments as defined below. For example, an antibody utilized in accordance with the present invention is in a format selected from, but not limited to, intact IgG, IgE and IgM, bi- or multi-specific antibodies (e.g., Zybodies®, etc.), single chain variable domains (scFv), polypeptide-Fc fusions, Fabs, cameloid antibodies, heavy-chain shark antibody (IgNAR), masked antibodies (e.g., Probodies®), or fusion proteins with polypeptides that allow expression and exposure on the cell surface (as scFv within constructs for obtaining artificial T cell receptors that are used to graft the specificity of a monoclonal antibody onto a T cell). In some embodiments, an antibody may lack a covalent modification (e.g., attachment of a glycan) that it would have if produced naturally. Alternatively, an antibody may contain a covalent modification (e.g., attachment of a glycan, a payload [e.g., a detectable moiety, a therapeutic moiety, a catalytic moiety, etc.], or other pendant group [e.g., poly-ethylene glycol, etc.]).

Antibody Screening:

As used herein, the term "antibody screening" refers to any test performed to detect the presence or absence of antibodies in a sample from a patient that specifically bind to one or more red blood cell antigens using a panel of red blood cells. The antibodies detected on antibody screening may be clinically significant, for example, may cause a haemolytic transfusion reaction if the patient receives transfused RBCs expressing antigens to which the antibodies can specifically bind. The antibodies detected on antibody screening may be alloantibodies, i.e. antibodies that specifically bind antigens that are not present on the subject's own RBCs, or autoantibodies, i.e. antibodies that specifically bind to antigens present on the subject's own RBCs. Antibody screening is particularly useful for patients who are likely to have been alloimunised as a result of a previous blood transfusion, for example, patients undergoing treatment for haematological cancers. Antibody screening can be performed according to any of the methods described herein. Antibodies may be detected using an indirect antiglobulin test (IAT). Antibody screening may be performed using a column agglutination assay, a tube assay, or a solid phase assay.

Antibody screening may be performed using a panel of red blood cells, wherein the red blood cells in the panel are known to express specific blood group antigens. Red blood cell panels may comprise RBCs that express any of the blood group antigens described herein. Red blood cell panels may comprise RBCs that express any of the blood group antigens selected from the group consisting of Ab group, ABO group, Cromer group, Diego group, Duffy group, Gerbich group, GLOB group, Indian group, Kell group, Kidd group, Knops group, Lewis group, Lutheran group, LW group, MNS group, P1 group, Rh group, XK group, Xg group, or the Yt group antigens. In particular, red blood cell panels may comprise RBCS that express Kell group antigens, Duffy group antigens, Kidd group antigens, Lewis group antigens, P group antigens, MNS group antigens, Lutheran group antigens and Xg group antigens. Screening a patient sample against a red blood cell panel enables the detection of common clinically relevant patient antibodies. Antibody screening may be performed prior to crossmatching a patient sample against donor RBCs from a specific donor. Antibody screening enables the selection of donor RBCs that do not express RBC antigens identified on antibody screening, thus improving the likelihood of identifying a compatible donor on blood crossmatching.

In some embodiments of the invention, the methods comprises a step of antibody screening against a panel of red blood cells. In some embodiments of the invention, the methods comprise crossmatching a patient blood sample with a candidate donor red blood cell sample. In some embodiments, the methods comprise first performing an antibody screening step using a panel of red blood cells, followed by crossmatching a patient blood sample (from the same patient) with a candidate donor red blood cell sample, wherein the donor red blood cells do not express any red blood cell antigens that were identified as being found by patient-derived antibodies in the antibody screening step.

Anti-CD38 Antibody:

The term "anti-CD38 antibody" (also referred to herein as a CD38 Modulating Antibody Agent") is used herein to refer to those anti-CD38 antibodies that demonstrate particular properties as described herein. References to anti-CD38 antibodies herein include antigen binding fragments thereof, unless the context indicates otherwise. Ins some embodiments, any antigen-binding fragments of anti-CD38 antibodies that are used may comprise an Fc portion, for example a human IgG constant region.

In many embodiments, desirable anti-CD38 antibodies as described herein are characterized in that they stimulate immune effector cells and/or modify immune cells function and are cytotoxic towards or induce phagocytosis of CD38 expressing cells (e.g. expressing high levels of CD38) such as immune suppressive cells or tumour cells (e.g., in each case, that express CD38 on their surfaces). In some embodiments, an anti-CD38 antibody is characterized by an activity (e.g., level and/or type) reasonably comparable to that of aCD38-b-348 or aCD38-b-329 with respect to immune cells (e.g., when contacted with immune cells, and particularly with immune cells that express CD38) and tumour cells. In some embodiments, a relevant activity is or comprises ADCP, ADCC in absence of CDC, direct killing, depletion of certain CD38-expressing cells (e.g., high-expressing cells), effector immune cell activation, promotion of T cell, B cell or NK cell expansion, modulation of immune cells activity (e.g. repolarization of suppressive macrophages into inflammatory macrophages), skewing of T cell repertoire, etc., and combinations thereof. In some embodiments, anti-CD38 antibodies are entities or moieties whose presence or level correlates with level and/or activity of CD38, and/or with one or more features or results characteristic of CD38 activity. In some embodiments, an increased level and/or activity is assessed or determined relative to that observed under otherwise comparable conditions in absence of the entity(ies) or moiety(ies). Alternatively or additionally, in some embodiments, an increased level and/or activity is comparable to or greater than that observed under comparable conditions when a reference anti-CD38 antibody (which in many embodiments is a CD38 agonist antibody, such as IB4) is present. In many embodiments, an anti-CD38 antibody for use in accordance with the present disclosure is or comprises an entity or moiety that binds, directly or indirectly, to CD38, typically to its extracellular domain. In some embodiments, an anti-CD38 antibody is, comprises, or competes for binding to CD38 with an anti-CD38 antibody as disclosed herein, an antigen-binding fragment (e.g., comprising one or more CDRs, all heavy chain CDRs, all light chain CDRs, all CDRs, a heavy chain variable region, a light chain variable region, or both heavy and light chain variable regions) thereof, an affinity matured variant thereof (or an antigen-binding fragment thereof), or any alternative format (e.g., chimeric, humanized, multispecific, alternate isotype, etc) of any of the foregoing. Alternatively or additionally, in some embodiments, an anti-CD38 antibody as disclosed herein may be characterized by one or more features that may be features that are advantageous for screening, manufacturing, (pre-)clinical testing, and/or for identifying relevant epitope within human CD38, such as the sequence identified as aCD38-b-ep), and/or for formulation, administration, and/or efficacy in particular contexts (e.g., for cancer therapy), as disclosed herein.

Antigen:

The term "antigen", as used herein, refers to an agent that elicits an immune response and/or that binds to a T cell receptor (e.g., when presented by an MHC molecule) and/or B cell receptor. An antigen that elicits a humoral response involve the production of antigen-specific antibodies or, as shown in the Examples for CD38 extracellular domain, can be used for screening antibody libraries and identifying candidate antibody sequences to be further characterized.

Antigen-Binding Fragment:

As used herein, the term "Antigen-binding Fragment" encompasses agents that include or comprise one or more portions of an antibody as described herein sufficient to confer on the antigen-binding fragment and ability to specifically bind to the Antigen targeted by the antibody. For example, in some embodiments, the term encompasses any polypeptide or polypeptide complex that includes immunoglobulin structural elements sufficient to confer specific binding. Exemplary antigen-binding fragments include, but are not limited to Small Modular ImmunoPharmaceuticals ("SMIPs™"), single chain antibodies, cameloid antibodies, single domain antibodies (e.g., shark single domain antibodies), single chain or Tandem diabodies (TandAb®), VHHs, Anticalins®, Nanobodies®, minibodies, BiTE®s, ankyrin repeat proteins or DARPINs®, Avimers®, a DART, a TCR-like antibody, Adnectins®, Affilins®, Trans-Bodies®, Affibodies®, a TrimerX®, MicroProteins, Centyrins®, CoVX bodies, BiCyclic peptides, Kunitz domain derived antibody constructs, or any other antibody fragments so long as they exhibit the desired biological activity. In some embodiments, the term encompasses other protein structures such as stapled peptides, antibody-like binding peptidomimetics, antibody-like binding scaffold proteins, monobodies, and/or other non-antibody proteins scaffold, for example as reviewed in the literature (Vazquez-Lombardi R et al., 2015). In some embodiments, an antigen-binding fragment is or comprises a polypeptide whose amino acid sequence includes one or more structural elements recognized by those skilled in the art as a complementarity determining region (CDR). In some embodiments an antigen-binding fragment is or comprises a polypeptide whose amino acid sequence includes at least one reference CDR (e.g., at least one heavy chain CDR and/or at least one light chain CDR) that is substantially identical to one found in an anti-CD38 antibody as described herein (e.g., in an aCD38-b-348 or aCD38-b-329 amino acid sequence element), and in particular at least one heavy chain CDR, such as an HCDR3 (e.g., an aCD38-b-348 or aCD38-b-329 HCDR3 sequence). In some embodiments an antigen-binding fragment is or comprises a polypeptide whose amino acid sequence includes at least one CDR (e.g., at least one heavy chain CDR and/or at least one light chain CDR) that is either identical in sequence or contains a small number (e.g., 1, 2, 3, or 4) more amino acid alterations (e.g., substitutions, additions, or deletions; in many cases, substitutions) relative to such a reference CDR, while maintaining binding to the target of the antibody (e.g., aCD38-b-348 or aCD38-b-329) from which the reference CDR was derived. In some embodiments, an antigen-binding fragment is or comprises a polypeptide or complex thereof that includes all three CDRs (or, in some embodiments, sequences substantially identical thereto) from a heavy or light chain of a reference antibody (e.g., from aCD38-b-348 or aCD38-b-329); in some embodiments, an antigen-binding fragment is or comprises a polypeptide or complex thereof that includes all six CDRs (or, in some embodiments, sequences substantially identical thereto) from a reference antibody (e.g., from aCD38-b-348 or aCD38-b-329). In some embodiments, an antigen-binding fragment is or comprises a polypeptide or complex thereof that includes the heavy and/or light chain variable domains (or, in some embodiments, sequences substantially identical thereto) of a reference antibody (e.g., of aCD38-b-348 or aCD38-b-329). In some embodiments, the term "antigen-binding fragment" encompasses non-peptide and non-protein structures, such as nucleic acid aptamers, for example, RNA aptamers and DNA aptamers. An aptamer is an oligonucleotide (e.g., DNA, RNA, or an analog or derivative thereof) that binds to a particular target, such as a polypeptide. Aptamers are short synthetic single-stranded oligonucleotides that specifically bind to various molecular targets such as small molecules, proteins, nucleic acids, and even cells and tissues. These small nucleic acid molecules can form secondary and tertiary structures capable of specifically binding proteins or other cellular targets, and are essentially a chemical equivalent of antibodies. Aptamers are highly specific, relatively small in size, and non-immunogenic. Aptamers are generally selected from a biopanning method known as SELEX (Systematic Evolution of Ligands by Exponential enrichment) (See for example Ellington et al. Nature. 1990; 346(6287): 818-822; Tuerk et al., Science. 1990; 249(4968):505-510; Ni et al., Curr Med Che 2011; 18(27):4206-14). Methods of generating an aptamer for any given target are well known in the art. Peptide aptamers including affimers are also encompassed. An affimer is a small, highly stable protein engineered to display peptide loops which provide a high affinity binding surface for a specific target protein. It is a protein of low molecular weight, 12-14 kDa, derived from the cysteine protease inhibitor family of cystatins. Affimer proteins are composed of a scaffold, which is a stable protein based on the cystatin protein fold. They display two peptide loops and an N-terminal sequence that can be randomized to bind different target proteins with high affinity and specificity similar to antibodies. Stabilization of the peptide upon the protein scaffold constrains the possible conformations which the peptide may take, thus increasing the binding affinity and specificity compared to libraries of free peptides.

Articles of Manufacture and Kits:

In some embodiments of the invention, an anti-CD38 antibody as described herein is provided in a separate article of manufacture. In some embodiments of the invention, an article of manufacture containing an anti-CD38 antibody is provided in or with a container with a label. Suitable containers may include, for example, bottles, vials, syringes, and test tubes. In some embodiments, a container may be formed from any or a variety of materials such as glass or plastic. In some embodiments, a container holds a composition that is effective for treating a particular disease, disorder, or condition, or stage or type thereof. In some embodiments, a container may have a sterile access port (for example the container may be an intravenous solution bag or a vial having a stopper pierceable by a hypodermic injection needle). For example, in some embodiments, compositions comprising an anti-CD38 antibody as described herein is packaged in clear glass vials with a rubber stopper and an aluminium seal. The label on, or associated with, the container indicates that the composition is used for treating the condition of choice.

In some embodiments, an article of manufacture may further comprise a separate container comprising a pharmaceutically acceptable buffer, such as phosphate-buffered saline, Ringer's solution and dextrose solution and/or may further include other materials desirable from a commercial and user standpoint, including other buffers, diluents, filters, needles, syringes, and package inserts with instructions for use. For example, in some embodiments, an article of manufacture may allow providing each or the agent in an intravenous formulation as a sterile aqueous solution containing a total of 2 mg, 5 mg, 10 mg, 20 mg, 50 mg, or more that are formulated, with appropriate diluents and buffers, at a final concentration of 0.1 mg/ml, 1 mg/ml, 10 mg/ml, or at a higher concentration.

In some embodiments, an anti-CD38 antibody as described herein can be provided within the kits-of-parts in the form of lyophilized is to be reconstituted with any appropriate aqueous solution that provided or not with the kits, or other types of dosage unit using any compatible pharmaceutical carrier. One or more unit dosage forms of an anti-CD38 antibody may be provided in a pack or dispenser device. Such a pack or device may, for example, comprise metal or plastic foil, such as a blister pack. In order to use correctly such kits-of-parts, it may further comprise buffers, diluents, filters, needles, syringes, and package inserts with instructions for use in the treatment of cancer.

In some embodiments, instructions that are associated with an article of manufacture or the kits as described herein may be in the form of a label, a leaflet, a publication, a recording, a diagram, or any other means that can be used to inform about the correct use and/or monitoring of the possible effects of the agents, formulations, and other materials in the article of manufacture and/or in the kit. Instructions may be provided together with the article of manufacture and/or in the kit.

Automated Testing:

As used herein, the terms "automated test", "automated platform" and "automated assay" may refer to any automatic system for the detection of antigen-antibody reactions between a patient or recipient blood sample and a donor blood sample or reagent RBCs. Examples of automated platforms include Tango (BioRad) and IH-1000 (BioRad). Automated testing may be used for solid-phase assays, column agglutination assays, tube assays and/or other assay types. The methods described herein may be suitably performed using automated testing.

Biological Sample:

As used herein, the terms "biological sample" or" "sample" (used interchangeably) typically refers to a sample obtained or derived from a biological source (e.g., a tissue or organism or cell culture) of interest, as described herein. A source of interest may be an organism, such as an animal or human. The biological sample may comprise biological tissue or fluid. The methods described herein relate to screening of a blood sample obtained from a patient. In some embodiments, the patient blood sample is a whole blood sample. In some embodiments, the patient blood sample is a red blood cell sample. In some embodiments, the patient blood sample is a plasma sample. In some embodiments, the patient blood sample is a serum sample. In some embodiments, the patient sample does not comprise any of the patient's own red blood cells.

In some embodiments, the methods described herein include a step of providing a blood sample from a donor. In some embodiments, the donor blood sample is a whole blood sample. In some embodiments, the donor blood sample is a red blood cell sample. In some embodiments, the donor blood sample is a plasma sample. In some embodiments, the donor blood sample is a serum sample. In some embodiments, the patient sample does not comprise any of the patient's own red blood cells.

In some embodiments of the invention, the screening method is conducted on a sample obtained from a patient at an earlier point in time. In other embodiments of the invention, the method may comprise a step of obtaining the sample from the patient, using any suitable method.

The methods of the invention may be performed on multiple samples from the same patient. For example, in m methods comprising both an RBC panel screening and a crossmatching assay, the RBC panel screen may be performed on a first sample from the patient, and the crossmatching assay may be performed on a second, different, sample from the same patient. A single sample may be obtained from the patient and split in to multiple sub-samples for this purpose (or to run the same assays multiple times for the same patient) or multiple different samples may be obtained from the same patient.

The patient sample may be processed prior to mixing with the donor red blood cells, for example to remove the patient RBCs from the patient sample. Other processing steps may additionally be used, such as dilution of the patient sample using a buffer.

Generally, since the patient has previously been administered the anti-CD38 antibodies, the patient sample will comprise the anti-CD38 antibodies.

Cancer:

The terms "cancer", "malignancy", "neoplasm", "tumor", "tumour", and "carcinoma", are used interchangeably herein to refer to cells that exhibit relatively abnormal, uncontrolled, and/or autonomous growth, so that they exhibit an aberrant growth phenotype characterized by a significant loss of control of cell proliferation. In general, cells of interest for detection or treatment in the present application include precancerous (e.g., benign), malignant, pre-metastatic, metastatic, and non-metastatic cells. The teachings of the present disclosure may be relevant to any and all cancers. To give but a few, non-limiting examples, in some embodiments, teachings of the present disclosure are applied to one or more cancers such as, for example, hematopoietic cancers including leukemias, lymphomas (Hodgkins and non-Hodgkins), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastrointestinal cancers and nervous system cancers, benign lesions such as papillomas, and the like.

In some embodiments, the cancer is a cancer comprises cells that express CD38 on the cell surface, i.e. a CD38-expressing cancer. In some embodiments, the cancer may be a solid tumour, such as a solid tumour that expresses CD38 on the cell surface. In some embodiments, the cancer may be a haematological tumour, such as a CD38-expressing haematological tumour. In some embodiments, the cancer may be selected from the group consisting of a T or B cell non-Hodgkin's lymphoma, chronic lymphocytic leukemia, plasmacytoma, and multiple myeloma.

Column Agglutination Technology:

As used herein, the terms "column agglutination assay" or "column agglutination technology" refer to techniques used to identify patient-derived antibodies (such as alloantibodies, in particular clinically significant alloantibodies) in a patient sample that bind to antigens expressed on donor RBCs or reagent RBCs (i.e. red blood cells in a red blood cell panel). Column agglutination technology may be used to perform an IAT. Column agglutination techniques use a microtube or column containing an agglutination agent such as an anti-human globulin (such as anti-IgG and/or anti-C3) gel and use a well above the microtube to allow incubation of donor cells with patient plasma or serum. Samples are then centrifuged through the column containing an anti-human globulin, for example anti-human IgG. During incubation, any relevant patient-derived antibodies present in the patient plasma or serum may bind to antigens expressed on the donor RBCs. Donor RBCs with bound antibodies may be referred to as "sensitised" RBCs. The patient-derived antibodies that are bound to the RBCs may be IgG antibodies. During centrifugation, the patient-derived antibodies bound to donor RBCs react with the anti-human globulin reagent present in the gel, preventing or slowing the movement of the bound RBCs through the microtube or column. Strongly positive agglutination reactions produce a line of RBCs layered at the top of the gel. Positive reactions will have varying degrees of visible red blood cell agglutinates suspended in the gel. Conversely, donor RBCs which are not bound by patient-derived antibodies will move through the gel easily during centrifugation and form a pellet at the bottom of the microtube or column. Column agglutination technology can be used to perform an indirect antiglobulin test (IAT). The results of an assay performed using column agglutination technology can be read by an automated platform such as Tango (BioRad) or IH-1000 (BioRad).

Combination Therapy:

As used herein, the term "combination therapy" refers to those situations in which a subject is simultaneously exposed to two or more therapeutic regimens (e.g., two or more therapeutic agents). In some embodiments, two or more agents may be administered simultaneously. Alternatively, such agents may be administered sequentially; otherwise, such agents are administered in overlapping dosing regimens.

Comparable:

As used herein, the term "comparable" refers to two or more agents, entities, situations, effects, sets of conditions, etc., that may not be identical to one another but that are sufficiently similar to permit comparison (e.g., by level and/or activity) there between so that conclusions may reasonably be drawn based on differences or similarities observed. Such comparable sets of conditions, effects, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, effects, or populations, etc. to be considered comparable.

Comprising:

A composition or method described herein as "comprising" one or more named elements or steps is open-ended, meaning that the named elements or steps are essential, but other elements or steps may be added within the scope of the composition or method. It is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method.

Crossmatching:

As used herein, the term "crossmatching" refers to any test of compatibility between a patient blood sample and a donor blood sample. Crossmatching may refer to testing donor red blood cells for compatibility with recipient or patient serum or plasma, also known as major crossmatching. Crossmatching may be used to identify the presence of clinically significant antibodies in a sample (e.g. a plasma sample or a serum sample) from a patient or transfusion recipient. Clinically significant antibodies are any antibodies likely to result in harmful side-effects, such as haemolytic transfusion reaction, following transfusion of donor blood to the recipient. Clinically significant antibodies may include alloantibodies, which specifically bind antigens that are not expressed on the transfusion recipient or patient's own red blood cells. Clinically significant antibodies may include autoantibodies, which specifically bind antigens that are expressed on the transfusion recipient or patient's own red blood cells. In some embodiments, incompatibility between a patient blood sample and a donor blood sample is indicated by agglutination when the samples are mixed. In some embodiments, compatibility between a patient blood sample and a donor blood sample is indicated by a lack of agglutination when the samples are mixed. In some embodiments, incompatibility between a patient blood sample and a donor blood sample is indicated by haemolysis when the samples are mixed. In some embodiments, compatibility between a patient blood sample and a donor blood sample is indicated by a lack of haemolysis when the samples are mixed. Crossmatching may be performed according to any of the methods described herein. Crossmatching may be performed using a column agglutination assay, an indirect antiglobulin test (IAT) tube assay, or a solid phase assay.

Daratumumab:

As used herein, the term "daratumumab" includes an antibody having, VH and VL sequences as published in WO2006/099875 and being a human IgG1 monoclonal antibody. For example having variable heavy and light chain sequences comprising the sequences as provided below:

Heavy Chain:
(SEQ ID NO: 31)
EVQLLESGGGLVQPGGSLRLSCAVSGFTFNSFAMSWVRQAPGKGLEWVSA

ISGSGGGTYYADSVKGRFTISRDNSKNTLYLQMNSLRAEDTAVYFCAKDK

ILWFGEPVFDYWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKRVEPKSCDKTHTCPPCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK

Light Chain:
(SEQ ID NO: 32)
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPPTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Dosage Form:

As used herein, the term "dosage form" refers to a physically discrete unit of an active agent (e.g., a therapeutic or diagnostic agent) for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing and Administration:

Pharmaceutical compositions comprising an anti-CD38 antibody as described herein (e.g., an anti-CD38 or antigen-binding fragment thereof, for example comprising the aCD38-b-348 or aCD38-b-329 HCDR3 amino acid sequence) for use in accordance with the present invention may be prepared for storage and/or delivery using any of a variety of techniques and/or technologies known and/or available to those skilled in the art. In some embodiments, a disclosed anti-CD38 antibody is administered according to a dosing regimen approved by a regulatory authority such as the United States Food and Drug Administration (FDA) and/or the European Medicines Agency (EMA), e.g., for the relevant indication. In some embodiments, a disclosed anti-CD38 antibody is administered in combination with one or more other agents or therapies, which may themselves be administered according to a dosing regimen approved by a regulatory authority such as the United States Food and Drug Administration (FDA) and/or the European Medicines Agency (EMA), e.g., for the relevant indication. In some embodiments however, use of a disclosed anti-CD38 antibody may permit reduced dosing (e.g., lower amount of active in one or more doses, smaller number of doses, and/or reduced frequency of doses) of an approved agent or therapy used in combination with the anti-CD38 antibody therapy. In some embodiments, dosing and/or administration may be adapted to other drugs that also administered, the patient status, and/or the format of an anti-CD38 antibody (e.g. modified as an immunoconjugate, a nanobody, or a bispecific antibody).

Moreover, in some embodiments, it may be desirable to tailor dosing regimens, and particularly to design sequential dosing regimens, based on timing and/or threshold expression levels of CD38, whether for particular cell types, particular tumors or types thereof, or particular patient populations (e.g., carrying genetic markers). In some such embodiments, therapeutic dosing regimens may be combined with or adjusted in light of detection methods that assess expression of one or more inducible markers or other criteria prior to and/or during therapy.

In some embodiments, dosing and administration according to the present invention utilizes active agent having a desired degree of purity combined with one or more physiologically acceptable carriers, excipients or stabilizers in any or variety of forms. These include, for example, liquid, semi-solid and solid dosage forms, such as liquid solutions (e.g., injectable and infusible solutions), dispersions or suspensions, tablets, pills, powders, liposomes and suppositories. A preferred form may depend on the intended mode of administration and/or therapeutic application, typically in the form of injectable or infusible solutions, such as compositions similar to those used for treating of human subjects with antibodies.

In some embodiments, ingredient(s) can be prepared with carriers that protect the agent(s) against rapid release and/or degradation, such as a controlled release formulation, including implants, transdermal patches, and microencapsulated delivery systems. Biodegradable, biocompatible polymers can be used, such as polyanhydrides, polyglycolic acid, polyorthoesters, and polylactic acid. In general, each active agent is formulated, dosed, and administered in therapeutically effective amount using pharmaceutical compositions and dosing regimens that are consistently with good medical practice and appropriate for the relevant agent(s) (e.g., for agents such as antibodies). Pharmaceutical compositions containing active agents can be administered by any appropriate method known in the art, including, without limitation, oral, mucosal, by-inhalation, topical, buccal, nasal, rectal, or parenteral (e.g. intravenous, infusion, intratumoral, intranodal, subcutaneous, intraperitoneal, intramuscular, intradermal, transdermal, or other kinds of administration involving physical breaching of a tissue of a subject and administration of the pharmaceutical composition through such breach).

In some embodiments, a dosing regimen for a particular active agent may involve intermittent or continuous (e.g., by perfusion or slow release system) administration, for example to achieve a particular desired pharmacokinetic profile or other pattern of exposure in one or more tissues or fluids of interest in the subject. In some embodiments, different agents administered in combination may be administered via different routes of delivery and/or according to different schedules. Alternatively, or additionally, in some embodiments, one or more doses of a first active agent is administered substantially simultaneously with, and in some embodiments via a common route and/or as part of a single composition with, one or more other active agents.

Factors to be considered when optimizing routes and/or dosing schedule for a given therapeutic regimen may include, for example, the particular cancer being treated (e.g., type, stage, location, etc.), the clinical condition of a subject (e.g., age, overall health, weight, etc.), the site of delivery of the agent, the nature of the agent (e.g. an antibody or other protein-based compound), the mode and/or route of administration of the agent, the presence or absence of combination therapy, and other factors known to medical practitioners.

Those skilled in the art will appreciate, for example, that a specific route of delivery may impact dose amount and/or required dose amount may impact route of delivery. For example, where particularly high concentrations of an agent within a particular site or location (e.g., within a tissue or organ) are of interest, focused delivery (e.g., intratumoral delivery) may be desired and/or useful. In some embodiments, one or more features of a particular pharmaceutical composition and/or of a utilized dosing regimen may be modified over time (e.g., increasing or decreasing amount of active in any individual dose, increasing or decreasing time intervals between doses, etc.), for example in order to optimize a desired therapeutic effect or response (e.g., a therapeutic or biological response that is related to the functional features of an anti-CD38 antibody as described herein). In general, type, amount, and frequency of dosing of active agents in accordance with the present invention in governed by safety and efficacy requirements that apply when relevant agent(s) is/are administered to a mammal, preferably a human. In general, such features of dosing are selected to provide a particular, and typically detectable, therapeutic response as compared with what is observed absent therapy. In context of the present invention, an exemplary desirable therapeutic response may involve, but is not limited to, inhibition of and/or decreased tumor growth, tumor size, metastasis, one or more of the symptoms and side effects that are associated with the tumor, as well as increased apoptosis of cancer cells, therapeutically relevant decrease or increase of one or more cell marker or circulating markers and the like. Such criteria can be readily assessed by any of a variety of immunological, cytological, and other methods that are disclosed in the literature. For example, the therapeutically effective amount of anti-CD38 antibodies, alone or in combination with a further agent, can be determined as being sufficient to enhance killing of cancer cells as described in the Examples.

A therapeutically effective amount of an anti-CD38 antibody as active agent or composition comprising such agent can be readily determined using techniques available in the art including, for example, considering one or more factors such as the disease or condition being treated, the stage of the disease, the age and health and physical condition of the mammal being treated, the severity of the disease, the particular compound being administered, and the like.

In some embodiments, therapeutically effective amount is an effective dose (and/or a unit dose) of an active agent that may be at least about 0.01 μg/kg body weight, at least about 0.05 μg/kg body weight; at least about 0.1 μg/kg body weight, at least about 1 μg/kg body weight, at least about 5 μg/kg body weight, at least about 10 μg/kg body weight, at least about 15 μg/kg body weight, at least about 20 μg/kg body weight, at least about 25 μg/kg body weight or more (e.g. about 100 μg/kg body weight). In some embodiments, therapeutically effective amount is an effective dose (and/or a unit dose) of an active agent that may be at least about 0.01 mg/kg body weight, at least about 0.05 mg/kg body weight; at least about 0.1 mg/kg body weight, at least about 1 mg/kg body weight, at least about 5 mg/kg body weight, at least about 10 mg/kg body weight, at least about 15 mg/kg body weight, at least about 20 mg/kg body weight, at least about 25 mg/kg body weight or more (e.g. about 100 mg/kg body weight. It will be understood by one of skill in the art that in some embodiments such guidelines may be adjusted for the molecular weight of the active agent. The dosage may also be varied for route of administration, the cycle of treatment, or consequently to dose escalation protocol that can be used to determine the maximum tolerated dose and dose limiting toxicity (if any) in connection to the administration of the isolated antibody or antigen-binding fragment thereof comprising the aCD38-b-348 or aCD38-b-329 HCDR3 amino acid sequence at increasing doses.

Therapeutic compositions typically should be sterile and stable under the conditions of manufacture and storage. The composition can be formulated as a solution, microemulsion, dispersion, liposome, or other ordered structure suitable to high drug concentration. Sterile injectable solutions can be prepared by incorporating the antibody in the required amount in an appropriate solvent with one or a combination of ingredients enumerated above, followed by filtered sterilization. Generally, dispersions are prepared by incorporating the active compound into a sterile vehicle that contains a basic dispersion medium and other required ingredients from those enumerated above. In the case of powders for preparing sterile injectable solutions, the preferred methods of preparation are vacuum drying and freeze drying that yields a powder of the active ingredient plus any additional desired ingredient from a previously sterile filtered solution. The proper fluidity of a solution can be maintained, for example, by using a coating, by the maintenance of the required particle size in the case of dispersion and by the use of surfactants. Prolonged absorption of injectable compositions can be brought about by including in the composition an agent that delays absorption, for example, monostearate salts and gelatin.

The formulation of each agent should desirably be sterile, as can be accomplished by filtration through sterile filtration membranes, and then packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations as discussed herein. Sterile injectable formulations may be prepared using a non-toxic parenterally acceptable diluent or solvent, such as water or 1,3 butanediol. Other parentally-administrable formulations which are useful include those which comprise the active ingredient in microcrystalline form, in a liposomal preparation, or as a component of biodegradable polymer systems. Compositions for sustained release or implantation may comprise pharmaceutically acceptable polymeric or hydrophobic materials such as an emulsion, an ion exchange resin, a sparingly soluble polymer or salt.

Each pharmaceutical composition for use in accordance with the present invention may include pharmaceutically acceptable dispersing agents, wetting agents, suspending agents, isotonic agents, coatings, antibacterial and antifungal agents, carriers, excipients, salts, or stabilizers are non-toxic to the subjects at the dosages and concentrations employed. A non-exhaustive list of such additional pharmaceutically acceptable compounds includes buffers such as phosphate, citrate, and other organic acids; antioxidants including ascorbic acid and methionine; salts containing pharmacologically acceptable anions (such as acetate, benzoate, bicarbonate, bisulfate, isothionate, lactate, lactobionate, laurate, malate, maleate, salicylate, stearate, subacetate, succinate, tannate, tartrate, teoclate, tosylate, thiethiodode, and valerate salts); preservatives (such as octadecyidimethylbenzyl ammonium chloride; hexamethonium chloride; benzalkonium chloride, benzethonium chloride; sodium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

In some embodiments, where two or more active agents are utilized in accordance with the present invention, such agents can be administered simultaneously or sequentially. In some embodiments, administration of one agent is specifically timed relative to administration of another agent. In some embodiments, desired relative dosing regimens for agents administered in combination may be assessed or determined empirically, for example using ex vivo, in vivo and/or in vitro models; in some embodiments, such assessment or empirical determination is made in vivo, in a particular patient or patient population (e.g., so that a correlation is made).

In some embodiments, one or more active agents utilized in practice of the present invention is administered according to an intermittent dosing regimen comprising at least two cycles. Where two or more agents are administered in combination, and each by such an intermittent, cycling, regimen, individual doses of different agents may be inter-digitated with one another. In some embodiments, one or more doses of the second agent is administered a period of time after a dose of an anti-CD38 antibody as described herein. In some embodiments, each dose of the second agent is administered a period of time after a dose of an anti-CD38 antibody as described herein. In some embodiments, an anti-CD38 antibody as described herein can be also administered in regimens that involve not only subsequent administration by the same route but also by alternating administration routes such as by sub-cutaneous (or intramuscular) administration and intra-tumoral administration, within one or more cycles of treatments over one, two, four or more weeks, repeating such cycle with the same regimen (or by extending the interval between administrations), depending of patient responses. Also, in some embodiments, the precise regimen followed (e.g., number of doses, spacing of doses (e.g., relative to each other or to another event such as administration of another therapy), amount of doses, etc. may be different for one or more cycles as compared with one or more other cycles.

By using any of the routes of administrations, dosages, and/or regimens as described herein, an anti-CD38 antibody as described herein can be identified, characterized, and/or validated, for example, taking into account one or more criteria that are measured in the patients using biopsies, blood samples, and/or other clinical criteria. In some embodiments, as an alternative or in addition to direct evaluation of tumor size and/or metastasis, therapeutic efficacy of an anti-CD38 antibody as described herein can be determined in methods wherein one or more different general criteria are evaluated: direct cytotoxicity on cancer cells (apoptosis and necrosis of cancer cells), increase of tumor infiltrating, immune cells (such as CD4-positive and/or CD8-positive tumor infiltrating T cells), increase in immune cells that circulates in blood (total populations or specific sub-populations of lymphocytes, NK cells, monocytes, dendritic cells, macrophages, B cells, etc.), and/or presenting some differential expression pre-versus post-treatment only in either responding or non-responding patients (as determined by RNA sequencing, mass flow cytometry, and/or other mass sequencing approach). Alternatively or additionally, in some embodiments, such identification, characterization, and/or validation may involve the follow-up at molecular level by screening the mRNA and/or protein expression of one or more specific proteins or sets of proteins. In some embodiments, one or more such techniques may allow identification or relevant information for evaluating the response to an anti-CD38 antibody as described herein, for example that may be is related to tissue distribution and/or markers for specific cell populations within (or nearby) the tumor and/or circulating in blood.

Such approaches and immune-biological data may allow determination not only of one or more efficacy and/or safety parameters or characteristics, but in some embodiments, can provide a rationale for choosing a particular dose, route or dosing regimen, for example that may be utilized in one or more clinical trials for a given indication, alone and/or in combination with other drugs, standard-of-care protocols, or immunotherapies that can provide further therapeutic benefits. Thus, in a series of further embodiments of the invention, an anti-CD38 antibody as described herein is used in a method of treating a patient suffering from a disease (such as cancer) or preventing a disease (such as cancer) after determining the combined presence (and/or absence) of expression at RNA and/or protein level for one or more genes in cells or tissues of the patient (such as a tumor, a blood sample, or a blood fraction), post- or pre-treatment with such a formulation. Such methods may allow therefore defining a one or more biomarkers, or a more complex gene expression signature (or cell population distribution) that is associated to the therapeutically effective amount of a desirable anti-CD38 antibody, the therapeutically relevant biomarker(s) that predicts that a subject may have an anti-tumor or anti-infective response after the treatment with an anti-CD38 antibody as described herein, or the therapeutically relevant biomarker(s) that predicts that a subject may respond to the treatment with a compound after the treatment with an anti-CD38 antibody.

Alternatively or additionally, in some embodiments, dosing and administration for a particular anti-CD38 antibody as disclosed herein can be preliminarily established and/or later evaluated in view of CD38 expression in human cancers and/or other human tissues, for example by gathering data about CD38 distribution in stromal and/or immune subsets in various cancers, tissues and/or patients. Such data can be generated by using common technologies (such as flow cytometry, mass cytometry, immunohistochemistry or mRNA expression libraries) across common cancer types and/or tissues (central nervous system, Esophagus, Stomach, Liver, Colon, Rectum, Lung, Bladder, Heart, Kidney, Thyroid, Pancreas, Uterus, Skin, Breast, Ovary, Prostate and testis) for identifying relationship between CD38 expression in various immune and non-immune subpopulations and/or its relation with cell infiltrate measures and/or cancer-relevant markers associated with sub-sets of cancer cells or immune cells (such as Foxp3 and PD-1/PD-L1). CD38 expression can be confined (or not) to immune subsets in tumor tissue (such as in NK cells and other effector or regulatory immune cells), and correlations between CD38 expression and immune checkpoint inhibitors can be determined if being positive, thus suggesting appropriate uses of anti-CD38 antibodies in combinations with compounds targeting such immune checkpoint inhibitors.

Dosing Regimen:

As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length. Alternatively, a dosing regimen comprises a plurality of doses and at least two different time periods separating individual doses. In some embodiments, all doses within a dosing regimen are of the same unit dose amount. Alternatively, different doses within a dosing regimen are of different amounts. In some embodiments, a dosing regimen comprises a first dose in a first dose amount, followed by one or more additional doses in a second dose amount different from the first dose amount. A dosing regimen may comprise a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Epitope:

As used herein, the term "epitope" refers to a portion of an antigen that is bound by an antibody or antigen-binding fragment. In some embodiments, where the antigen is a polypeptide, an epitope is conformational in that it is comprised of portions of an antigen that are not covalently contiguous in the antigen but that are near to one another in three-dimensional space when the antigen is in a relevant conformation. For example, for CD38, conformational epitopes are those comprised of amino acid residues that are not contiguous in CD38 extracellular domain; linear epitopes are those comprised of amino acid residues that are contiguous in CD38 extracellular domain. In some embodiments, epitopes utilized in accordance with the present invention are provided by means of reference to those bound by anti-CD38 antibodies disclosed herein (e.g., by aCD38-b-348 or aCD38-b-329 and defined as aCD38-b-ep). Means for determining the exact sequence and/or particularly amino acid residues of the epitope for aCD38-b-348 or aCD38-b-329 are known in the literature and in the Examples, including competition with peptides, from antigen sequences, binding to CD38 sequence from different species, truncated, and/or mutagenized (e.g. by alanine scanning or other site-directed mutagenesis), phage display-based screening, or (co-) crystallography techniques.

Indirect Antiglobulin Test (IAT):

As used herein, the term "indirect antiglobulin test" or "IAT" may refer to a method of testing for any patient-derived antibodies that specifically bind to red blood cell antigens expressed by donor red blood cells in a donor blood sample. The patient blood sample may comprise whole blood, plasma or serum. The donor blood sample may comprise whole blood or red blood cells. An indirect antiglobulin test may be performed using a column agglutination assay, a tube assay, or a solid phase assay. IAT may comprise the following steps. A red blood cell suspension may be incubated with a sample of plasma or serum from a patient, or a blood typing reagent or control. The red blood cell suspension may be obtained from a donor blood sample. Incubation may be performed at room temperature (from about 15° C. to about 25° C.). Alternatively, incubation may be performed at about 37° C. Incubation may be performed for a duration determined according to manufacturer's instructions. During the incubation step, if a patient-derived anti-red blood cell antigen antibody is present in the patient sample and the antigen to which it is specific is also present on the RBCs, binding of the patient-derived antibody to the red blood cell antigen may occur. The step of patient-derived antibody to red blood cell antigen binding may be referred to as sensitisation. Following sensitisation, wash steps may be performed to separate unbound antibody in solution from the RBCs with bound antibodies. An agglutination agent such as an anti-human globulin reagent is added to the solution containing the RBCs and any bound antibodies (if present). The anti-human globulin reagent comprises anti-human IgG antibodies and may further comprise anti-C3. Any anti-human globulin reagent may be used in the present invention. If patient-derived antibodies are bound to the RBCs, the anti-human globulin reagent will bind to the patient-derived antibodies on the RBCs and cause agglutination of the RBCs. A separation step may be included to separate agglutinated RBCs from the rest of the solution. The separation step may comprise centrifugation. Centrifugation may be performed for a speed and duration determined according to the specific equipment used, or any conditions sufficient to separate agglutinated RBCs from the rest of the solution. Under normal testing conditions, an agglutination reaction on an IAT test is indicative of the presence of patient-derived antibodies against RBC antigens (clinically significant antibodies) in the patient's sample. Under normal testing conditions, an agglutination reaction on an IAT test is indicative of an incompatible match between donor RBCs and patient serum/and or plasma. Haemolysis (destruction of red blood cells) may also be observed on an IAT test and is also indicative of an incompatible match between donor RBCs and patient serum/and or plasma. When a patient has been treated with daratumumab or isatuximab, agglutination of RBCs may occur on an IAT test irrespective of whether the patient's sample contains alloantibodies against any RBC antigens, since the anti-human globulin causes the anti-CD38 antibodies daratumumab or isatuximab to agglutinate, in turn causing agglutination of the red blood cells to which the anti-CD38 antibodies are bound, which can be detected visually (by eye). The methods of the present invention are characterised in that when the patient sample comprises an anti-CD38 antibody or antigen binding fragment thereof described herein (i.e. not daratumumab or isatuximab), the presence of the anti-CD38 antibody surprisingly does not cause RBC agglutination on an IAT test. This is the case even then the anti-CD38 antibody is, for example, an IgG antibody and the anti-human globulin comprises anti-human IgG.

Interference:

As used herein, the term "interference" may refer to any type of false-positive or false-negative result obtained on blood antibody screening or blood crossmatching. For example, interference may refer to the occurrence of an agglutination reaction in an IAT test in the absence of any clinically significant alloantibodies in a patient sample. Interference may falsely indicate incompatibility between patient serum or plasma and donor RBCs. Interference may falsely indicate the presence of alloantibodies in a patient serum or plasma sample that specifically bind donor RBC antigens. For example, most anti-CD38 antibodies (e.g. daratumumab and isatuximab) are known to cause interference on blood antibody screening and blood crossmatching. When present in a patient's plasma or serum sample, daratumumab and/or isatuximab can bind to CD38 on donor RBCs when the patient and donor samples are mixed. When an anti-human globulin reagent is added to the mixture containing daratumumab or isatuximab (from the patient serum) bound to donor RBCs, agglutination occurs. Whilst agglutination usually indicates an incompatible match between patient and donor, where the patient has been treated with daratumumab or isatuximab agglutination may occur even when the patient blood sample contains no clinically significant antibodies e.g. no alloantibodies that bind any red blood cell antigens present on the donor RBCs. The anti-CD38 antibodies described herein (i.e. aCD38-b-348 and aCD38-b-329 and antibodies derived therefrom) do not cause interference on blood antibody screening or blood crossmatching. In some embodiments, the presence of an anti-CD38 antibody or antigen binding fragment thereof as described herein in a patient's serum or plasma sample causes less interference on blood antibody screening or blood crossmatching compared to daratumumab and/or compared to isatuximab. In some embodiments, the presence of an anti-CD38 antibody or antigen binding fragment thereof as described herein in a patient's serum or plasma sample causes less agglutination on blood antibody screening or blood crossmatching compared to daratumumab and/or compared to isatuximab. In some embodiments, treatment of a patient with anti-CD38 antibodies as described herein does not produce agglutination on blood antibody screening or blood crossmatching.

Isatuximab:

Isatuximab is a human monoclonal IgG1 anti-CD38 antibody. Isatuximab is known to cause interference (i.e. an agglutination reaction in the absence of clinically significant patient antibodies that specifically bind red blood cell antigens) on blood antibody screening and blood crossmatching. Isatuximab may comprise the following variable heavy and variable light chain sequences:

```
Heavy chain:
                                    (SEQ ID NO: 33)
QVQLVQSGAEVAKPGTSVKLSCKASGYTFTYWMQWVKQRPGQGLEWIGTI

YPGDGDTGYAQKFQGKATLTADKSSKTVYMHLSSLASEDSAVYYCARGDY

YGSNSLDYWGQGTSVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK

Light chain:
                                    (SEQ ID NO: 34)
DIVMTQSHLSMSTSLGDPVSITCKASQDVSTVVAWYQQKPGQSPRRLIYS

ASYRYIGVPDRFTGSGAGTDFTFTISSVQAEDLAVYYCQQHYSPPYTFGG

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

Patient:

As used herein, the term "patient" or "subject" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. A patient may display one or more symptoms of a disorder or condition, or may have been diagnosed with one or more disorders or conditions (such as cancer, or presence of one or more tumors). In some embodiments, the patient is receiving or has received certain therapy to diagnose and/or to treat such disease, disorder, or condition. In preferred embodiments, the patient is a human cancer patient, for example a multiple myeloma patient.

Percent (%) Sequence Identity:

Percent (%) "sequence identity" between two sequences can be determined using those methods known in the art. Sequence identity with respect to a peptide, polypeptide or antibody sequence can be defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, including gapped BLAST, and BLASTp (for proteins), (Altschul S F et al (1997)), or FASTA, using the default parameters.

Patient Antibody:

As used herein, the term "patient antibody" or "patient antibodies" used herein refers to antibodies made in vivo by the patient themselves. The patient antibodies are therefore patient-derived antibodies. The patient antibodies are therefore distinguished from the anti-CD38 antibodies, since these are therapeutic antibodies (exogenous antibodies administered to the patient as part of a treatment regimen, for example treatment for a CD38-expressing cancer). The patent antibodies may be alloantibodies or autoantibodies. Generally, the methods of the present invention determine the presence or absence of clinically significant patient antibodies in the patient blood sample. "Clinically significant" refers to the ability of the patient antibodies to react to donor red blood cells in a manner that causes an adverse reaction when the patient is administered the donor red blood cells. An adverse reaction may include destruction (haemolysis) of the donor red blood cells. An adverse reaction may include an acute or delayed haemolytic transfusion reaction, or haemolytic disease of the foetus and newborn (HDFN).

Usually, the patient-derived antibodies that specifically bind one or more red blood cell antigens are human IgG antibodies.

"Alloantibody" refers to an antibody that specifically binds a red blood cell antigen that is not present on the subject's own red blood cells. The alloantibodies are therefore anti-red blood cell antigen alloantibodies.

Alloantibodies are distinguishable from "autoantibodies", which refers to an antibody that specifically binds an antigen present on the subject's own red blood cells. Both alloantibodies and autoantibodies may be detected by the methods of the present invention. For an alloantibody to develop, an individual must be exposed to a non-self RBC antigen and have an HLA-binding motif capable of presenting a portion of the non-self antigen (Tormey & Hendrickson, 2019). Exposure to non-self antigens can occur through pregnancy, transfusion or transplantation. The process of forming an alloantibody is called "alloimmunisation". Alloantibodies may be clinically significant, leading to either destruction (haemolysis) of transfused RBCs or harm to a foetus or newborn, in the case of a mother carrying alloantibodies against an antigen on the baby's red blood cells. Indeed, alloimmunisation can be a direct cause of transfusion-associated mortality. Alloimmunisation also gives rise to further complications in patient treatment, such as transfusion delays, difficulties in locating compatible blood for highly alloimmunised individuals, and delayed or acute haemolytic transfusion reactions. Alloimmunisation is of particular clinical importance for oncology patients, who receive frequent blood transfusions as part of their supportive care and are at greater risk of developing alloantibodies (Hendrickson & Tormey, 2016). As such, it is important that patient samples can be screened for the presence of alloantibodies accurately and quickly. Patients treated with anti-CD38 antibodies, such as daratumumab or isatuximab, may experiences delays on screening for alloantibodies due to the presence of the anti-CD38 antibody in their serum, which binds to CD38 on RBCs and gives the false indication that alloantibodies are present. Antibody screening tests and blood crossmatching, which are used to detect alloantibodies, can be modified to incorporate steps to avoid this interference by anti-CD38 antibodies. For example, RBCs may be treated with an antigen-stripping agent (such as DTT) or the patient sample may be treated with an anti-CD38 neutralising agent (such as soluble CD38). However, such additional reagents result in additional cost and are not widely available, and the extra method steps are time-consuming and introduce delay to antibody screening. The methods of the present invention enable the detection of alloantibodies in a patient sample without the requirement for additional processing of RBCs or patient blood samples. Using the methods of the present invention, the anti-CD38 antibody or antigen binding fragment thereof does not result in interference (for example, agglutination in the absence of clinically significant alloantibodies) on antibody screening or crossmatching, thereby minimising cost and avoiding delay in identifying compatible blood products for transfusion.

The patient antibodies (for example patient alloantibodies) do not specifically bind CD38.

Pharmaceutically Acceptable:

As used herein, the term "pharmaceutically acceptable" applied to the carrier, diluent, or excipient used to formulate a composition as disclosed herein means that the carrier, diluent, or excipient must be compatible with the other ingredients of the composition and not deleterious to the recipient thereof.

Pharmaceutical Composition:

As used herein, the term "pharmaceutical composition" refers to a composition in which an active agent is formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. A pharmaceutical compositions may be formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous, intratumoral, or epidural injection as a sterile solution or suspension, or sustained-release formulation; topical application, for example, as a cream, ointment, or a controlled-release patch or spray applied to skin, lungs, or oral cavity; intravaginally, intrarectally, sublingually, ocularly, transdermally, nasally, pulmonary, and to other mucosal surfaces.

Plasma:

As used herein, the term "plasma" refers to a liquid component of blood that is largely devoid of red and white blood cells and platelets. Plasma may contain fibrinogen and other clotting factors, as well as albumin. Plasma for use in the invention may be prepared from whole blood using any suitable or standard preparation protocol. In the present invention, plasma may be provided by, or derived from, a patient who is to receive a blood transfusion. In order to prepare plasma for use, whole blood may be collected into anticoagulant-treated tubes. Red blood cells and platelets are removed or separated by centrifugation and the resulting supernatant is designated plasma. A plasma sample for use in this invention may comprise, for example, a volume of about 10 µl to about 3 ml. For example, about 100 µl, 150 µl, 160 µl, 200 µl, 250 µl or 300 µl of plasma may be used. Plasma and/or serum for use in the methods of this invention may be diluted with a suitable buffer or diluent prior to use. Plasma and/or serum may be prepared for use as a 1:1, 1:2, 1:3, 1:4, 1:5, 1:6, 1:7, 1:8, 1:9 or 1:10 dilution. Suitable diluents may include, for example, phosphate buffered saline (PBS) and/or low ionic strength solution (LISS).

Red Blood Cells:

The terms "red blood cells", "RBCs" or "erythrocytes" as used herein refer to blood cells capable of transporting oxygen. Red blood cells for use in the invention, i.e. donor red blood cells, may be derived from any suitable source of whole blood using any suitable or standard preparation protocol. In the present invention, the red blood cells may be obtained from a source of donor blood which is intended for use, for example for use in transfusion to a patient. Donor red blood cells are therefore generally from a human donor. Donor blood may be collected and stored in flexible plastic bags. The bags may contain compounds and chemicals (for example sodium citrate, phosphate, dextrose, and sometimes adenine) which prevent the blood from clotting and facilitate storage. The tubing through which blood passes into the storage bag may be segmented after collection to provide "pigtail" sections which contain small volumes of blood. These small "pigtail" volumes of donor blood are suitable for use in crossmatching assays, including the assays of this invention. Small volumes of whole blood may be provided as a source of red blood cells for use in the assays of this invention. For example, about 1 ul to about 500 ul of donor red blood cells may be used. The methods of the invention may use about 10 µl, about 20 µl, about 30 µl, about 40 µl, about 50 µl, about 60 µl, about 70 µl, about 80 µl, about 90 µl about 100 µl, about 150 µl or about 200 µl (for example from about 10 µl to about 200 µl) of whole donor blood. Prior to use, the red blood cells may be diluted with any suitable diluent or buffer. The methods of this invention may use about about 10 µl, about 20 µl, about 30 µl, about 40 µl, about 50 µl, about 60 µl, about 70 µl, about 80 µl, about 90 µl, about 100 µl, about 150 µl or about 200 µl (for example from about 10 µl to about 200 µl) of donor red blood cells prepared in a suitable diluent or buffer.

Serum:

As used herein, the term "serum" refers to a liquid component of blood which is largely devoid of clotting factors, platelets and blood cells. Serum for use in the invention may be prepared from whole blood using any suitable or standard preparation protocol. In the present invention, serum may be provided by, or derived from, a patient who is to receive a blood transfusion. To prepare serum for use, whole blood may be collected and allowed to clot for a period of time. Red blood cells and platelets may be removed by centrifugation and the resulting supernatant is designated serum. Plasma and/or serum for use in the methods of this invention may be diluted with a suitable buffer or diluent prior to use. Plasma and/or serum may be prepared for use as a 1:1, 1:2, 1:3, 1:4, 1:5, 1:6, 1:7, 1:8, 1:9 or 1:10 dilution. Suitable diluents may include, for example, phosphate buffered saline (PBS) and/or low ionic strength solution (LISS).

Solid Phase Assay:

As used herein, the terms "solid phase testing", "solid phase assay" or "solid phase method" refer to methods suitable for detection of patient-derived antibodies (such as alloantibodies, in particular clinically significant alloantibodies) that specifically bind red blood cell antigens in a patient sample, in particular in blood crossmatching or RBC panel antibody screening. Solid phase systems, such as the Immucor Capture-R Select, can be used in antibody screening to detect the presence of patient-derived antibodies. Solid phase testing may involve binding of RBCs to a solid surface, such as a microplate well. The RBCs are selected based on the known expression of red blood cell antigens against which patient-derived antibodies are commonly formed. The RBCs adhered to the solid surface are then incubated with a patient plasma or serum sample, followed by wash steps and the addition of indicator cells (for example, cells coated with anti-IgG). Where patient-derived antibodies from a patient sample has bound to the immobilised RBCs on the solid surface, the anti-IgG on the indicator cells will also bind to the patient antibody bound to the immobilised RBCs. The indicator cells may be red blood cells coated with an agglutination agent, such as anti-human globulin (for example anti-IgG and/or anti-C3). The presence of relevant patient-derived antibodies in the patient sample is indicated by a red colour diffusely coating the solid surface where the indicator RBCs have bound. A negative solid phase assay where no relevant patient-derived antibodies are detected in the patient sample is indicated by a pellet of indicator cells at the bottom of the well.

Solid phase testing can also be used for blood crossmatching (compatibility testing). In solid phase crossmatching, an agglutination agent, such as anti-human globulin (e.g. anti-IgG and/or anti-C3) is attached or adhered directly to a solid surface. The serum or plasma from the patient and the donor RBCs to be tested are incubated together and contacted to the solid surface with the agglutination agent attached. Any antibodies from the patient sample that are bound to the donor RBCs will adhere to the agglutination agent on the solid surface. Thus, a diffuse red colour coating the solid surface of a well indicates an incompatible match between patient and donor due to the presence of patient-derived antibodies in the patient sample that specifically bind antigens on the donor RBCs.

Solid Tumor:

As used herein, the term "solid tumor" refers to an abnormal mass of tissue that usually does not contain cysts or liquid areas. Solid tumors may be benign or malignant. Different types of solid tumors are named for the type of cells that form them. Examples of solid tumors are sarcomas (including cancers arising from transformed cells of mesenchymal origin in tissues such as cancellous bone, cartilage, fat, muscle, vascular, hematopoietic, or fibrous connective tissues), carcinomas (including tumors arising from epithelial cells), melanomas, lymphomas, mesothelioma, neuroblastoma, retinoblastoma, etc. Cancers involving solid tumors include, without limitations, brain cancer, lung cancer, stomach cancer, duodenal cancer, esophagus cancer, breast cancer, colon and rectal cancer, renal cancer, bladder cancer, kidney cancer, pancreatic cancer, prostate cancer, ovarian cancer, melanoma, mouth cancer, sarcoma, eye cancer, thyroid cancer, urethral cancer, vaginal cancer, neck cancer, lymphoma, and the like.

Therapeutically Effective Amount:

As used herein, the term "therapeutically effective amount" means an amount (e.g., of an agent or of a pharmaceutical composition) that is sufficient, when administered to a population suffering from or susceptible to a disease and/or condition in accordance with a therapeutic dosing regimen, to treat such disease and/or condition. A therapeutically effective amount is one that reduces the incidence and/or severity of, stabilizes, and/or delays onset of, one or more symptoms of the disease, disorder, and/or condition. Those of ordinary skill in the art will appreciate that a "therapeutically effective amount" does not in fact require successful treatment be achieved in a particular subject.

Treatment:

As used herein, the term "treatment" (also "treat" or "treating") refers to any administration of a substance (e.g., disclosed anti-CD38 antibodies, as exemplified by aCD38-b-348 or aCD38-b-329, or any other agent) that partially or completely alleviates, ameliorates, relives, inhibits, delays onset of, reduces severity of, and/or reduces incidence of one or more symptoms. In some embodiments, treatment may involve the direct administration of an anti-CD38 antibody such as aCD38-b-348 or aCD38-b-329 (for example, as an injectable, aqueous composition, optionally comprising a pharmaceutically acceptable carrier, excipient and/or adjuvant, for use for intravenous, subcutaneous, intratumoral or peritumoral injection) or the administration using a regimen comprising obtaining cells from the subject (e.g. from the blood, a tissue, or a tumor, with or without a selection on the basis of presence, or absence, of the expression of a marker), contacting said cells with an anti-CD38 antibody such as aCD38-b-348 or aCD38-b-329 ex vivo, and administering such cells to the subject (with or without a selection on the basis of presence, or absence, of the expression of a marker).

Tube Assay:

As used herein, the terms "tube assay" or "tube method" refer to a method of performing an indirect antiglobulin test (IAT) in a tube, such as a test tube. Tube assays can be used to detect patient-derived antibodies (such as alloantibodies, in particular clinically significant alloantibodies) that specifically bind red blood cell antigens in a patient sample, such as a serum or plasma sample, as part of an antibody screen against an RBC panel or a crossmatch with donor RBCs. Tube assays commonly include the following steps. RBCs may be suspended in a suitable solution, for example, isotonic saline (NISS), phosphate-buffered saline (PBS), polyethylene glycol (PEG) solution or low ionic strength saline (LISS). The patient sample, for example a serum or plasma sample, may be added to a tube, followed by the RBC suspension. The patient sample and RBC suspension may be incubated under conditions sufficient to allow binding of any patient antibodies to any RBC antigens expressed on donor RBCs. For example, incubation may occur for at least about 5 minutes. Incubation may be performed for at least about 5 minutes, at least about 10 minutes, at least about 15 minutes, at least about 20 minutes, at least about 30 minutes, at least about 40 minutes, at least about 50 minutes, at least about 1 hour, at least about 90 minutes or at least about 2 hours. The duration of incubation may vary according to the reagents used, for example, use of LISS may lead to shorter reaction times and require shorter durations of incubation. Incubation may occur at about 37° C. Incubation may occur at about room temperature (from about 15° C. to about 25° C.). After incubation, washing steps may be performed to remove unbound patient antibodies. A tube assay may further comprise a step of adding an agent that specifically binds together any patient-derived antibodies present in the patient blood sample. The agent that specifically binds together any antibodies present in the patient blood sample may be an anti-globulin, for example anti-human IgG (and/or anti-C3). Where patient-derived antibodies are bound to RBC antigens on donor RBCs, the anti-globulin reagent binds together the patient-derived antibodies to cause agglutination of the RBCs bound to the patient antibodies. Agglutination of RBCs in a tube assay indicates the presence of patient-derived antibodies that specifically bind RBC antigens on the donor RBCs. Agglutination of RBCs in a tube assay may indicate the donor RBCs are incompatible with the patient.

Method of Screening

In a first aspect of the invention, there is provided a method of screening a blood sample obtained from a patient, wherein the patient has been administered an anti-CD38 antibody or antigen binding fragment thereof, the method comprising:
 a) providing a blood sample from the patient;
 b) providing a blood sample from a donor, wherein the donor blood sample comprises donor red blood cells; and
 c) screening the patient blood sample, comprising determining the presence or absence of one or more patient antibodies in the patient blood sample that specifically bind to one or more red blood cell antigens expressed on the surface of the donor red blood cells.

Advantageously, the methods of the present invention generally do not comprise a step of contacting the patient blood sample or the donor blood sample with an agent that inhibits binding of the anti-CD38 antibody or antigen binding fragment thereof to membrane-bound CD38 that may be present on the surface of (i.e. expressed by) the donor red blood cells. In methods of the prior art, in particular in methods of screening blood from patients to whom anti-CD38 antibodies (other than the anti-CD38 antibodies disclosed herein) have been administered, additional method steps are required to prevent the other therapeutic anti-CD38 antibodies from interfering with the screening of the patient sample for patient antibodies that may bind to red blood cell antigens expressed on the surface of donor red blood cells. In particular, a step of adding an agent that inhibits binding of the anti-CD38 antibody or antigen binding fragment thereof to membrane-bound CD38 present on the surface of the donor red blood cells is required to prevent a false positive in the screening assay. The agent that inhibits binding of the anti-CD38 antibody or antigen binding fragment thereof to membrane-bound CD38 may be, for example, a soluble CD38 antigen, an anti-CD38 idiotype antibody, or an antigen-stripping agent.

The patient is generally a patient to whom no anti-CD38 antibodies (and optionally no anti-red blood cell antigen antibodies) have been administered for at least 6 months, and preferably at least 1 year, prior to obtaining the blood sample from the patient, other than the anti-CD38 antibodies that do not interfere with the screening assay, such as the anti-CD38 antibodies disclosed herein (notably the aCD38-b-348 or the aCD38-b-329 antibodies, or antibodies or antigen binding fragments derived therefrom). Antibodies that are derived from aCD38-b-348 or aCD38-b-329 include antibodies that comprise at least one but preferably all 6 of the CDRs of aCD38-b-348 or aCD38-b-329 or any of their variant aCD38-b-348-m1, aCD38-b-348-m2-, aCD38-b-348-m3, aCD38-b-348-m5, aCD38-b-329-m6, or aCD38-b-329-m7, or any anti-CD38 antibodies that bind the same epitopes as aCD38-b-348 or aCD38-b-329. In some embodiments, the patient is a patient to whom daratumumab or isatuximab has not been administered for at 6 months, and preferably at least 1 year, prior to obtaining the blood sample from the patient. Of course, the patient may have never been administered any anti-CD38 antibody (and optionally no anti-red blood cell antigen antibodies) other than the anti-CD38 antibodies that do not interfere with the screening assay, such as the anti-CD38 antibodies disclosed herein, in particular if the anti-CD38 antibodies disclosed here are the first anti-CD38 antibody treatment (or anti-red blood cell antigen antibody treatment) the patient has received in their lifetime.

In some embodiments, the screening of step (b) is performed using an assay selected from the group consisting of a column agglutination assay, an indirect antiglobulin test (IAT) tube assay, and a solid phase assay. These are described in more detail elsewhere.

In some embodiments, the method comprises, prior to the screening of step (b), contacting the patient blood sample with the donor red blood cells from the donor blood sample to provide a patient blood/donor red blood cell mixture. The method may then further comprise a step of incubating the patient blood/donor red blood cell mixture, for example under conditions sufficient to enable any one or more patient antibodies in the patient blood sample, if present, to bind to one or more red blood cell antigens present on the donor red blood cells, to form one or more patient antibody/donor red blood cell antigen complexes. Optionally, the methods may further comprise a step of separating, if present, the any one or more patient antibody/donor red blood cell antigen complexes from the patient blood/donor red blood cell mixture, for example by centrifuging the patient blood/donor red blood cell mixture. A "separation step" (for example a centrifugation step) may still take place after the patient sample and donor red blood cells are mixed, even if no patient antibody/donor red blood cell antigen complexes form (e.g. because the patient blood sample did not comprise any patient antibodies that specifically bind any RBC antigens on the donor RBCs). However, this might not be apparent until after the separation step (e.g. centrifugation) takes place.

The Anti-CD38 Antibody or Antigen Binding Fragment Thereof

The anti-CD38 antibody or antigen binding fragment thereof is one that does not cause interference when crossmatching a patient blood sample with donor red blood cells or when performing any antibody RBC panel assay. The anti-CD38 antibody or antigen binding fragment thereof is not daratumumab or isatuximab.

In some embodiments, the anti-CD38 antibody or antigen-binding fragment thereof may be aCD38-b-348 or a-CD38-b-329 or may be derived from said antibodies. For example, in some embodiments, the anti-CD38 antibody or antigen-binding fragment thereof comprises the amino acid sequence of SEQ ID NO: 3 or SEQ ID NO: 19 as a variable heavy chain complementarity determining region 3 (HCDR3). In some embodiments, the anti-CD38 antibody or antigen-binding fragment may be further comprise amino acid sequence elements such as:
  a) the amino acid sequence of SEQ ID NO: 1 or SEQ ID NO: 17 as a variable heavy chain complementarity determining region 1 (HCDR1); and/or
  b) the amino acid sequence of SEQ ID NO: 2 or SEQ ID NO: 18 as a variable heavy chain complementarity determining region 2 (HCDR2).

In some embodiments, the anti-CD38 antibody or antigen-binding fragment thereof may further comprise:
  a) the amino acid sequence of SEQ ID NO: 4 or SEQ ID NO: 20 as a variable light chain complementarity determining region 1 (LCDR1);
  b) the amino acid sequence of SEQ ID NO: 5 or SEQ ID NO: 21 as a variable light chain complementarity determining region 2 (LCDR2); and
  c) an amino acid sequence selected from the group consisting of SEQ ID NO: 6, SEQ ID NO: 22, SEQ ID NO: 9, SEQ ID NO: 10, SEQ ID NO: 11, SEQ ID NO: 12, SEQ ID NO: 25 and SEQ ID NO: 26 as a variable light chain complementarity determining region 3 (LCDR3).

In some embodiments, the anti-CD38 antibody or antigen-binding fragment thereof comprises a variable heavy chain comprising the amino acid sequence of SEQ ID NO: 7 or SEQ ID NO: 23. Preferably, the anti-CD38 antibody or antigen-binding fragment thereof further comprises a variable light chain comprising an amino acid sequence selected from the group consisting of SEQ ID NO: 8, SEQ ID NO: 24, SEQ ID NO: 13, SEQ ID NO: 14, SEQ ID NO: 15, SEQ ID NO: 16, SEQ ID NO: 27 and SEQ ID NO: 28.

Variant antibodies antigen binding fragments thereof, such as variants having certain percent identities and/or one or more amino acid substitutions may also be used, as discussed in more detail below.

Certain Features of the Anti-CD38 Antibodies

In some embodiments, the anti-CD38 antibodies or antigen binding fragments modulate one or more features of CD38. That is, in some embodiments, level and/or activity of CD38, and/or one or more downstream effects thereof, is detectably altered when a provided antibody is present as compared with when it is absent. Alternatively or additionally, in some embodiments, level and/or activity of CD38, and/or one or more downstream effects thereof, when a provided antibody is present, is comparable to or greater than that observed under comparable conditions when a reference anti-CD-38 antibody (such as IB-4, with a known desirable attribute; e.g., a known ability to agonize one or more features of CD38).

In many embodiments, one or more features of CD38 is enhanced when an anti-CD38 antibody or antigen-binding fragment thereof used in the invention is present. For example, in some embodiments, presence of a the anti-CD38 antibody or antigen-binding fragment thereof correlates with increased immune cell activation, and/or proliferation. Thus, the anti-CD38 antibodies are often referred to herein as "agonists". Those skilled in the art, however, will appreciate that teachings of the present disclosure are not limited by particular mechanism of action of provided antibodies or antigen-binding fragments thereof. Relevant structural and/or functional features of provided antibodies are described herein and speak for themselves.

In some embodiments, the anti-CD38 antibodies or antigen-binding fragments thereof may be characterized, for example, by effects on certain immune effector cells (e.g., NK cells and/or T cells). Alternatively or additionally, in some embodiments, the anti-CD38 antibodies or antigen-binding fragments thereof may be characterized, for example, by effects on immune suppressive cells. For example, in some embodiments, the anti-CD38 antibodies or antigen-binding fragments thereof display activating properties with respect to immune effector cells such as NK cells and T cells and cytotoxic properties towards CD38 high expressing cells such as immune suppressive cells. Alternatively or additionally, in some embodiments, the anti-CD38 antibodies or antigen-binding fragments thereof are characterized by one or more features that are associated with binding to a specific epitope in human CD38 extracellular domain and/or that render them particularly amenable to pharmaceutical use and/or manufacturing. In particular, the anti-CD38 antibodies are particularly useful in methods of blood screening including crossmatching between a patient and an RBC donor, including in those patients undergoing therapy for certain disease that may require RBC transfusion (including cancer patients, in particular multiple myeloma patients).

In some embodiments, provided antibodies or antigen-binding fragments thereof bind to human CD38 with a Kd of in the $10^{-8}$ M range, or below (in the $10^{-9}$ M range), preferably the antibodies or antigen-binding fragments thereof bind to human CD38 with a Kd in the $10^{-8}$ M to $10^{-11}$ M range. In some embodiments the Kd is from about $10^{-8}$ to about $10^{-11}$. In some embodiments the Kd is from $10^{-8}$ to $10^{-9}$. In some embodiments, provided antibodies or antigen-binding fragments thereof may also bind to human and Cynomolgus Monkey CD38 (e.g., to an extracellular epitope on human and Cynomolgus Monkey CD38) with Kd value in the range of $10^{-8}$ to $10^{-11}$ M. The Kd to evaluate the binding affinity of the antibodies or antigen binding fragments thereof can be obtained by standard methodologies including surface plasmon resonance (SPR) such as Biacore analysis or analysis using Forte Bio Octet Systems.

Antibodies (and/or antigen-binding fragments thereof) used herein may be particularly useful in medicine (e.g., in therapy and/or in prophylaxis, for example in the treatment of cancer), and/or for use with respect to methods that require or involve targeting an epitope such as the one identified as aCD38-b-ep within human CD38 extracellular domain. Provided antibodies or antigen-binding fragments thereof may be prepared as presenting the most appropriate isotype, in particular human isotype from the group consisting of IgG1, IgG2, IgG3, and IgG4 isotype antibodies, more particularly human IgG1.

The antibodies may be provided in a variety of formats. For example, in some embodiments an appropriate format may be or comprise a monoclonal antibody, a domain antibody, a single chain antibody, a Fab fragment, a F(ab')2 fragment, a single chain variable fragment (scFv), a scFv-Fc fragment, a single chain antibody (scAb), an aptamer, or a nanobody. In some embodiments, an antibody or antigen-binding fragment thereof (and particularly a monoclonal antibody), may be a rabbit, mouse, chimeric, humanized or fully human antibody or antigen-binding fragment thereof. In some embodiments, a provided antibody or antigen-binding fragment thereof may be of an IgG, IgA, IgE, or IgM isotype (preferably human ones), as it can be most appropriate for a given use. In some embodiments, a provided antibody or antigen-binding fragment thereof is an IgG isotype, more particularly an IgG1, IgG2, IgG3, or IgG4 isotype (preferably human IgG1). In some embodiments, a provided antibody or antigen-binding fragment thereof is provided as part of a multi-specific binding agent such as, for example, when it is desirable to associate further binding and/or functional moieties, the isolated antibody or antigen-binding can be comprised in a bispecific antibody, a multi-specific antibody, or other multi-specific format that may be available in the art.

In some embodiments the antibody or antigen-binding fragment thereof (or variants of the same) may be a-fucosylated. It is well known that antibody glycosylation may have impact on the activity, pharmacokinetics and pharmacodynamics of antibodies (e.g., monoclonal antibodies, recombinant antibodies, and/or antibodies that are otherwise engineered or isolated) and Fc-fusion proteins and specific technology may be exploited to obtain an antibody with the desired glycosylation profile (Liu L, 2015). Effector functions supporting the cytotoxicity of an antibody for use in accordance with the present invention can be enhanced using methods to decrease antibody fucosylation levels. Antibodies comprising specific aCD38-b-348 or aCD38-b-329 sequence elements presenting such properties can be generated, for example, by expressing a aCD38-b-348 or aCD38-b-329 sequence using technologies for genetically engineering cell lines which may produce antibodies with absent or reduced fucosylation capacity, some of them commercially available such as Potelligent (Lonza) Gly-MAXX (ProBiogen), or by manipulating the manufacturing process, for example by controlling osmolarity and/or using enzyme inhibitors, see also for example the methods described in EP2480671.

The anti-CD38 antibodies or antigen binding fragments thereof used in present invention may be provided in the form of compositions (e.g. pharmaceutical compositions) comprising a provided antibody or an antigen-binding fragment thereof having desirable properties as described herein (for example, aCD38-b-348 or aCD38-b-329 antibodies or antigen-binding fragments thereof, and variants thereof or other antibodies derived therefrom). In some embodiments, such compositions are intended for and/or are used in a medical use, such as a therapeutic, diagnostic, or prophylactic use. In some embodiments, such a composition can further comprise a pharmaceutically acceptable carrier or excipient and/or may be for use in the treatment of cancer. In some embodiments, a pharmaceutical composition may be formulated with one or more carrier, excipients, salts, buffering agents, etc., as is known in the art. Those of skill in the art will be aware of and readily able to utilize a variety of formulation technologies, including as may be particularly desirable and/or useful for a given method and/or site of administration, for instance for parenteral (e.g. subcutaneous, intramuscular, or intravenous injection), mucosal, intratumoral, peritumoral, oral, or topical administration. In many embodiments, provided pharmaceutical compositions, comprising an anti-CD38 antibody or antigen binding portion thereof are formulated for parenteral delivery (e.g., by injection and/or infusion). In some embodiments, such a pharmaceutical composition may be provided, for example, in a pre-loaded syringe or vial format. In some embodiments, such a pharmaceutical composition may be provided and/or utilized, for example, in dry (e.g., lyophilized) form; alternatively, in some embodiments, such a pharmaceutical composition may be provided and/or utilized in a liquid form (e.g., as a solution, suspension, dispersion, emulsion, etc), in a gel form, etc.

Functional Features of the Anti-CD38 Antibodies

In some embodiments of the invention, the antibodies (and variants thereof as described herein, such as variants mutated to remove the DG motif) may have advantageous activity profiles. For example, in one embodiment, the antibodies or antigen-binding fragments thereof (and variants of the same) may:

exhibit antibody-dependent cell-mediated cytotoxicity (ADCC) activity against CD38+ target cells;
exhibit complement dependent cytotoxicity (CDC);
exhibit antibody-dependent cellular phagocytosis (ADCP); and/or
induce immune effector cell activation Preferably the aCD38-b-348 or aCD38-b-329 or antigen binding fragments thereof (or variants of the same) exhibit reduced CDC activity against a CD38+ target cell as compared to daratumumab and/or isatuximab under the same or substantially the same conditions.

Antibody-dependent cell-mediated cytotoxicity (ADCC) activity of the anti-CD38 antibodies or antigen-binding fragments thereof may be determined in vitro, e.g. using CD38+ Daudi cells as the target cell and human PBMC cells as effector cells, wherein the ratio of target cells to effector cells is from about 50 to 1 to about 25 to 1.

Complement dependent cytotoxicity (CDC) activity against a CD38+ target cell can be determined in vitro, e.g. using CD38+ Daudi and/or Raji cells in the presence of 10% complement. CDC activity may be determined by treating the target cells with increasing concentrations up to 10 µg/ml of antibodies in the presence of human complement. In some embodiments CDC activity may be determined by measuring the maximum percentage cell lysis of CD38+ cells, i.e. CD38+ Daudi cells in the presence of 10% complement. The maximum lysis for a given antibody may vary between experiments. It is therefore helpful to consider other metrics for measuring CDC activity, including, for example, EC50 values and/or fold difference in maximum % lysis and/or EC50 as compared with a reference antibody (such as daratumumab). A determination of a lower CDC activity as compared to daratumumab and/or isatuximab may therefore be in reference to maximum % lysis, EC50, and/or a fold change compared to daratumumab of either value.

In one preferred embodiment of the invention, the anti-CD38 antibodies may exhibit CDC:

a) with an EC50 that is at least 0.5-fold higher (or more preferably at least 1-fold higher) than daratumumab and/or isatuximab; or with a maximum % lysis as measured in Raji and/or b) Daudi cells in the presence of 10% complement that is no more than half that exhibited by daratumumab; for example in particular if the anti-CD38 antibody is aCD38-b-348 or an antibody derived therefrom or a variant thereof.

In one preferred embodiment of the invention, the CD38 Modulating Antibody Agents may exhibit may exhibit CDC:

a) with an EC50 that is at least 0.5-fold higher (or more preferably at least 1-fold higher) than daratumumab and/or isatuximab; or b) with a maximum % lysis as measured in Raji and/or Daudi cells in the presence of 10% complement that is no more than half that exhibited by daratumumab;

for example in particular if the anti-CD38 antibody is aCD38-b-329 or an antibody derived therefrom or a variant thereof.

Of course, the CDC of daratumumab and/or isatuximab is determined in the same or substantially the same conditions for the comparison. CDC activity can be determined using an antibody concentration of up to about 10 μg/mL. As the skilled person would understand, when determining maximum lysis of cells, a concentration of 10 μg/mL is not always required since maximum cell lysis may occur at a lower antibody concentration, although 10 μg/mL may be used if necessary.

In some embodiments, the reduction in CDC activity compared to daratumumab and/or isatuximab is such that the $EC_{50}$ of the antibody or antibody binding fragment thereof is at least about 0.5-fold greater (i.e. at least about 1.5 times greater), or preferably at least about 1-fold greater (i.e. at least about 2 times greater) than that of daratumumab under the same or substantially the same conditions. For example, the $EC_{50}$ of the antibody or antibody binding fragment thereof is at least about 0.5 fold greater, or preferably about 1-fold greater than that of daratumumab against Daudi cells and/or Raji in the presence of 10% complement.

In some embodiments, the antibody or antigen-binding fragment thereof (or variants of the same) induces CDC with an $EC_{50}$ of at least about 0.05 μg/mL against CD38+ Daudi and/or Raji cells (and optionally causes less than 60% lysis of such CD38+ expressing cells by CDC). In some embodiments, the antibody or fragment thereof induces CDC with an EC50 of at least about 0.05 μg/mL, at least about 0.10 μg/mL, or at least about 0.15 μg/mL against CD38+ Daudi and/or Raji cells (and optionally causes less than 60% lysis of such CD38+ expressing cells by CDC at an antibody concentration of up to about 10 μg/ml).

In some embodiments, the anti-CD38 antibody or antigen-binding fragment thereof (or variants of the same) may exhibit antibody-dependent cellular phagocytosis (ADCP) against CD38-expressing cells. ADCP activity may be determined by a reporter cell assay measuring FcgRIIa engagement in Jurkat cells as the effector cells expressing FcgRIIa. The effector cells also express NFAT-induced luciferase. The target cell in the assay may be a CD38 expressing Raji cell. NFAT signalling can be measured to determine the activity.

In some embodiments, the anti-CD38 antibody or antigen-binding fragment thereof (or variants of the same) may induce ADCP against in vitro generated T reg cells.

In some embodiments, the anti-CD38 antibody or antigen-binding fragment thereof (or variants of the same) may induce T cell activation at a greater amount as compared to daratumumab under the same or substantially the same conditions. In some embodiments T cell activation can be determined by measuring NFAT signalling in luc_reporter Jurkat cells. In some embodiments, the NFAT signalling induced by the anti-CD38 antibody or antigen-binding fragment thereof, as measured in luc_reporter Jurkat cells, is at least about 10% higher than that of daratumumab measured under the same or substantially the same conditions. In some embodiments, the NFAT signalling is at least about 15%, at least about 20%, or at least about 30% higher than NFAT signalling of daratumumab measured under the same or substantially the same conditions.

In a NFAT luc_reporter assay in Jurkat cells, NFAT signalling can be measured in the presence of soluble CD3 monoclonal antibody in relative luminescence units (RLU). The CD3 monoclonal antibody may be at a concentration of 1 μg/ml and the Jurkat cells may be stimulated with the anti-CD38 antibody at a concentration of from about 5 μg/ml to about 40 μg/ml (for example 10 μg/ml). Using such an assay, NFAT signalling may be at least about 30% higher than NFAT signalling of daratumumab measured under the same or substantially the same conditions, when the RLU of CD3 only stimulation is used as a baseline.

T cell activation can be further characterised by an increase in T cell proliferation, and/or an increase in cytokine secretion, wherein the cytokines may be selected from the group consisting of IL-2, TNF-α, IFN-γ, IL-10 and GM-CSF.

T cell proliferation can be measured as in the Examples, for example as determined at an antibody concentration of 10 μg/ml after 72 hours incubation and in the presence of 0.1 μg/ml or 0.5 μg/ml anti-CD3 antibody. In some embodiments, the anti-CD38 antibody or antigen-binding fragment thereof increases T cell proliferation of CD4+ and/or CD8+ cells by at least about 20% as compared to untreated cells. In some embodiments, T cell proliferation increases by at least about 25%, by at least about 30%, by at least about 35%, or by at least about 40% as compared to untreated cells.

Preferably the anti-CD38 antibody or antigen-binding fragment thereof (or variants of the same) increases T cell proliferation in CD4+ and/or CD8+ cells by at least about 0.5-fold (i.e. at least 1.5 times as much) or at least 1-fold (i.e. at least 2 times as much) or at least 2-fold (i.e. at least 3 times as much) or at least 3-fold (i.e. at least 4 times as much) as compared to cells treated with human IgG1 in the same or substantially the same conditions (for example incubation at the same antibody concentration for 72 hours).

In some embodiments, the anti-CD38 antibody or antigen-binding fragment thereof (or variants of the same) induces the secretion of a cytokine selected from the group consisting of IL-2, TNF-α, IFN-γ, IL-10 and/or GM-CSF in CD4+ and/or CD8+ cells in an amount greater than is induced by daratumumab under the same or substantially the same conditions. In some embodiments, the anti-CD38 antibody or antigen-binding fragment thereof increases the secretion of GM-CSF as compared to daratumumab. In some embodiments, the anti-CD38 antibody or antigen-binding fragment thereof increases the secretion of IL-2 as compared to a daratumumab. In some embodiments, the anti-CD38 antibody or antigen-binding fragment thereof increases the secretion of IL-2, TNF-α, IFN-γ, IL-10 and GM-CSF as compared to daratumumab. Cytokine secretion may be measured as provided in the Examples, for example as determined at an antibody concentration of 10 μg/ml after 72 hours incubation.

In some embodiments, the anti-CD38 antibody or antigen-binding fragment thereof (or variants of the same) may induce NK cell activation. NK cell activation can be characterised by an increase in NK cell proliferation. NK cell activation may alternatively or additionally be determined by an increase in showing intra-cellular IFNg production and/or as increased expression of the degranulation marker CD107a.

In some embodiments, the anti-CD38 antibody or antigen-binding fragment thereof (or variants of the same) may influence cyclase and/or NADase activity. The effect on the CD38 NADase activity can be measured, e.g. by measuring the conversion of E-NAD+ into 5'-eAMP in Jurkat cells. The effect on the CD38 cyclase activity can be measured, for example by measuring the conversion of NGD+ into cGDPR in Jurkat cells.

In some embodiments, the anti-CD38 antibody or antigen-binding fragment thereof (or variants of the same) has an inhibitory effect on CD38 cyclase activity. The inhibitory effect on the CD38 cyclase activity can be measured, for example by measuring the conversion of NGD+ into cGDPR in Jurkat cells. The inhibitory effect on CD38 cyclase activity can result in CD38 activity at least 10% lower compared to the CD38 cyclase activity in the presence of an IgG non-binding control antibody as measured by the conversion of NGD+ into cGDPR in Jurkat cells. In some embodiments, the anti-CD38 antibody or antigen-binding fragment thereof, has an inhibitory effect on CD38 cyclase which is less than the inhibitory effect of daratumumab on CD38 cyclase activity in the same or substantially the same conditions. In some embodiments, the anti-CD38 antibody or antigen-binding fragment thereof reduces the CD38 cyclase activity to no less than about 25% of the CD38 cyclase activity in the presence of an IgG non-binding control antibody as measured by the conversion of NGD+ into cGDPR in Jurkat cells. Preferably the antibody reduces the CD38 cyclase activity to no less than about 30%, to no less than about 40% or to no less than about 50% of the CD38 cyclase activity in the presence of an IgG non-binding control antibody. Preferably the antibody reduces the CD38 cyclase activity to between 25%-95%, between about 30%-90% or between about 50% to 90% of the CD38 cyclase activity in the presence of an IgG non-binding control antibody. This means that in the presence of the anti-CD38 antibody or antigen-binding fragment thereof, CD38 cyclase activity is still present in the Jurkat cells, however at a reduced amount as compared to in the presence of an IgG non-binding control antibody.

Daratumumab has been shown to inhibit cyclase activity and stimulate NADase activity. In contrast, the antibodies of the present invention may have an inhibitory effect on CD38 cyclase which is less than the inhibitory effect of daratumumab on CD38 cyclase activity in the same or substantially the same conditions.

As such the anti-CD38 antibodies or antigen-binding fragments thereof (or variants of the same) exhibit antibody-dependent cell-mediated cytotoxicity (ADCC) activity against CD38+ target cells; exhibit reduced CDC activity against a CD38+ target cell as compared to daratumumab and/or isatuximab under the same or substantially the same conditions (for example, the EC50 value as measured as described herein may be at least twice that of daratumumab); induce immune effector cell activation; induces T cell proliferation; induce an increase in cytokine secretion, including IL-2, IFNγ, TNFα, GM-CSF and IL-10; and induce NK cell activation. Such antibodies may also exhibit a slight inhibitory effect on CD38 cyclase activity.

Epitope

Given the selected anti-CD38 antibodies do not interfere with cross-matching, anti-CD38 antibodies binding particular epitopes of anti-CD38 may be particularly useful in the present invention.

In some embodiments, anti-CD38 antibody or antigen binding fragment thereof binds to an epitope on human CD38 that is bound by aCD38-b-348 or aCD38-b-329. In some embodiments, such anti-CD38 antibodies or antigen binding fragments thereof bind to the human CD38 extracellular domain. In some embodiments, the anti-CD38 antibodies may bind the epitope identified as aCD38-b-ep (protein sequence ARCVKYTEIHPEMRH (SEQ ID NO: 30); amino acids 65-79 in Uniprot sequence P28907 (SEQ ID NO: 29)).

In some embodiments, the anti-CD38 antibody specifically binds to an epitope of human CD38, wherein the epitope comprises one or more amino acid residues comprised in amino acids 65-79 of SEQ ID NO: 29. In some embodiments, the anti-CD38 antibody specifically binds to an epitope of human CD38, wherein the epitope comprises or consists of amino acids 65-79 of SEQ ID NO: 29. In some embodiments, the anti-CD38 antibody binds within the epitope of amino acids 65-79 of SEQ ID NO: 29. References to "within" herein with respect to any range include the extremities of the range. For example, in the present instance, "within the epitope of amino acids 65-79 of SEQ ID NO: 29" include the residues 65 and 79 and thus the epitope may include those residues.

Preferably the epitope comprises at least 5 amino acids, at least 6 amino acids, at least seven amino acids, at least eight amino acids, at least nine amino acids, at least ten amino acids, at least eleven amino acids, at least twelve amino acids, at least thirteen amino acids, or at least fourteen or more amino acids wherein the epitope comprises one or more amino acids comprised in amino acids 65-79 of SEQ ID NO: 29. The epitope may be either linear or conformational, i.e. discontinuous. In some embodiments, the anti-CD38 antibodies or antigen-binding fragments specifically bind to an epitope of human CD38 wherein the epitope comprises at least two, at least three, at least four, at least five, at least six, at least seven, at least eight, at least nine, at least ten, at least eleven, at least twelve, at least thirteen, or at least fourteen or more amino acid residues comprised in amino acids 65-79 of SEQ ID NO: 29.

In some embodiments, the anti-CD38 antibodies or antigen-binding fragments bind to an epitope comprising amino acids 65-79 of SEQ ID NO: 29.

In some embodiments, provided antibodies or antigen-binding fragments thereof bind to a mutant human CD38 (as compared to non-mutant human CD38 (SEQ ID NO: 29)), wherein in the mutant human CD38, the serine residue in position 274 has been substituted with a phenylalanine.

In some embodiments, provided antibodies or antigen-binding fragments thereof bind to a mutant human CD38 (as compared to non-mutant human CD38 (SEQ ID NO: 29)), wherein in the mutant human CD38, the aspartate residue in position 202 has been substituted with a glycine residue.

In some embodiments, provided antibodies or antigen-binding fragments thereof bind to a mutant human CD38 (as compared to non-mutant human CD38 (SEQ ID NO: 29)), wherein in the mutant human CD38, the serine residue in position 274 has been substituted with a phenylalanine and the aspartate residue in position 202 has been substituted with a glycine residue.

aCD38-b-348 and Antibodies and Antigen Binding Fragments Derived Therefrom

The anti-CD38 antibody may be the anti-CD38 antibody aCD38-b-348, for example the aCD38-b-348 antibody disclosed in WO2018224683. The aCD38-b-348 antibody is also known as CID-103. The anti-CD38 antibody may be any antibody or antigen-binding fragment thereof that is based on or is derived from such an antibody. Complementarity determining regions CDR1, CDR2, and CDR3 of the anti-CD38 antibody are determined according to the Kabat numbering scheme.

For example, in some embodiments, the anti-CD38 antibody or antigen-binding fragment thereof may comprise:
  a) the amino acid sequence of SEQ ID NO: 1 as a HCDR1;
  b) the amino acid sequence of SEQ ID NO: 2 as a HCDR2;
  c) the amino acid sequence of SEQ ID NO: 3 as a HCDR3;
  d) the amino acid sequence of SEQ ID NO: 4 as a LCDR1;
  e) the amino acid sequence of SEQ ID NO: 5 as a LCDR2; and
  f) the amino acid sequence of SEQ ID NO: 6 as a LCDR3 (as in aCD38-b-348).

In some embodiments, the anti-CD38 antibody or antigen-binding fragment thereof comprises a variable heavy chain comprising the amino acid sequence of SEQ ID NO: 7 and/or a variable light chain comprising the amino acid sequence of SEQ ID NO: 8 (as in aCD38-b-348).

In some embodiments the variable heavy chain sequence of the anti-CD38 antibody comprises the variable heavy chain sequence of aCD38-b-348, i.e.:

(SEQ ID NO: 7)
QLQLQESGPGLVKPSETLSLTCTVSGGSISSSDYYWGWIRQPPGKGLEWI

GSIYYSGSTYYNPSLKSRVTISVDTSKNQFSLKLSSVTAADTAVYYCARG

QYSSGWYAYPFDMWGQGTMVTVSS and the variable light chain sequence of the anti-CD38 antibody comprises the variable light chain sequence of a-CD38-b-348, i.e.:

(SEQ ID NO: 8)
EIVLTQSPGTLSLSPGERATLSCRASQSVRSSYLAWYQQKPGQAPRLLIY

GASSRATGIPDRFSGSGSGTDFTLTISRLEPEDFAVYYCQQDGNVYTFGG

GTKVEIK.

In some embodiments, the anti-CD38 antibody may be a variant of aCD38-b-348. Such variants may be the antibodies aCD38-b-348-m1, aCD38-b-348-m2, aCD38-b-348-m3 or aCD38-b-348-m4.

For example, in some embodiments, the anti-CD38 antibody or antigen-binding fragment thereof may comprise:
a) the amino acid sequence of SEQ ID NO: 1 as a HCDR1;
b) the amino acid sequence of SEQ ID NO: 2 as a HCDR2;
c) the amino acid sequence of SEQ ID NO: 3 as a HCDR3;
d) the amino acid sequence of SEQ ID NO: 4 as a LCDR1;
e) the amino acid sequence of SEQ ID NO: 5 as a LCDR2; and
f) the amino acid sequence of SEQ ID NO: 9 as a LCDR3 (as in aCD38-b-348-m1).

In some embodiments, the anti-CD38 antibody or antigen-binding fragment thereof may comprise:
a) the amino acid sequence of SEQ ID NO: 1 as a HCDR1;
b) the amino acid sequence of SEQ ID NO: 2 as a HCDR2;
c) the amino acid sequence of SEQ ID NO: 3 as a HCDR3;
d) the amino acid sequence of SEQ ID NO: 4 as a LCDR1;
e) the amino acid sequence of SEQ ID NO: 5 as a LCDR2; and
f) the amino acid sequence of SEQ ID NO: 10 as a LCDR3 (as in aCD38-b-348-m2).

In some embodiments, the anti-CD38 antibody or antigen-binding fragment thereof may comprise:
a) the amino acid sequence of SEQ ID NO: 1 as a HCDR1;
b) the amino acid sequence of SEQ ID NO: 2 as a HCDR2;
c) the amino acid sequence of SEQ ID NO: 3 as a HCDR3;
d) the amino acid sequence of SEQ ID NO: 4 as a LCDR1;
e) the amino acid sequence of SEQ ID NO: 5 as a LCDR2; and
f) the amino acid sequence of SEQ ID NO: 11 as a LCDR3 (as in aCD38-b-348-m3).

In some embodiments, the anti-CD38 antibody or antigen-binding fragment thereof may comprise:
a) the amino acid sequence of SEQ ID NO: 1 as a HCDR1;
b) the amino acid sequence of SEQ ID NO: 2 as a HCDR2;
c) the amino acid sequence of SEQ ID NO: 3 as a HCDR3;
d) the amino acid sequence of SEQ ID NO: 4 as a LCDR1;
e) the amino acid sequence of SEQ ID NO: 5 as a LCDR2; and
f) the amino acid sequence of SEQ ID NO: 12 as a LCDR3 (as in aCD38-b-348-m4).

In some embodiments, the anti-CD38 antibody or antigen-binding fragment thereof comprises:
a) a variable heavy chain comprising the amino acid sequence of SEQ ID NO: 7 and/or a variable light chain comprising the amino acid sequence of SEQ ID NO: 13 (as in aCD38-b-348-m1);
b) a variable heavy chain comprising the amino acid sequence of SEQ ID NO: 7 and/or a variable light chain comprising the amino acid sequence of SEQ ID NO: 14 (as in aCD38-b-348-m2);
c) a variable heavy chain comprising the amino acid sequence of SEQ ID NO: 7 and/or a variable light chain comprising the amino acid sequence of SEQ ID NO: 15 (as in aCD38-b-348-m3); or
d) a variable heavy chain comprising the amino acid sequence of SEQ ID NO: 7 and/or a variable light chain comprising the amino acid sequence of SEQ ID NO: 16 (as in aCD38-b-348-m4).

Accordingly the variant antibody aCD38-b-348-m1 may be characterised as comprising a heavy chain variable region comprising the sequence of:

(SEQ ID NO: 7)
QLQLQESGPGLVKPSETLSLTCTVSGGSISSSDYYWGWIRQPPGKGLEWI

GSIYYSGSTYYNPSLKSRVTISVDTSKNQFSLKLSSVTAADTAVYYCARG

QYSSGWYAYPFDMWGQGTMVTVSS and a variant light chain comprising the sequence:

(SEQ ID NO: 13)
EIVLTQSPGTLSLSPGERATLSCRASQSVRSSYLAWYQQKPGQAPRLLIY

GASSRATGIPDRFSGSGSGTDFTLTISRLEPEDFAVYYCQQEANVYTFGG

GTKVEIK.

The variant antibody aCD38-b-348-m2 may be characterised as comprising a heavy chain variable region comprising the sequence of:

(SEQ ID NO: 7)
QLQLQESGPGLVKPSETLSLTCTVSGGSISSSDYYWGWIRQPPGKGLEWI

GSIYYSGSTYYNPSLKSRVTISVDTSKNQFSLKLSSVTAADTAVYYCARG

QYSSGWYAYPFDMWGQGTMVTVSS.

and a variant light chain comprising the sequence:

(SEQ ID NO: 14)
EIVLTQSPGTLSLSPGERATLSCRASQSVRSSYLAWYQQKPGQAPRLLIY
GASSRATGIPDRFSGSGSGTDFTLTISRLEPEDFAVYYCQQDSNVYTFGG
GTKVEIK.

The variant antibody aCD38-b-348-m3 may be characterised as comprising a heavy chain variable region comprising the sequence of:

(SEQ ID NO: 7)
QLQLQESGPGLVKPSETLSLTCTVSGGSISSSDYYWGWIRQPPGKGLEWI
GSIYYSGSTYYNPSLKSRVTISVDTSKNQFSLKLSSVTAADTAVYYCARG
QYSSGWYAYPFDMWGQGTMVTVSS and a variant light chain comprising the sequence:

(SEQ ID NO: 15)
EIVLTQSPGTLSLSPGERATLSCRASQSVRSSYLAWYQQKPGQAPRLLIY
GASSRATGIPDRFSGSGSGTDFTLTISRLEPEDFAVYYCQQDANVYTFGG
GTKVEIK.

The variant antibody aCD38-b-348-m4 may be characterised as comprising a heavy chain variable region comprising the sequence of:

(SEQ ID NO: 7)
QLQLQESGPGLVKPSETLSLTCTVSGGSISSSDYYWGWIRQPPGKGLEWI
GSIYYSGSTYYNPSLKSRVTISVDTSKNQFSLKLSSVTAADTAVYYCARG
QYSSGWYAYPFDMWGQGTMVTVSS and a variant light chain comprising the sequence:

(SEQ ID NO: 16)
EIVLTQSPGTLSLSPGERATLSCRASQSVRSSYLAWYQQKPGQAPRLLIY
GASSRATGIPDRFSGSGSGTDFTLTISRLEPEDFAVYYCQQEGNVYTFGG
GTKVEIK.

The present invention may also use variant antibodies and antigen binding fragments thereof that have certain % identities relative to a reference sequence, such as the CDR sequences or the heavy and/or light chain variable sequences of aCD38-b-348.

For example, in some embodiments the anti-CD38 antibody or antigen binding fragment thereof comprises a variable heavy chain sequence comprising an amino acid sequence having at least 90% sequence identity to SEQ ID NO: 7. In some embodiments the anti-CD38 antibody or antigen binding fragment thereof comprises a variable heavy chain sequence comprising an amino acid sequence having at least 95% sequence identity to SEQ ID NO: 7. In some embodiments the anti-CD38 antibody or antigen binding fragment thereof comprises a variable heavy chain sequence comprising an amino acid sequence having at least 98% sequence identity to SEQ ID NO: 7. In some embodiments the anti-CD38 antibody or antigen binding fragment thereof comprises a variable heavy chain sequence comprising an amino acid sequence having at least 99% sequence identity to SEQ ID NO: 7. In some embodiments the anti-CD38 antibody or antigen binding fragment thereof comprises a variable heavy chain sequence comprising the amino acid sequence of SEQ ID NO: 7.

In some embodiments the anti-CD38 antibody or antigen binding fragment thereof comprises a variable light chain sequence comprising an amino acid sequence having at least 90% sequence identity to a sequence selected from the group consisting of SEQ ID NO: 8, 13, 14, 15 and 16. In some embodiments the anti-CD38 antibody or antigen binding fragment thereof comprises a variable light chain sequence comprising an amino acid sequence having at least 95% sequence identity to a sequence selected from the group consisting of SEQ ID NO: 8, 13, 14, 15 and 16. In some embodiments the anti-CD38 antibody or antigen binding fragment thereof comprises a variable light chain sequence comprising an amino acid sequence having at least 98% sequence identity to a sequence selected from the group consisting of SEQ ID NO: 8, 13, 14, 15 and 16. In some embodiments the anti-CD38 antibody or antigen binding fragment thereof comprises a variable heavy chain sequence comprising an amino acid sequence having at least 99% sequence identity to a sequence selected from the group consisting of SEQ ID NO: 8, 13, 14, 15 and 16. In some embodiments the anti-CD38 antibody or antigen binding fragment thereof comprises a variable light chain sequence identity to a sequence selected from the group consisting of SEQ ID NO: 8, 13, 14, 15 and 16.

In some embodiments the anti-CD38 antibody or antigen binding fragment thereof comprises a variable heavy chain sequence comprising an amino acid sequence having at least 90% sequence identity to SEQ ID NO: 7 and a variable light chain sequence comprising an amino acid sequence having at least 90% sequence identity to a sequence selected from the group consisting of SEQ ID NO: 8, 13, 14, 15 and 16. In some embodiments the anti-CD38 antibody or antigen binding fragment thereof comprises a variable heavy chain sequence comprising an amino acid sequence having at least 95% sequence identity to SEQ ID NO: 7 and a variable light chain sequence comprising an amino acid sequence having at least 95% sequence identity to a sequence selected from the group consisting of SEQ ID NO: 8, 13, 14, 15 and 16. In some embodiments the anti-CD38 antibody or antigen binding fragment thereof comprises a variable heavy chain sequence comprising an amino acid sequence having at least 98% sequence identity to SEQ ID NO: 7 and a variable light chain sequence comprising an amino acid sequence having at least 98% sequence identity to a sequence selected from the group consisting of SEQ ID NO: 8, 13, 14, 15 and 16. In some embodiments the anti-CD38 antibody or antigen binding fragment thereof comprises a variable heavy chain sequence comprising an amino acid sequence having at least 99% sequence identity to SEQ ID NO: 7 and a variable light chain sequence comprising an amino acid sequence having at least 99% sequence identity to a sequence selected from the group consisting of SEQ ID NO: 8, 13, 14, 15 and 16. In some embodiments the anti-CD38 antibody or antigen binding fragment thereof comprises a variable heavy chain sequence comprising the amino acid sequence of SEQ ID NO: 7 and a variable light chain sequence comprising an amino acid sequence selected from the group consisting of SEQ ID NO: 8, 13, 14, 15 and 16.

In some embodiments the anti-CD38 antibody or antigen binding fragment thereof comprises a variable heavy chain sequence comprising an amino acid sequence having at least 90% sequence identity to SEQ ID NO: 7 and a variable light chain sequence comprising an amino acid sequence having at least 90% sequence identity to SEQ ID NO: 8. In some embodiments the anti-CD38 antibody or antigen binding fragment thereof comprises a variable heavy chain sequence comprising an amino acid sequence having at least 95% sequence identity to SEQ ID NO: 7 and a variable light chain sequence comprising an amino acid sequence having at least 95% sequence identity to SEQ ID NO: 8. In some embodiments the anti-CD38 antibody or antigen binding fragment thereof comprises a variable heavy chain sequence comprising an amino acid sequence having at least 98% sequence identity to SEQ ID NO: 7 and a variable light chain sequence comprising an amino acid sequence having at least 98% sequence identity to SEQ ID NO: 8. In some embodiments the anti-CD38 antibody or antigen binding fragment thereof comprises a variable heavy chain sequence comprising an amino acid sequence having at least 99% sequence identity to SEQ ID NO: 7 and a variable light chain sequence comprising an amino acid sequence having at least 99% sequence identity to SEQ ID NO: 8. In some embodiments the anti-CD38 antibody or antigen binding fragment thereof comprises a variable heavy chain sequence comprising the amino acid sequence of SEQ ID NO: 7 and a variable light chain sequence comprising the amino acid sequence of SEQ ID NO: 8.

Such variant antibodies and antigen binding fragments thereof (i.e. ones having certain percent identities) may retain or exhibit the same (or substantially the same) functional and pharmacological properties as described for the antibodies and antigen binding fragments thereof having the heavy and light chain variable sequences disclosed herein for aCD38-b-348, for example binding to the same epitope as aCD38-b-348.

In some embodiments, in particular for any embodiments referencing sequences having a particular sequence identity to a reference sequence, the % sequence identity may be calculated without the sequence of all 6 CDRs of the specified heavy or light chain variable region. In such embodiments, the variations in sequence (if any) occur only in the framework regions.

In some embodiments, the anti-CD38 antibody may be an anti-CD38 antibody alternatively or additionally defined by a number of substitutions with respect to the aCD38-b-348 amino acid sequence elements defined above (or those of the variants m1 to m4).

For example, such an antibody may comprise, as variable heavy chain complementarity determining region 3 (HCDR3) a sequence containing up to 1, 2, 3, 4, 5, 6, 7, 8, 9, or 10, amino acid substitutions within aCD38-b-348-HCDR3 (SEQ ID NO: 3). In a further embodiment, the anti-CD38 antibody or antigen binding fragment thereof may comprise, as variable heavy chain complementarity determining regions 1, 2 and 3 (HCDR1, HCDR2, and HCDR3), sequences containing up to 1, 2, 3, 4, 5, 6, 7, 8, 9, or 10, amino acid substitutions within SEQ ID NO: 1, SEQ ID NO:2 and SEQ ID NO: 3 respectively and/or as variable light chain complementarity determining regions 1, 2 and 3 (LCDR1, LCDR2, and LCDR3), sequences containing up to 1, 2, 3, 4, 5, 6, 7, 8, 9, or 10, amino acid substitutions within SEQ ID NO: 4, SEQ ID NO: 5 and a sequence selected from the group consisting of SEQ ID NOs: 6, 9, 10, 11 and 12, respectively.

In a further embodiment, the anti-CD38 antibody or antigen binding fragment thereof may comprises, as a variable heavy chain sequence, up to 1, 2, 3, 4, 5, 6, 7, 8, 9, or 10 amino acid substitutions within SEQ ID NO: 7 and/or as a variable light chain sequence, up to 1, 2, 3, 4, 5, 6, 7, 8, 9, or 10 amino acid substitutions within a sequence selected from the group consisting of SEQ ID NOs: 8, 13, 14, 15 and 16. In some embodiments, the anti-CD38 antibody may comprise as a variable heavy chain sequence a sequence containing up to 1, 2, 3, 4, 5, 6, 7, 8, 9, or 10, amino acid substitutions within the framework regions of the variable heavy chain sequence of SEQ ID NO: 7 and/or as a variable light chain sequence, up to 1, 2, 3, 4, 5, 6, 7, 8, 9, or 10 amino acid substitutions within the framework regions of the variable light chain sequence of a sequence selected from the group consisting of SEQ ID NOs: 8, 13, 14, 15 and 16.

In a further embodiment, the anti-CD38 antibody or antigen binding fragment thereof may comprises, as a variable heavy chain sequence, up to 1, 2, 3, 4, 5, 6, 7, 8, 9, or 10 amino acid substitutions within SEQ ID NO: 7 and/or as a variable light chain sequence, up to 1, 2, 3, 4, 5, 6, 7, 8, 9, or 10 amino acid substitutions within SEQ ID NO: 8. In some embodiments, the anti-CD38 antibody may comprise as a variable heavy chain sequence a sequence containing up to 1, 2, 3, 4, 5, 6, 7, 8, 9, or 10, amino acid substitutions within the framework regions of the variable heavy chain sequence of SEQ ID NO: 7 and/or as a variable light chain sequence, up to 1, 2, 3, 4, 5, 6, 7, 8, 9, or 10 amino acid substitutions within the framework regions of SEQ ID NOs: 8.

In some embodiments, the anti-CD38 antibody (i.e. an antibody or antigen-binding fragment thereof and variants thereof as described herein, such as variants mutated to remove the DG motif) may comprise:
  a) the variable heavy chain region sequence of SEQ ID NO: 7 (or a variant thereof, such as an affinity matured variant thereof) or a variable heavy chain region sequence having up to 5 amino acid substitutions compared to the variable heavy chain region sequence of SEQ ID NO: 7 (or a variant thereof, such as an affinity matured variant thereof); and/or
  b) the variable light chain region sequence of a sequence selected from the group consisting of SEQ ID NO: 8, 13, 14, 15 and 16 (or a variant thereof, such as an affinity matured variant thereof) or a variable light chain region sequence having up to 5 amino acid substitutions compared to the variable light chain region sequence of a sequence selected from the group consisting of SEQ ID NO: 8, 13, 14, 15 and 16 (or a variant thereof, such as an affinity matured variant thereof).

In some embodiments, the anti-CD38 antibody (i.e. an antibody or antigen-binding fragment thereof and variants thereof as described herein, such as variants mutated to remove the DG motif) may comprise:
  a) the variable heavy chain region sequence of SEQ ID NO: 7 (or a variant thereof, such as an affinity matured variant thereof) or a variable heavy chain region sequence having up to 5 amino acid substitutions compared to the variable heavy chain region sequence of SEQ ID NO: 7 (or a variant thereof, such as an affinity matured variant thereof); and/or
  b) the variable light chain region sequence of SEQ ID NO: 8 (or a variant thereof, such as an affinity matured variant thereof) or a variable light chain region sequence having up to 5 amino acid substitutions compared to the variable light chain region sequence SEQ ID NO: 8 (or a variant thereof, such as an affinity matured variant thereof).

In some embodiments, the anti-CD38 antibody (i.e. an antibody or antigen-binding fragment thereof and variants thereof as described herein, such as variants mutated to remove the DG motif) may comprise:

a) the variable heavy chain region sequence of SEQ ID NO: 7 (or a variant thereof, such as an affinity matured variant thereof) or a variable heavy chain region sequence having up to 2 amino acid substitutions compared to the variable heavy chain region sequence of SEQ ID NO: 7 (or a variant thereof, such as an affinity matured variant thereof); and/or b) the variable light chain region sequence of a sequence selected from the group consisting of SEQ ID NO: 8, 9, 10, 11 and 12 (or a variant thereof, such as an affinity matured variant thereof) or a variable light chain region sequence having up to 2 amino acid substitutions compared to the variable light chain region sequence of a sequence selected from the group consisting of SEQ ID NO: 8, 13, 14, 15 and 16 (or a variant thereof, such as an affinity matured variant thereof).

In some embodiments, the anti-CD38 antibody (i.e. an antibody or antigen-binding fragment thereof and variants thereof as described herein, such as variants mutated to remove the DG motif) may comprise:

a) the variable heavy chain region sequence of SEQ ID NO: 7 (or a variant thereof, such as an affinity matured variant thereof) or a variable heavy chain region sequence having up to 2 amino acid substitutions compared to the variable heavy chain region sequence of SEQ ID NO: 7 (or a variant thereof, such as an affinity matured variant thereof); and/or b) the variable light chain region sequence of SEQ ID NO: 8 (or a variant thereof, such as an affinity matured variant thereof) or a variable light chain region sequence having up to 2 amino acid substitutions compared to the variable light chain region sequence of SEQ ID NO: 8 (or a variant thereof, such as an affinity matured variant thereof).

The amino acid substitutions preferably do not adversely effect, or not substantially adversely effect, the functional properties of the antibodies. The substitutions may therefore be considered conservative amino acid substitutions. Preferably, when amino acid substitutions do occur, they occur in a ratio of 1:1, such that the total length of the heavy and/or light chain variable region does not change.

In some embodiments, any amino acid substitutions (such as conservative amino acid substitutions) may occur only within the framework regions. In such embodiments, the CDR sequences remain unchanged.

The antibodies presenting such amino acid sequences and any substitutions can still present the binding and/or functional properties of aCD38-b-348 (such as binding to the same epitope or any of the functional features described herein for the disclosed anti-CD38 antibodies), and of anti-CD38 antibodies in general.

The invention also provides antibodies or antigen-binding fragments thereof, wherein the DG motif in the light or heavy chains of the antibodies may be altered, for example to reduce susceptibility to aspartate isomerization and/or wherein any methionine in the light or heavy chains of the antibodies may be altered, for example to reduce methionine oxidation. For example, a DG motif may be altered to substitute one or both of the amino acids in the motif with a different amino acid. For example, such motifs may be mutated to EG, DQ or DA. A methionine residue may be altered to replace it with a different amino acid, for example leucine or phenylalanine.

Accordingly, in some embodiments, the antibodies or fragments thereof provided herein can be mutated to remove or modify DG motifs, in particular DG motifs appearing in the CDR regions, as is standard in the art to reduce suscep- tibility to aspartate isomerisation. Such antibodies that have been modified in this may way need to undergo further modification (for example affinity maturation) before arriving at a final sequence.

In one embodiment of the invention, there is provided a variant antibody having CDR1, CDR2 and CDR3 sequences of an antibody as disclosed herein (for example the CDR1, CDR2 and CDR3 sequences of aCD38-b-348), or the variable heavy and variable light chain of any antibody as disclosed herein (for example the variable heavy and variable light chain of aCD38-b-348), but differing from the specified sequence in that at least one DG motif in the CDRs (if present) has been changed to a different motif. The disclosed variants may be used and formulated as described for aCD38-b-348.

For example aCD38-b-348 contains a DG motif in its LCDR3 sequence. In some embodiments, the aspartate of the DG motif may be changed to a different amino acid and/or the glycine of the DG motif may be changed to a different amino acid. In such embodiments, the anti-CD38 antibody or antigen-binding fragment thereof may be, or may be derived from, for example, aCD38-b-348. In some of the embodiments the variant antibodies or antigen-binding fragments thereof have a VL CDR3 sequence of any one of SEQ ID NOs: 9, 10, 11 or 12. For example, a variant LCDR3 sequence (for example a aCD38-b-348-m1 variant LCDR3 sequence as in SEQ ID NO: 9, aCD38-b-348-m2 variant LCDR3 sequence as in SEQ ID NO: 10, aCD38-b-348-m3 variant LCDR3 sequence as in SEQ ID NO: 11 or aCD38-b-348-m4 variant LCDR3 sequence as in SEQ ID NO: 12) can be incorporated into an antibody that comprises the LCDR1 and/or LCDR2 sequences of aCD38-b-348. In one embodiment, a variant LCDR3 sequence (for example a aCD38-b-348-m1 variant LCDR3 sequence as in SEQ ID NO: 9, aCD38-b-348-m2 variant LCDR3 sequence as in SEQ ID NO: 10, aCD38-b-348-m3 variant LCDR3 sequence as in SEQ ID NO: 11 or aCD38-b-348-m4 variant LCDR3 sequence as in SEQ ID NO: 12) can be incorporated into an antibody that comprises the LCDR1, LCDR2, HCDR1, HCDR2 and HCDR3 sequences of aCD38-b-348. In some embodiments, the variant antibody or antibody binding fragment thereof may comprise the variable heavy and variable light chain sequences of aCD38-b-348, but with the LCDR3 sequence mutated to remove the DG motif (for example SEQ ID NO: 9, 10, 11 or 12 may be present as a LCDR3 instead). The variant anti-CD38 antibodies provide further antibodies having any, and possibly all, binding and functional properties of the parental aCD38-b-348 (for example binding to the same epitope or any of the functional features described herein for the disclosed anti-CD38 antibodies). The disclosed variants may be used and formulated as described for aCD38-b-348.

The invention may also use other or further affinity matured antibodies, for example affinity matured variants derived from any of the antibodies disclosed herein. In one embodiment, the affinity matured antibodies are affinity matured antibodies having an altered DG motif and/or NG motif and/or altered to remove or mutate any methionine residues. The disclosed affinity matured variants may be used and formulated as described for aCD38-b-348.

In some embodiments the invention provides a method of preparing an anti-CD38 antibody comprising providing an antibody as herein described (e.g., aCD38-b-348 or an antigen binding fragment or variant thereof), and subjecting the antibody to affinity maturation, wherein the antibody produced binds to CD38 with greater affinity than the parental antibody. Preferably the produced antibody binds to CD38 with at least 20%, at least 30%, at least 40%, more preferably at least 50% greater affinity than the parental antibody binds to CD38, for example as measured by the Kd. Methods for measuring affinity are known in the art and described in the Examples below. The affinity matured antibodies produced by such methods can be formulated and used as described herein for the other anti-CD38 Antibody Agents.

aCD38-b-329 and Antibodies and Antigen Binding Fragments Derived Therefrom

The anti-CD38 antibody may be the anti-CD38 antibody aCD38-b-329, for example the aCD38-b-329 antibody disclosed in WO2018224685. The anti-CD38 antibody may be any antibody or antigen-binding fragment thereof that is based on or is derived from such an antibody.

In some embodiments, the anti-CD38 antibody or antigen-binding fragment thereof may comprise:
a) the amino acid sequence of SEQ ID NO: 17 as a HCDR1;
b) the amino acid sequence of SEQ ID NO: 18 as a HCDR2;
c) the amino acid sequence of SEQ ID NO: 19 as a HCDR3;
d) the amino acid sequence of SEQ ID NO: 20 as a LCDR1;
e) the amino acid sequence of SEQ ID NO: 21 as a LCDR2; and
f) the amino acid sequence of SEQ ID NO: 22 as a LCDR3 (as in aCD38-b-329).

In some embodiments, the anti-CD38 antibody or antigen-binding fragment thereof comprises a variable heavy chain comprising the amino acid sequence of SEQ ID NO: 23 and/or a variable light chain comprising the amino acid sequence of SEQ ID NO: 24 (as in aCD38-b-329).

In some embodiments the variable heavy chain sequence of aCD38-b-329 comprises the sequence:

```
                                        (SEQ ID NO: 23)
QLQLQESGPGLVKPSETLSLTCTVSGGSISSSDYYWGWIRQPPGKGLEWI

GSIYYSGSTYYNPSLKSRVTISVDTSKNQFSLKLSSVTAADTAVYYCAR

GQYSSGWYAYPFDMWGQGTMVTVSS
``` and the variable light chain sequence of aCD38-b-329 comprises the sequence:

```
                                        (SEQ ID NO: 24)
EIVLTQSPGTLSLSPGERATLSCRASQSVRSSYLAWYQQKPGQAPRLLIY

GASSRATGIPDRFSGSGSGTDFTLTISRLEPEDFAVYYCQQDGAVFTFGG

GTKVEIK.
```

In some embodiments, the anti-CD38 antibody may be a variant of aCD38-b-329. Such variants may be the antibodies aCD38-b-329-m6 or aCD38-b-329-m7.

For example, in some embodiments, the anti-CD38 antibody or antigen-binding fragment thereof may comprise:
a) the amino acid sequence of SEQ ID NO: 17 as a HCDR1;
b) the amino acid sequence of SEQ ID NO: 18 as a HCDR2;
c) the amino acid sequence of SEQ ID NO: 19 as a HCDR3;
d) the amino acid sequence of SEQ ID NO: 20 as a LCDR1;
e) the amino acid sequence of SEQ ID NO: 21 as a LCDR2; and
f) the amino acid sequence of SEQ ID NO: 25 as a LCDR3 (as in aCD38-b-329-m6).

In some embodiments, the anti-CD38 antibody or antigen-binding fragment thereof may comprise:
a) the amino acid sequence of SEQ ID NO: 17 as a HCDR1;
b) the amino acid sequence of SEQ ID NO: 18 as a HCDR2;
c) the amino acid sequence of SEQ ID NO: 19 as a HCDR3;
d) the amino acid sequence of SEQ ID NO: 20 as a LCDR1;
e) the amino acid sequence of SEQ ID NO: 21 as a LCDR2; and
f) the amino acid sequence of SEQ ID NO: 26 as a LCDR3 (as in aCD38-b-329-m7).

In some embodiments, the anti-CD38 antibody or antigen-binding fragment thereof comprises:
a) a variable heavy chain comprising the amino acid sequence of SEQ ID NO: 23 and/or a variable light chain comprising the amino acid sequence of SEQ ID NO: 27 (as in aCD38-b-329-m6); or
b) a variable heavy chain comprising the amino acid sequence of SEQ ID NO: 23 and/or a variable light chain comprising the amino acid sequence of SEQ ID NO: 28 (as in aCD38-b-329-m7).

Accordingly, the variant antibody aCD38-b-329-m6 may be characterised as comprising a heavy chain variable region comprising the sequence of:

```
                                        (SEQ ID NO: 23)
QLQLQESGPGLVKPSETLSLTCTVSGGSISSSDYYWGWIRQPPGKGLEWI

GSIYYSGSTYYNPSLKSRVTISVDTSKNQFSLKLSSVTAADTAVYYCARG

QYSSGWYAYPFDMWGQGTMVTVSS
``` and a variant light chain comprising the sequence:

```
                                        (SEQ ID NO: 27)
EIVLTQSPGTLSLSPGERATLSCRASQSVRSSYLAWYQQKPGQAPRLLIY

GASSRATGIPDRFSGSGSGTDFTLTISRLEPEDFAVYYCQQDEAVFTFGG

GTKVEIK
```

The variant antibody aCD38-b-329-m7 may be characterised as comprising a heavy chain variable region comprising the sequence of:

```
                                        (SEQ ID NO: 23)
QLQLQESGPGLVKPSETLSLTCTVSGGSISSSDYYWGWIRQPPGKGLEWI

GSIYYSGSTYYNPSLKSRVTISVDTSKNQFSLKLSSVTAADTAVYYCARG

QYSSGWYAYPFDMWGQGTMVTVSS
``` and a variant light chain comprising the sequence:

```
                                        (SEQ ID NO: 28)
EIVLTQSPGTLSLSPGERATLSCRASQSVRSSYLAWYQQKPGQAPRLLIY

GASSRATGIPDRFSGSGSGTDFTLTISRLEPEDFAVYYCQQDSAVFTFGG

GTKVEIK
```

The present invention may also use variant antibodies and antigen binding fragments thereof that have certain % identities relative to a reference sequence, such as the CDR sequences or the heavy and/or light chain variable sequences of aCD38-b-329.

For example, in some embodiments the anti-CD38 antibody or antigen binding fragment thereof comprises a variable heavy chain sequence comprising an amino acid sequence having at least 90% sequence identity to SEQ ID NO: 23. In some embodiments the anti-CD38 antibody or antigen binding fragment thereof comprises a variable heavy chain sequence comprising an amino acid sequence having at least 95% sequence identity to SEQ ID NO: 23. In some embodiments the anti-CD38 antibody or antigen binding fragment thereof comprises a variable heavy chain sequence comprising an amino acid sequence having at least 98% sequence identity to SEQ ID NO: 23. In some embodiments the anti-CD38 antibody or antigen binding fragment thereof comprises a variable heavy chain sequence comprising an amino acid sequence having at least 99% sequence identity to SEQ ID NO: 23. In some embodiments the anti-CD38 antibody or antigen binding fragment thereof comprises a variable heavy chain sequence comprising the amino acid sequence of SEQ ID NO: 23.

In some embodiments the anti-CD38 antibody or antigen binding fragment thereof comprises a variable light chain sequence comprising an amino acid sequence having at least 90% sequence identity to a sequence selected from the group consisting of SEQ ID NO: 24, 27 and 28. In some embodiments the anti-CD38 antibody or antigen binding fragment thereof comprises a variable light chain sequence comprising an amino acid sequence having at least 95% sequence identity to a sequence selected from the group consisting of SEQ ID NO: 24, 27 and 28. In some embodiments the anti-CD38 antibody or antigen binding fragment thereof comprises a variable light chain sequence comprising an amino acid sequence having at least 98% sequence identity to a sequence selected from the group consisting of SEQ ID NO: 24, 27 and 28. In some embodiments the anti-CD38 antibody or antigen binding fragment thereof comprises a variable heavy chain sequence comprising an amino acid sequence having at least 99% sequence identity to a sequence selected from the group consisting of SEQ ID NO: 24, 27 and 28. In some embodiments the anti-CD38 antibody or antigen binding fragment thereof comprises a variable light chain sequence identity to a sequence selected from the group consisting of SEQ ID NO: 24, 27 and 28.

In some embodiments the anti-CD38 antibody or antigen binding fragment thereof comprises a variable heavy chain sequence comprising an amino acid sequence having at least 90% sequence identity to SEQ ID NO: 23 and a variable light chain sequence comprising an amino acid sequence having at least 90% sequence identity to a sequence selected from the group consisting of SEQ ID NO: 24, 27 and 28. In some embodiments the anti-CD38 antibody or antigen binding fragment thereof comprises a variable heavy chain sequence comprising an amino acid sequence having at least 95% sequence identity to SEQ ID NO: 23 and a variable light chain sequence comprising an amino acid sequence having at least 95% sequence identity to a sequence selected from the group consisting of SEQ ID NO: 24, 27 and 28. In some embodiments the anti-CD38 antibody or antigen binding fragment thereof comprises a variable heavy chain sequence comprising an amino acid sequence having at least 98% sequence identity to SEQ ID NO: 23 and a variable light chain sequence comprising an amino acid sequence having at least 98% sequence identity to a sequence selected from the group consisting of SEQ ID NO: 24, 27 and 28. In some embodiments the anti-CD38 antibody or antigen binding fragment thereof comprises a variable heavy chain sequence comprising an amino acid sequence having at least 99% sequence identity to SEQ ID NO: 23 and a variable light chain sequence comprising an amino acid sequence having at least 99% sequence identity to a sequence selected from the group consisting of SEQ ID NO: 24, 27 and 28. In some embodiments the anti-CD38 antibody or antigen binding fragment thereof comprises a variable heavy chain sequence comprising the amino acid sequence of SEQ ID NO: 23 and a variable light chain sequence comprising an amino acid sequence selected from the group consisting of SEQ ID NO: 24, 27 and 28.

In some embodiments the anti-CD38 antibody or antigen binding fragment thereof comprises a variable heavy chain sequence comprising an amino acid sequence having at least 90% sequence identity to SEQ ID NO: 23 and a variable light chain sequence comprising an amino acid sequence having at least 90% sequence identity to SEQ ID NO: 24. In some embodiments the anti-CD38 antibody or antigen binding fragment thereof comprises a variable heavy chain sequence comprising an amino acid sequence having at least 95% sequence identity to SEQ ID NO: 23 and a variable light chain sequence comprising an amino acid sequence having at least 95% sequence identity to SEQ ID NO: 24. In some embodiments the anti-CD38 antibody or antigen binding fragment thereof comprises a variable heavy chain sequence comprising an amino acid sequence having at least 98% sequence identity to SEQ ID NO: 23 and a variable light chain sequence comprising an amino acid sequence having at least 98% sequence identity to SEQ ID NO: 24. In some embodiments the anti-CD38 antibody or antigen binding fragment thereof comprises a variable heavy chain sequence comprising an amino acid sequence having at least 99% sequence identity to SEQ ID NO: 23 and a variable light chain sequence comprising an amino acid sequence having at least 99% sequence identity to SEQ ID NO: 24. In some embodiments the anti-CD38 antibody or antigen binding fragment thereof comprises a variable heavy chain sequence comprising the amino acid sequence of SEQ ID NO: 23 and a variable light chain sequence comprising the amino acid sequence of SEQ ID NO: 24.

Such variant antibodies and antigen binding fragments thereof (i.e. ones having certain percent identities) may retain or exhibit the same (or substantially the same) functional and pharmacological properties as described for the antibodies and antigen binding fragments thereof having the heavy and light chain variable sequences disclosed herein for aCD38-b-329, for example binding to the same epitope as aCD38-b-329 or any of the functional features described herein for the disclosed anti-CD38 antibodies.

In some embodiments, in particular for any embodiments referencing sequences having a particular sequence identity to a reference sequence, the % sequence identity may be calculated without the sequence of all 6 CDRs of the specified heavy or light chain variable region. In such embodiments, the variations in sequence (if any) occur only in the framework regions.

In some embodiments, the anti-CD38 antibody may be an anti-CD38 antibody alternatively or additionally defined by a number of substitutions with respect to the aCD38-b-329 amino acid sequence elements defined above (or those of the variants m6 or m7).

For example, such an antibody may comprise, as variable heavy chain complementarity determining region 3 (HCDR3) a sequence containing up to 1, 2, 3, 4, 5, 6, 7, 8, 9, or 10, amino acid substitutions within aCD38-b-329-HCDR3 (SEQ ID NO: 19). In a further embodiment, the anti-CD38 antibody or antigen binding fragment thereof may comprise, as variable heavy chain complementarity determining regions 1, 2 and 3 (HCDR1, HCDR2, and HCDR3), sequences containing up to 1, 2, 3, 4, 5, 6, 7, 8, 9, or 10, amino acid substitutions within SEQ ID NO: 17, SEQ ID NO: 18 and SEQ ID NO: 19 respectively and/or as variable light chain complementarity determining regions 1, 2 and 3 (LCDR1, LCDR2, and LCDR3), sequences containing up to 1, 2, 3, 4, 5, 6, 7, 8, 9, or 10, amino acid substitutions within SEQ ID NO: 20, SEQ ID NO: 21 and a sequence selected from the group consisting of SEQ ID NOs: 22, 25 and 26, respectively.

In a further embodiment, the anti-CD38 antibody or antigen binding fragment thereof may comprises, as a variable heavy chain sequence, up to 1, 2, 3, 4, 5, 6, 7, 8, 9, or 10 amino acid substitutions within SEQ ID NO: 23 and/or as a variable light chain sequence, up to 1, 2, 3, 4, 5, 6, 7, 8, 9, or 10 amino acid substitutions within a sequence selected from the group consisting of SEQ ID NOs: 24, 27 and 28. In some embodiments, the anti-CD38 antibody may comprise as a variable heavy chain sequence a sequence containing up to 1, 2, 3, 4, 5, 6, 7, 8, 9, or 10, amino acid substitutions within the framework regions of the variable heavy chain sequence of SEQ ID NO: 23 and/or as a variable light chain sequence, up to 1, 2, 3, 4, 5, 6, 7, 8, 9, or 10 amino acid substitutions within the framework regions of the variable light chain sequence of a sequence selected from the group consisting of SEQ ID NOs: 24, 27 and 28.

In a further embodiment, the anti-CD38 antibody or antigen binding fragment thereof may comprises, as a variable heavy chain sequence, up to 1, 2, 3, 4, 5, 6, 7, 8, 9, or 10 amino acid substitutions within SEQ ID NO: 23 and/or as a variable light chain sequence, up to 1, 2, 3, 4, 5, 6, 7, 8, 9, or 10 amino acid substitutions within SEQ ID NO: 24. In some embodiments, the anti-CD38 antibody may comprise as a variable heavy chain sequence a sequence containing up to 1, 2, 3, 4, 5, 6, 7, 8, 9, or 10, amino acid substitutions within the framework regions of the variable heavy chain sequence of SEQ ID NO: 23 and/or as a variable light chain sequence, up to 1, 2, 3, 4, 5, 6, 7, 8, 9, or 10 amino acid substitutions within the framework regions of SEQ ID NOs: 24.

In some embodiments, the anti-CD38 antibody (i.e. an antibody or antigen-binding fragment thereof and variants thereof as described herein, such as variants mutated to remove the DG motif) may comprise:
  a) the variable heavy chain region sequence of SEQ ID NO: 23 (or a variant thereof, such as an affinity matured variant thereof) or a variable heavy chain region sequence having up to 5 amino acid substitutions compared to the variable heavy chain region sequence of SEQ ID NO: 23 (or a variant thereof, such as an affinity matured variant thereof); and/or
  b) the variable light chain region sequence of a sequence selected from the group consisting of SEQ ID NO: 24, 27 and 28 (or a variant thereof, such as an affinity matured variant thereof) or a variable light chain region sequence having up to 5 amino acid substitutions compared to the variable light chain region sequence of a sequence selected from the group consisting of SEQ ID NO: 24, 27 and 28 (or a variant thereof, such as an affinity matured variant thereof).

In some embodiments, the anti-CD38 antibody (i.e. an antibody or antigen-binding fragment thereof and variants thereof as described herein, such as variants mutated to remove the DG motif) may comprise:
  a) the variable heavy chain region sequence of SEQ ID NO: 23 (or a variant thereof, such as an affinity matured variant thereof) or a variable heavy chain region sequence having up to 5 amino acid substitutions compared to the variable heavy chain region sequence of SEQ ID NO: 23 (or a variant thereof, such as an affinity matured variant thereof); and/or
  b) the variable light chain region sequence of SEQ ID NO: 24 (or a variant thereof, such as an affinity matured variant thereof) or a variable light chain region sequence having up to 5 amino acid substitutions compared to the variable light chain region sequence SEQ ID NO: 24 (or a variant thereof, such as an affinity matured variant thereof).

In some embodiments, the anti-CD38 antibody (i.e. an antibody or antigen-binding fragment thereof and variants thereof as described herein, such as variants mutated to remove the DG motif) may comprise:
  a) the variable heavy chain region sequence of SEQ ID NO: 23 (or a variant thereof, such as an affinity matured variant thereof) or a variable heavy chain region sequence having up to 2 amino acid substitutions compared to the variable heavy chain region sequence of SEQ ID NO: 23 (or a variant thereof, such as an affinity matured variant thereof); and/or
  b) the variable light chain region sequence of a sequence selected from the group consisting of SEQ ID NO: 24, 27 and 28 (or a variant thereof, such as an affinity matured variant thereof) or a variable light chain region sequence having up to 2 amino acid substitutions compared to the variable light chain region sequence of a sequence selected from the group consisting of SEQ ID NO: 24, 27 and 28 (or a variant thereof, such as an affinity matured variant thereof).

In some embodiments, the anti-CD38 antibody (i.e. an antibody or antigen-binding fragment thereof and variants thereof as described herein, such as variants mutated to remove the DG motif) may comprise:
  a) the variable heavy chain region sequence of SEQ ID NO: 23 (or a variant thereof, such as an affinity matured variant thereof) or a variable heavy chain region sequence having up to 2 amino acid substitutions compared to the variable heavy chain region sequence of SEQ ID NO: 23 (or a variant thereof, such as an affinity matured variant thereof); and/or
  b) the variable light chain region sequence of SEQ ID NO: 24 (or a variant thereof, such as an affinity matured variant thereof) or a variable light chain region sequence having up to 2 amino acid substitutions compared to the variable light chain region sequence of SEQ ID NO: 24 (or a variant thereof, such as an affinity matured variant thereof).

The amino acid substitutions preferably do not adversely effect, or not substantially adversely effect, the functional properties of the antibodies. The substitutions may therefore be considered conservative amino acid substitutions. Preferably, when amino acid substitutions do occur, they occur in a ratio of 1:1, such that the total length of the heavy and/or light chain variable region does not change.

In some embodiments, any amino acid substitutions (such as conservative amino acid substitutions) may occur only within the framework regions. In such embodiments, the CDR sequences remain unchanged.

The antibodies presenting such amino acid sequences and any substitutions can still present the binding and/or functional properties of aCD38-b-329 (such as binding to the same epitope or any of the functional features described herein for the disclosed anti-CD38 antibodies), and of anti-CD38 antibodies in general.

The invention also provides antibodies or antigen-binding fragments thereof, wherein the DG motif in the light or heavy chains of the antibodies may be altered, for example to reduce susceptibility to aspartate isomerization and/or wherein any methionine in the light or heavy chains of the antibodies may be altered, for example to reduce methionine oxidation. For example, a DG motif may be altered to substitute one or both of the amino acids in the motif with a different amino acid. For example, such motifs may be mutated to EG, DQ or DA. A methionine residue may be altered to replace it with a different amino acid, for example leucine or phenylalanine.

Accordingly, in some embodiments, the antibodies or fragments thereof provided herein can be mutated to remove or modify DG motifs, in particular DG motifs appearing in the CDR regions, as is standard in the art to reduce susceptibility to aspartate isomerisation. Such antibodies that have been modified in this may way need to undergo further modification (for example affinity maturation) before arriving at a final sequence.

In one embodiment of the invention, there is provided a variant antibody having CDR1, CDR2 and CDR3 sequences of an antibody as disclosed herein (for example the CDR1, CDR2 and CDR3 sequences of aCD38-b-329), or the variable heavy and variable light chain of any antibody as disclosed herein (for example the variable heavy and variable light chain of aCD38-b-329), but differing from the specified sequence in that at least one DG motif in the CDRs (if present) has been changed to a different motif. The disclosed variants may be used and formulated as described for aCD38-b-329.

For example aCD38-b-329 contains a DG motif in its LCDR3 sequence. In some embodiments, the aspartate of the DG motif may be changed to a different amino acid and/or the glycine of the DG motif may be changed to a different amino acid. In such embodiments, the anti-CD38 antibody or antigen-binding fragment thereof may be, or may be derived from, for example, aCD38-b-329. In some of the embodiments the variant antibodies or antigen-binding fragments thereof have a VL CDR3 sequence of any one of SEQ ID NOs: 25 or 26. For example, a variant LCDR3 sequence (for example a aCD38-b-329-m6 variant LCDR3 sequence as in SEQ ID NO: 25 or aCD38-b-329-m7 variant LCDR3 sequence as in SEQ ID NO: 26) can be incorporated into an antibody that comprises the LCDR1 and/or LCDR2 sequences of aCD38-b-329. In one embodiment, a variant LCDR3 sequence (for example a aCD38-b-329-m6 variant LCDR3 sequence as in SEQ ID NO: 25 or aCD38-b-329-m7 variant LCDR3 sequence as in SEQ ID NO: 26) can be incorporated into an antibody that comprises the LCDR1, LCDR2, HCDR1, HCDR2 and HCDR3 sequences of aCD38-b-329. In some embodiments, the variant antibody or antibody binding fragment thereof may comprise the variable heavy and variable light chain sequences of aCD38-b-329, but with the LCDR3 sequence mutated to remove the DG motif (for example SEQ ID NO: 25 or 26 may be present as a LCDR3 instead). The variant anti-CD38 antibodies provide further antibodies having any, and possibly all, binding and functional properties of the parental aCD38-b-329 (for example binding to the same epitope or any of the functional features described herein for the disclosed anti-CD38 antibodies). The disclosed variants may be used and formulated as described for aCD38-b-329.

Further Antibodies that May be Used in the Invention

The invention may also use affinity matured antibodies, for example an affinity matured variant derived from any of the antibodies disclosed herein. In one embodiment, the affinity matured antibodies are affinity matured antibodies having an altered DG motif and/or NG motif and/or altered to remove or mutate any methionine residues. The disclosed affinity matured variants may be used and formulated as described for aCD38-b-348 or aCD38-b-329.

In some embodiments the invention provides a method of preparing an anti-CD38 antibody comprising providing an antibody as herein described (e.g., aCD38-b-329 or an antigen binding fragment or variant thereof), and subjecting the antibody to affinity maturation, wherein the antibody produced binds to CD38 with greater affinity than the parental antibody. Preferably the produced antibody binds to CD38 with at least 20%, at least 30%, at least 40%, more preferably at least 50% greater affinity than the parental antibody binds to CD38, for example as measured by the Kd. Methods for measuring affinity are known in the art and described in the Examples below. The affinity matured antibodies produced by such methods can be formulated and used as described herein for the other anti-CD38 Antibody Agents.

Affinity maturation may be carried out according to any suitable method known to the skilled person. For example, in vitro antibody display systems are widely used for the generation of specific antibodies with high affinity. In these systems, the phenotype (i.e., the antibody fragment) is coupled to the genotype (i.e., the antibody gene) allowing the direct determination of the sequence of the antibody. Several systems have been developed to achieve display of antibody repertoires to allow subsequent selection of binders and by increasing the stringency of selection allows for the selection of higher and higher affinity variants. The antibody fragments can be expressed in yeast, ribosomes, phage display particles or by direct coupling to DNA.

Current antibody affinity maturation methods belong to two mutagenesis categories: stochastic and non-stochastic. Error-prone polymerase chain reaction (PCR), mutator bacterial strains, and saturation mutagenesis are typical examples of stochastic mutagenesis methods. Non-stochastic techniques often use alanine-scanning or site-directed mutagenesis to generate limited collections of specific variants. In addition, shuffling approaches to obtain shuffled variants of the parent antibody can also be used to improve antibodies affinity further.

Accordingly, in one embodiment of the invention, the method of affinity maturation is selected from the group consisting of stochastic mutagenesis (for example error-prone polymerase chain reaction (PCR), mutator bacterial strains, or saturation mutagenesis), non-stochastic mutagenesis (for example alanine-scanning or site-directed mutagenesis), shuffling (for example DNA shuffling, chain shuffling or CDR shuffling) and the use of the CRISPR-Cas9 system to introduce modifications.

Affinity maturation methods are described in, for example, Rajpal et al., Proc Natl Acad Sci USA, 2005, 102(24):8466-71, Steinwand et al., MAbs, 2014, 6(1):204-18, as well as in Handbook of Therapeutic Antibodies, Wiley, 2014, Chapter 6, Antibody Affinity (pages 115-140).

The present invention may also use anti anti-CD38 antibodies or antigen-binding fragments thereof that compete with any of the disclosed antibodies, such as aCD38-b-348 or aCD38-b-329 or any variants derived thereof (for example fragments containing some or not all of the specified CDR or variable chain sequences, or variants having certain percent identities and/or amino acid substitutions), for binding to CD38.

Administration of Anti-CD38 Antibodies

In some embodiments, the methods comprise obtaining a sample from a patient that has been previously administered the anti-CD38 antibody or antigen binding fragment thereof (in other words, the sample if provided or obtained from a patient to whom the anti-CD38 antibody or antigen binding fragment thereof was administered at a previous point in time). In other embodiments, the methods described herein further comprise a step of administering the anti-CD38 antibody to the patient prior to the sample being obtained from the patient. In all cases, the anti-CD38 antibody has been administered prior to obtaining the blood sample from the patient, such that the blood sample comprises the anti-CD38 antibody that has been administered (since the anti-CD38 antibody will generally have been administered intravenously or subcutaneously and circulates in the patient's blood stream).

Generally, the patient should have been administered the anti-CD38 antibody within a time frame that means the blood sample obtained from the patient comprises some of the therapeutic anti-CD38 antibody molecules. In some embodiments, the patient has been administered the anti-CD38 antibody less than 1 year, less than 6 months, less than 3 months, less than 2 months or less than 1 month prior to the sample being obtained from the patient. In some embodiments, the patient has been administered the anti-CD38 antibody less than 8 weeks, less than 7 weeks, less than 6 weeks, less than 5 weeks, less than 4 weeks, less than 3 weeks, less than 2 weeks or less than 1 week prior to the sample being obtained from the patient. In some embodiments, the patient has been administered the anti-CD38 antibody less than 10 days, less than 9 days, less than 8 days, less than 7 days, less than 6 days, less than 5 days, less than 4 days, less than 3 days, less than 2 days or less than 1 day prior to the sample being obtained from the patient. In some embodiments, the patient has been administered the anti-CD38 antibody less than 48 hours, less than 24 hours, less than 12 hours, less than 6 hours, less than 5 hours, less than 4 hours, less than 3 hours, less than 2 hours or less than 1 hour prior to the sample being obtained from the patient.

In preferred embodiments, the patient has been administered the anti-CD38 antibody less than 2 months of the sample being obtained from the patient.

In embodiments comprising the step of administration of the anti-CD38 antibody or antigen binding fragment thereof, the step of administration takes places prior any step of obtaining a sample from the patient. Depending on the precise treatment regimen of the patient, there may be a delay between administration of the anti-CD38 antibody or antigen binding fragment thereof and obtaining the sample from the patient. Generally, the sample will be obtained less than 2 months after administration of the anti-CD38 antibody or antigen binding fragment thereof to the patient.

The anti-CD38 antibodies administered to the patient prior to sample collection are anti-CD38 antibodies that do not cause interference when crossmatching a patient blood sample with donor red blood cells or when performing any antibody RBC panel assay. The anti-CD38 antibody or antigen binding fragment thereof is not, therefore, daratumumab or isatuximab (for example). Anti-CD38 antibodies compatible with the present invention are discussed elsewhere under the heading "The anti-CD38 antibody or antigen binding fragment thereof".

Assay Types

The methods described herein comprise a step of screening a blood sample from a patient. The screening may comprise determining the presence or absence of one or more patient antibodies in the patient blood sample. In some embodiments, the screening is performed using an assay selected from the group consisting of a column agglutination assay, an indirect antiglobulin test (IAT) tube assay, and a solid phase assay. In some embodiments, the screening is performed using a column agglutination assay. In some embodiments, the screening is performed using an indirect antiglobulin test (IAT) tube assay. In some embodiments, the screening is performed using a solid phase assay. These are described in further detail in the definitions provided above.

Red Blood Cell Antigens:

The term "red blood cell antigen" refers to any antigen found on the surface of a red blood cell or expressed by a red blood cell. RBC antigens may be grouped according to the moieties on which they are found. For example, the "K" and "k" RBC antigens are found on the "Kell" glycoprotein, and belong to the "Kell group" of RBC antigens. Groups of antigens may be referred to as a "blood group" or "blood group system", for example, the "Kell blood group". Each blood group may contain several different antigens, sometimes as many as 50 or more antigens. RBCs from one individual may be positive or negative for different antigens within the same blood group.

RBC antigens may be carbohydrates, for example the ABO group antigens, or may be proteins, for example, the Rhesus (Rh) group antigens. When a patient is exposed to an RBC antigen, they may produce antibodies against that antigen, for example alloantibodies of the IgG subtype or IgM subtype. Binding of patient antibodies to RBC antigens in vivo can result in destruction (haemolysis) of the RBC. Because of this potentially harmful effect, patients who receive blood transfusions are screened to identify any antibodies in the patient plasma or serum that specifically bind to RBC antigens. RBC antigens against which clinically significant patient antibodies may occur include the Ab group, ABO group, Cromer group, Diego group, Duffy group, Gerbich group, GLOB group, Indian group, Kell group, Kidd group, Knops group, Lewis group, Lutheran group, LW group, MNS group, P1 group, Rh group, XK group, Xg group, and the Yt group. Exemplary blood group antigens are described in more detail below.

The ABO blood group antigens are the most immunogenic of all blood group systems and form the basis for routine blood typing in blood banks. ABO blood group antigens are RBC-membrane bound, attached to oligosaccharide chains that project above the RBC surface. The group consists of four antigens: A, B, AB and A1. Naturally-occurring antibodies against the ABO group antigens are frequently found in serum, for example, a patient with an A-type blood group has anti-B antibodies in their serum. Because patient antibodies that specifically bind to the ABO blood group antigens are naturally occurring (i.e. they arise without being exposed to a non-self antigen, for example through blood transfusion) and are very common, all patients are screened to determine their ABO status. Antibodies against the ABO group antigens may be IgG or IgM. Antibodies against the ABO group antigens may cause significant acute haemolytic transfusion reaction if incompatible RBCs are transfused. ABO typing is unaffected by the presence of anti-CD38 antibodies, such as daratumumab or isatuximab, in a patient's blood.

The Rh blood group is one of the most complex blood groups, comprising at least 50 known antigens of which D, C, E, c and e are the most clinically significant. Rh group antigens are highly immunogenic. Rh group antigens are found on the proteins RhD and RhCE, both transmembrane RBC proteins. Rh phenotyping is routinely performed prior to a patient receiving a blood transfusion, and commonly uses monoclonal or polyclonal anti-D, anti-C, anti-E, anti-c and anti-e reagents which bind to any Rh group antigens present on RBCs. As such, routine Rh phenotyping is not typically affected by the presence of anti-CD38 antibodies, such as daratumumab or isatuximab, in a patient's blood. Patient antibodies against Rh blood group antigens, in particular RhD, are a major cause of haemolytic disease of the foetus and newborn (HDFN).

The Kell blood group system arises from the Kell glycoprotein, a transmembrane RBC protein that carries the Kell antigens. The Kell blood group system is complex, consisting of over 30 antigens, many of which are highly immunogenic. The two major Kell group antigens are K and k, with K being the most immunogenic. Antibodies against Kell group antigens are typically of the IgG antibody class, with IgM antibodies being less common. Anti-Kell group antibodies known to cause adverse reactions (such as transfusion reaction or HDFN) include anti-K, anti-k, anti-Kp$^a$, and anti-Js$^b$. Kell group antigens are among those antigens that are denatured by treatment of RBCs with an antigen-stripping agent such as DTT or similar. This makes patient antibodies against Kell group antigens particularly difficult to accurately identify in patients treated with anti-CD38 antibodies, such as daratumumab or isatuximab, where DTT or similar has been used to remove CD38 from RBCs in order to prevent agglutination caused by the presence of the anti-CD38 antibody.

The Kidd blood group system arises from the Kidd (JK) glycoprotein, a transmembrane glycoprotein expressed on RBCs that transports urea across the red blood cell membrane. There are three known Kidd antigens (Jk1 (Jk$^a$), Jk2 (Jk$^b$) and Jk3). Anti-Kidd patient antibodies, in particular anti-Jk$^a$, are known to cause delayed haemolytic transfusion reactions. Foetal Kidd antigens are also capable of causing alloimmunisation of the mother.

The Duffy blood group includes six known antigens which reside on the Duffy transmembrane glycoprotein expressed on RBCs, also known as DARC (Duffy antigen/receptor for chemokines). The six known Duffy antigens include Fy$^a$, Fy$^b$, Fy3, Fy4, Fy5, and Fy6. Patient antibodies against the Duffy antigens are predominantly of the IgG subclass, while IgM subclass patient antibodies are rare. Patient antibodies against Duffy antigens are known to cause both haemolytic transfusion reaction and HDFN, in particular patient antibodies against the Duffy antigens Fy$^a$ and Fy$^b$.

The Diego blood group system arises from the Diego protein, a transmembrane protein expressed on RBCs. The Diego blood group system includes 21 antigens, of which Di$^a$, Di$^b$, and Wr$^a$ are among the most significant. Patient antibodies against Diego blood group antigens may be IgG and/or IgM antibodies. Patient antibodies against Diego blood group antigens are known to cause both haemolytic transfusion reaction and HDFN.

The Lutheran blood group system includes 24 known antigens. These are formed from two Lutheran glycoprotein isoforms expressed on the RBC membrane. Patient antibodies against Lutheran group antigens may be IgG and/or IgM antibodies. Patient antibodies against Lutheran group antigens may cause haemolytic transfusion reactions or HDFN, although these are rare and typically mild. Lutheran group antigens are among those antigens that are denatured by treatment of RBCs with an antigen-stripping agent such as DTT or similar. This makes patient antibodies against Lutheran group antigens particularly difficult to accurately identify in patients treated with anti-CD38 antibodies, such as daratumumab or isatuximab, where DTT or similar has been used to remove CD38 from RBCs in order to prevent agglutination caused by the presence of the anti-CD38 antibody The MNS blood group system arises from the antigen-bearing proteins Glycophorin A and Glycophorin B, both glycophorin proteins expressed on the RBC membrane. The MNS blood group system is known to include at least 43 antigens, many of which are implicated in HDFN. Patient antibodies against MNS blood group antigens are also known to cause haemolytic transfusion reactions varying from mild to severe. Patient antibodies against MNS blood group antigens may be IgG and/or IgM antibodies.

Other blood group antigens, such as Cromer group, Gerbich group, GLOB group, Indian group, Knops group, Lewis group, LW group, P1 group, XX group, Xg group and Yt group antigens, may also be expressed on RBCs and may be capable of causing haemolytic transfusion reaction or HDFN if RBCs possessing these antigens are transfused to a patient with antibodies that specifically bind any of the antigens within a group.

The presence of patient antibodies in a patient sample against any of the above described blood group antigens is routinely assessed in blood banks and is known to be affected by the presence of anti-CD38 antibodies, such as daratumumab or isatuximab, in the patient's blood. In contrast, the methods of the present invention enable accurate antibody screening and blood crossmatching of patient samples when the patient has been treated with an anti-CD38 antibody, and do not require additional steps to inhibit binding of the anti-CD38 antibody to CD38 expressed on RBCs (membrane-bound CD38).

Accordingly, in some embodiments the RBC antigens may be selected from the group consisting of the Ab group antigens, the ABO group antigens, the Cromer group antigens, the Diego group antigens, the Duffy group antigens, the Gerbich group antigens, the GLOB group antigens, the Indian group antigens, the Kell group antigens, the Kidd group antigens, the Knops group antigens, the Lewis group antigens, the Lutheran group antigens, the LW group antigens, the MNS group antigens, the P1 group antigens, the Rh group antigens, the XK group antigens, the Xg group antigens, and the Yt group antigens.

The RBC antigens are expressed by RBCs. This means they are present on the surface of the RBCs. The RBC antigens may also be referred to as being membrane-bound, since they are incorporated into the RBC membrane with at least a portion exposed on the surface of the RBC.

More Specific Methods of the Invention

The present invention comprises at least the following methods.

The present invention provides a method of screening a blood sample obtained from a patient, wherein the patient has been administered an anti-CD38 antibody or antigen binding fragment thereof, the method comprising:
  a) providing a blood sample from the patient;
  b) providing a blood sample from a donor, wherein the donor blood sample comprises donor red blood cells;
  c) contacting the patient blood sample and the donor red blood cells from the donor blood sample to provide a patient blood/donor red blood cell mixture;
  d) incubating the patient blood/donor red blood cell mixture to enable any one or more patient antibodies in the patient blood sample, if present, to bind to one or more red blood cell antigens present on the donor red blood cells, to form one or more patient antibody/donor red blood cell antigen complexes;
e) adding to the patient blood/donor red blood cell mixture an agent that specifically binds together any patient antibody/donor red blood cell antigen complexes present in the patient blood/donor red blood cell mixture, for example an agglutination agent, such as an anti-human globulin;
f) optionally separating, if present, the any one or more patient antibody/donor red blood cell antigen complexes from the patient blood/donor red blood cell mixture, further optionally wherein the separating step comprises centrifugation; and
g) determining the presence or absence of one or more patient antibodies in the patient blood sample that specifically bind to one or more red blood cell antigens expressed on the surface of the donor red blood cells.

The present invention also includes a method of screening a blood sample obtained from a patient, wherein the patient has been administered an anti-CD38 antibody or antigen binding fragment thereof, the method comprising:
a) providing a blood sample from the patient, wherein the patient blood sample comprises one or more patient antibodies that specifically bind one or more red blood cell antigens, wherein the patient antibodies do not specifically bind any red blood cell antigens expressed by the patient's red blood cells;
b) providing a blood sample from a donor, wherein the donor blood sample comprises donor red blood cells;
c) contacting the patient blood sample and the donor red blood cells from the donor blood sample to provide a patient blood/donor red blood cell mixture;
d) incubating the patient blood/donor red blood cell mixture to enable the one or more patient antibodies in the patient blood sample to bind to one or more red blood cell antigens present on the donor red blood cells, to form one or more patient antibody/donor red blood cell antigen complexes;
e) adding to the patient blood/donor red blood cell mixture an agent that specifically binds together the patient antibody/donor red blood cell antigen complexes present in the patient blood/donor red blood cell mixture, for example an agglutination agent, such as an anti-human globulin;
f) optionally separating the any one or more patient antibody/donor red blood cell antigen complexes from the patient blood/donor red blood cell mixture, further optionally wherein the separating step comprises centrifugation; and
g) determining the presence of one or more patient antibodies in the patient blood sample that specifically bind to one or more red blood cell antigens expressed on the surface of the donor red blood cells;
wherein the presence of patient antibodies that specifically bind to one or more red blood cell antigens present on the one or more red blood cells from the donor blood sample indicates the donor blood sample is incompatible with the patient.

The present invention also includes a method of screening a blood sample obtained from a patient, wherein the patient has been administered an anti-CD38 antibody or antigen binding fragment thereof, the method comprising:
a) providing a blood sample from the patient, wherein the patient blood sample does not comprise any patient antibodies that specifically bind to any red blood cell antigens;
b) providing a blood sample from a donor, wherein the donor blood sample comprises donor red blood cells;
c) contacting the patient blood sample and the donor red blood cells from the donor blood sample to provide a patient blood/donor red blood cell mixture;
d) d) adding to the patient blood/donor red blood cell mixture an agglutination agent, for example an anti-human globulin;
e) optionally isolating the donor red blood cells from the patient blood/donor red blood cell mixture, optionally wherein the isolating step comprises centrifugation;
f) determining the absence of one or more patient antibodies in the patient blood sample that specifically bind to one or more red blood cell antigens expressed on the surface of the donor red blood cells;
wherein the absence of patient antibodies that specifically bind to one or more red blood cell antigens present on the one or more red blood cells from the donor blood sample indicates the donor blood sample is compatible with the patient.

The present invention also includes a method of screening a blood sample obtained from a patient, wherein the patient has been administered an anti-CD38 antibody or antigen binding fragment thereof, the method comprising:
a) providing a blood sample from the patient;
b) screening the patient blood sample against a red blood cell panel to determine the presence or absence of any patient antibodies in the patient blood sample that specifically bind to any red blood cell antigens present on the surface of any red blood cells in the red blood cell panel;
c) providing a blood sample from a donor, wherein the donor blood sample comprises donor red blood cells, and wherein the donor red blood cells in the donor blood sample do not express any red blood cell antigens capable of being specifically bound by any of the patient antibodies identified in step (b) as specifically binding to any red blood cell antigens expressed on the surface of any red blood cells in the red blood cell panel;
d) screening the patient blood sample, comprising determining the presence or absence of one or more patient antibodies in the patient blood sample that specifically bind to one or more red blood cell antigens expressed on the surface of the donor red blood cells. Step (c) may be conducted according to any suitable screening method disclosed herein.

The present invention also includes a method of screening a blood sample obtained from a patient, wherein the patient has been administered an anti-CD38 antibody or antigen binding fragment thereof, the method comprising:
a) providing one or more blood samples from the patient;
b) screening a patient blood sample provided in step (a) against a red blood cell panel to determine the presence or absence of any patient antibodies in the patient blood sample that specifically bind to any red blood cell antigens present on the surface of any red blood cells in the red blood cell panel;
c) providing a blood sample from a donor, wherein the donor blood sample comprises donor red blood cells, and wherein the donor red blood cells in the donor blood sample do not express any red blood cell antigens capable of being specifically bound by any of the patient antibodies identified in step (b) as specifically binding to any red blood cell antigens expressed on the surface of any red blood cells in the red blood cell panel;

d) contacting a patient blood sample provided in step (a) and the donor red blood cells from the donor blood sample to provide a patient blood/donor red blood cell mixture;

e) incubating the patient blood/donor red blood cell mixture to enable any one or more patient antibodies in the patient blood sample, if present, to bind to one or more red blood cell antigens present on the donor red blood cells, to form one or more patient antibody/donor red blood cell antigen complexes;

f) adding to the patient blood/donor red blood cell mixture an agent that specifically binds together any patient antibody/donor red blood cell antigen complexes present in the patient blood/donor red blood cell mixture, for example an agglutination agent, such as an anti-human globulin;

g) optionally separating, if present, the any one or more patient antibody/donor red blood cell antigen complexes from the patient blood/donor red blood cell mixture, further optionally wherein the separating step comprises centrifugation;

h) determining the presence or absence of one or more patient antibodies in the patient blood sample that specifically bind to one or more red blood cell antigens expressed on the surface of the donor red blood cells.

Any of the above methods can be combined with any of the more detailed or preferred embodiments of the present disclosure described herein.

Incubation steps of any of the methods described herein may be performed under conditions sufficient to allow binding of any patient antibodies (if present) to any red blood cell antigens present on red blood cells of a donor blood sample, or to any red blood cell antigens present on the red blood cells of a red blood cell panel. The incubation may be performed for from about 5 minutes and to about 2 hours. Incubation may be performed for at least about 5 minutes, at least about 10 minutes, at least about 15 minutes, at least about 20 minutes, at least about 30 minutes, at least about 40 minutes, at least about 50 minutes, at least about 1 hour, at least about 90 minutes or at least about 2 hours. Incubation may occur at about 37° C. Incubation may occur at about room temperature (for example from about 15° C. to about 25° C.). In some embodiments, the incubations step comprises incubating for at least about 5 mins at a temperature of from about 15° C. to about 40° C.

Methods of Treatment and Medical Uses

The present invention provides method of treating a cancer in a patient, the method comprising providing a blood sample from the patient, and screening the blood sample according to a method of the invention. In some embodiments, the patient has been administered an anti-CD38 antibody or antigen binding fragment thereof (i.e. they have already received the anti-CD38 antibody or antigen binding fragment thereof at an earlier point in time). In other embodiments, the method comprises the set of administration of the anti-CD38 antibody or antigen binding fragment thereof to the patient. In some embodiments, the method may alternatively or additionally comprise a step of obtaining the sample from the patient. The sample is a blood sample and may be obtained according to any suitable method known to the skilled person (for example a simple blood draw). The sample may be processed prior to screening, for example it may be diluted or other processing steps may be carried out, as discussed elsewhere.

In some embodiments, the method comprises:

a) administering to the patient an anti-CD38 antibody or antigen binding fragment thereof; and b) obtaining a blood sample from the patient after administration of the anti-CD38 antibody or antigen binding fragment thereof; and c) screening the patient blood sample according to the method of any one of claims 1 to X.

The methods of the invention may comprise generating a report, wherein the report indicates the presence or absence of patient antibodies in the patient blood sample and/or the suitability of the donor to provide a blood or red blood cell donation to the patient.

The methods of treatment may comprising a step of administering blood or red blood cells from the donor if the donor is found to be compatible with the patient, for example by blood transfusion.

The methods of the invention therefore extend to methods of administering a blood transfusion to a patient, wherein compatible donor blood or donor red blood cells are administered to the patient, wherein the donor blood or donor red blood cells have been determined as being compatible with the patient according to any of the screening methods of the invention. The donor blood has therefore been crossmatched with the patient and is only administered to the patient if the blood was found to be compatible. For example, in some embodiments the method is a method of administering a blood transfusion to a patient, the method comprising:

a) providing donor blood or donor red blood cells, where the donor blood or donor red blood cells have been determined as being compatible with a patient according to any screening method of the invention; and b) administering the compatible donor blood or compatible donor red blood cells to the patient.

The patient is a patient to whom the anti-CD38 antibodies or antigen binding fragments thereof have been administered at an early point in time, notably prior to obtaining a blood sample from the patient to determine compatibility of the donor blood or donor red blood cells with the patient.

The methods of administering a blood transfusion to a patient may include the steps of screening the donor blood or donor red blood cells for compatibility with the patient (i.e. crossmatching).

In some embodiments, the present invention includes treatment of cancer, such as a B cell malignancy, a lymphoma, (Hodgkins Lymphoma, non-Hodgkins lymphoma, chronic lymphocytic, leukemia, acute lymphoblastic leukemia, myelomas), a myeloproliferative disorders, a solid tumor (such as a breast carcinoma, a squamous cell carcinoma, a colon cancer, a head and neck cancer, a lung cancer, a genitourinary cancer, a rectal cancer, a gastric cancer, sarcoma, melanoma, an esophageal cancer, liver cancer, testicular cancer, cervical cancer, mastocytoma, hemangioma, eye cancer, laryngeal cancer, mouth cancer, mesothelioma, skin cancer, rectal cancer, throat cancer, bladder cancer, breast cancer, uterine cancer, prostate cancer, lung cancer, pancreatic cancer, renal cancer, gastric cancer, non-small cell lung cancer, and ovarian cancer). The cancer can be also defined on the basis of presence of specific tumor-relevant markers and antigens such as CD20, HER2, PD-1, PD-L1, SLAM7F, CD47, CD137, CD134, TIM3, CD25, GITR, CD38, EGFR, etc., or a cancer that has been identified as having a biomarker referred to as microsatellite instability-high (MSI-H) or mismatch repair deficient (dMMR). Furthermore, such conditions may also be considered when defining pre-cancerous, non-invasive states of the above cancers, such as cancer in-situ, smouldering myeloma, monoclonal gammopathy of undetermined significance, cervical intra-epithelial neoplasia, MALTomas/GALTomes and various lymphoproliferative disorders. Preferably in some embodiments the subject being treated has a solid tumor. In one embodiment the subject has a heamatological cancer. In some embodiments the subject has a CD38 positive tumor.

Methods and use of the invention may particularly be useful when the patient may require one or more blood transfusions. For example, in some embodiments, the disease to be treated is cancer, for example multiple myeloma. Patients receiving anti-CD38 antibodies as treatment for multiple myeloma may require one or more blood transfusions requiring blood screening (in particular crossmatching with a donor) to identity a donor that is compatible with the patient.

Thus, in some embodiments, the present invention provides methods of treating cancer in a subject, comprising administering to the subject an effective amount of a composition comprising anti-CD38 antibodies or antigen-binding fragments thereof as described herein (e.g. aCD38-b-348 or aCD38-b-329 or antibodies derived therefrom). In some embodiments, provided methods may further comprise administering, simultaneously or sequentially in any order, at least one additional agent or therapy to the subject (i.e., so that the subject receives a combination therapy). In some embodiments, such an at least one additional agent or therapy can be or comprise an anticancer drug (e.g., a chemotherapeutic agent), radiotherapy (by applying irradiation externally to the body or by administering radioconjugated compounds), an anti-tumor antigen or marker antibody (the antigen or marker being for example CD4, CD25, CA125, PSMA, c-MET, VEGF, CD137, VEGFR2, CD20, HER2, HER3, SLAMF7, CD326, CAIX, CD40, CD47, or EGF receptor), a checkpoint inhibitor or an immunomodulating antibody (for example an antibody targeting PD-1. PD-L1, TIM3, CD25, GITR, CD134, CD134L, CD137L, CD80, CD86, B7-H3, B7-H4, B7RP1, LAG3, ICOS, TIM3, GALS, CD28, AP2M1, SHP-2, OX-40 etc.), a vaccine, an adjuvant, standard-of-use protocol, one or more other compounds targeting cancer cells or stimulating an immune response against cancer cells, or any combination thereof. In certain particular embodiments, when such at least one additional agent or therapy is or comprises an antibody, the format of and/or the antigen targeted by such antibody can be chosen among those listed in the literature and possibly adapted to a given cancer (Sliwkowski M & Mellman I, 2013; Redman J M et al., 2015; Kijanka M et al., 2015).

Among other methods, the present invention provides a method of screening donor blood sample for compatibility with a patient, wherein the patient has been administered an anti-CD38 antibody or antigen binding fragment thereof, the method comprising:
a) providing a blood sample obtained from the patient;
b) providing a blood sample from a donor, wherein the donor blood sample comprises donor red blood cells;
c) contacting the patient blood sample and the donor red blood cells from the donor blood sample to provide a patient blood/donor red blood cell mixture;
d) incubating the patient blood/donor red blood cell mixture for at least 5 minutes at a temperature of from about 15° C. to about 40° C. to enable any one or more patient IgG alloantibodies in the patient blood sample, if present, to bind to one or more red blood cell antigens present on the donor red blood cells, to form one or more patient IgG alloantibody/donor red blood cell antigen complexes;
e) adding to the patient blood/donor red blood cell mixture anti-human IgG antibodies to agglutinate any patient IgG alloantibody/donor red blood cell antigen complexes present in the patient blood/donor red blood cell mixture;
f) separating, if present, the any one or more patient IgG alloantibody/donor red blood cell antigen complexes from the patient blood/donor red blood cell mixture, optionally wherein the separating step comprises centrifugation; and
g) determining the presence or absence of one or more patient IgG alloantibodies in the patient blood sample that specifically bind to one or more red blood cell antigens expressed on the surface of the donor red blood cells, wherein agglutination of the patient antibody/donor red blood cell antigen complexes in step (e) indicates the donor blood is incompatible with the patient, and the absence of agglutination of the patient antibody/donor red blood cell antigen complexes in step (e) indicates the donor blood is compatible with the patient;
further wherein:
the patient blood sample is a plasma sample or a serum sample;
the anti-CD38 antibody is aCD38-b-348 or an antibody derived therefrom or a variant thereof;
the anti-CD38 antibody is of an IgG isotype
the anti-CD38 antibodies does not cause agglutination of the red blood cells when the anti-human IgG antibodies are added in step (e); and
the patient has been administered the anti-CD38 antibody not more than 2 months prior to obtaining the blood sample from the patient.

Aspects and embodiments described herein with the term "comprising" may include other features or steps within the scope. It is also understood that aspects and embodiments described as "comprising" also describes aspect and embodiments wherein the term "comprising" is replaced by the term "consisting essentially of" or "consisting of".

The phrase "selected from the group comprising" may be substituted with the phrase "selected from the group consisting of" and vice versa, wherever they occur herein.

It is also understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

The invention will now be further described by way of the following Examples, which are meant to serve to assist one of ordinary skill in the art in carrying out the invention and are not intended in any way to limit the scope of the invention, with reference to the Figures.

EXAMPLES

Example 1: CID103 (aCD38-b-348) Binding to CD-38 Expressing Malignant Cell Lines Materials & Methods
Cell Lines/Primary Cell Type Used.

Binding of CID103 (aCD38-b-348) to human CD38 was examined by flow cytometry using multiple human cells lines (Daudi (ATCC CCL-213), Raji (ATCC CCL-86), and Ramos (ATCC CRL-1596)) that endogenously express CD38. Daudi, Raji, Ramos and cells were cultured in log-phase in RPMI-1640 Medium (ATCC 30-2001) supplemented with 10% FCS, 2 mM L-glutamine, 100 IU/ml penicillin, 100 μg/ml streptomycin and 1 mM sodium pyruvate (all from ThermoFisher) with viability of >85% as determined by automated cell counter (Countess II FL Automated Cell Counter; ThermoFisher; catalog #AMQAF1000) prior to experiments.

Cell Staining and Flow Cytometry.

All experiments were done in triplicates using a 96-well plate format. 50,000 cells were plated in each well of a 96-well round bottom tissue culture treated plate. Following a wash step with FACS cell staining buffer (0.2% BSA, 0.02% NaN3; BioLegend, catalog #420201), cells were incubated in a 7-point 3-fold dilution series of CID103 (aCD38-b-348), daratumumab or human IgG1 isotype control (0.03, 0.08, 0.24, 0.74, 2.2, 6.6, and 20 μg/ml) for 30 minutes on ice. Following a wash step with FACS cell staining buffer, cells were incubated with secondary antibody (rabbit anti-human Fcγ F(ab')2 labeled with Alexa Fluor647; Jackson ImmunoResearch Catalog #309-606-008) at 5 μg/ml for 30 minutes on ice in the dark. Cells were washed once more with FACS cell staining buffer and analyzed by flow cytometry using a BD Biosciences FACSCalibur flow cytometer (San Jose, Calif.). FSC vs SSC gating was used to identify cells of interest. A total of 3,000 live single cells were recorded for each sample and corresponding fluorescent signal intensity histograms were analyzed. The mean fluorescence intensity (MFI) was calculated using FlowJo analysis software (Ashland, Oreg.) for each antibody concentration.

$EC_{50}$ calculations. To calculate $EC_{50}$ values, the MFI was plotted against antibody concentration (semi-log graph) and the data were fitted to a non-linear regression curve using GraphPad Prism 8 Software (La Jolla, Calif.).

Results

The $EC_{50}$ and maximum MFI values for CID103 (aCD38-b-348) and daratumumab binding to Daudi, Raji, and Ramos cell lines are shown in Table 1 below. The $EC_{50}$ and maximum MFI values for the IgG1 isotype control (negative control) are also included.

TABLE 1

EC50 (ng/mL) and maximal MFI Values for CID103 (aCD38-b-348) binding to Daudi, Raji, and Ramos cells. CD38 Binding EC50 values were generated from non-linear regression curve analysis using GraphPad Prism software.

| Cell Line | Antibody | EC50 (ng/mL) | Max MFI |
|---|---|---|---|
| Daudi | CID103 (aCD38-b-348) | 382 | 3242 |
| | Daratumumab | 166 | 2994 |
| | IgG1 isotype control | n/a | 7 |
| Raji | CID103 (aCD38-b-348) | 273 | 1198 |
| | Daratumumab | 152 | 1225 |
| | IgG1 isotype control | n/a | 5 |
| Ramos | CID103 (aCD38-b-348) | 412 | 2106 |
| | Daratumumab | 199 | 2009 |
| | IgG1 isotype control | ~1 | 5 |

"~" indicates ambiguous regression curves from which values were determined.

Figure 2:
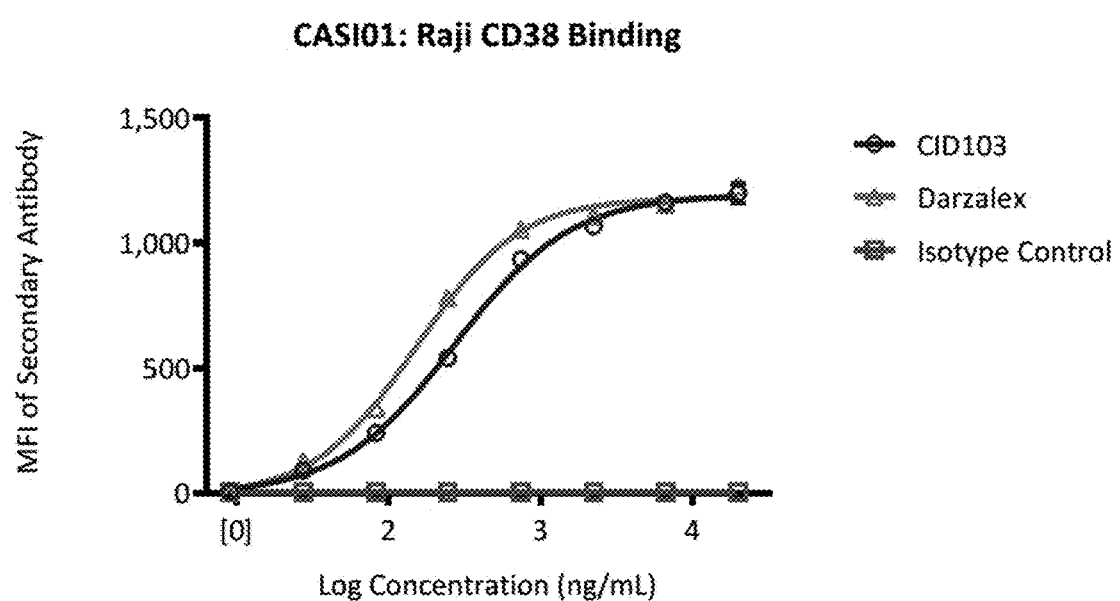
FIG. 2: Dose-response curve of CID103 (aCD38-b-348) binding to Raji cells Raji cells were incubated with various concentrations of the anti-CD38 antibodies CID103 or daratumumab (Darzalex) and binding was detected with an Alexa-647-conjugated F(ab')2 secondary antibody. An isotype control human IgG1 mAb was used as a negative control. Each data point is presented as mean value from triplicates, error bars represent SEM.
Figure 3:
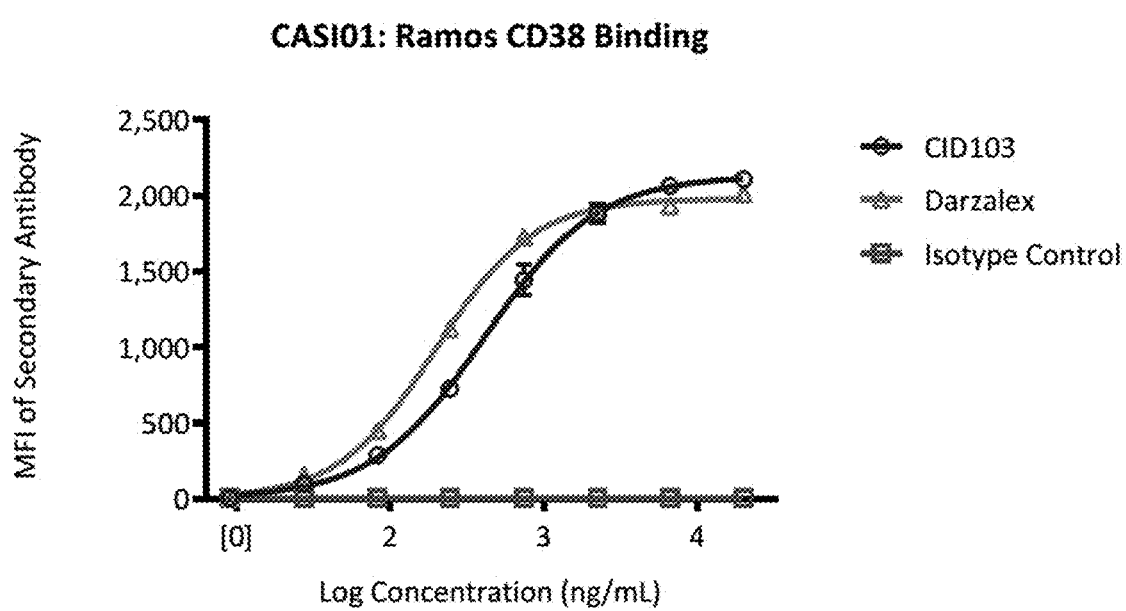
FIG. 3: Dose-response curve of CID103 (aCD38-b-348) binding to Ramos cells Ramos cells were incubated with various concentrations of the anti-CD38 antibodies CID103 or daratumumab (Darzalex) and binding was detected with an Alexa-647-conjugated F(ab')2 secondary antibody. An isotype control human IgG1 mAb was used as a negative control. Each data point is presented as mean value from triplicates, error bars represent SEM.

The dose-response curves for binding to Daudi, Raji and Ramos cell lines are shown in FIG. 1, FIG. 2 and FIG. 3 respectively.

Daratumumab showed a typical dose-response binding curve to Daudi, Raji, and Ramos cells. CID103 (aCD38-b-348) exhibits a similar saturable concentration-dependent binding with all three cell lines. The CID103 EC50 values are 382 ng/ml (Daudi cells), 373 ng/ml (Raji cells), and 412 ng/ml (Ramos cells) and are slightly higher than the EC50 values of daratumumab (166-199 ng/ml). Maximal binding of CID103 (aCD38-b-348) to tested cells was similar to (for Raji cells) or slightly higher than (for Daudi and Ramos cells) daratumumab binding. The IgG1 isotype control did not demonstrate binding on any of the tested cell lines.

Example 2: CID-103 Binding to Donor RBCs

Materials & Methods

Primary Cell Types Used.

Binding of CID103 (aCD38-b-348) to human red blood cells was examined by flow cytometry using fresh whole human blood from three (3) normal healthy donors. Fresh heparinized whole blood was obtained from sites approved by the Institutional Review Board for Human Participants (IRB) for the collection of tissues for in vitro research purposes. Whole blood was visually inspected for haemolysis prior to experiments.

Preparation of Donor RBCs.

The whole blood was centrifuged and washed with 1×PBS three times prior to usage. Washed whole blood was diluted 1:20 to make a 5% erythrocytes suspension with PBS (hereafter referred to as blood substrate). Blood substrate was used for assay within 3 hours of preparation.

Cell Staining and Flow Cytometry.

100 μl of blood substrate mixed with 100 μl of FACS buffer was plated per well on 96-well round bottom tissue culture treated plate and incubated with a 7-point 3-fold dilution series (0.03, 0.08, 0.24, 0.74, 2.2, 6.6, and 20 μg/ml) of either CID103 (aCD38-b-348), Human IgG1 Isotype control antibody (BioXcell; Catalog #BE0297), daratumumab (Darzalex) or Alexa Fluor 647-labeled CD47 antibody (BioLegend; Catalog #323118) for 30 minutes on ice. Each condition was performed in triplicate. Following a wash step with FACS Buffer, samples were incubated with secondary Alexa Fluor 647-labeled goat anti-human Fcγ F(ab')2 antibody (Jackson ImmunoResearch; Catalog #109-606-170) at 5 μg/ml for 30 minutes on ice in the dark. Samples were washed once more with FACS Buffer to remove unbound secondary antibody and analyzed by flow cytometry using an Intellicyt flow cytometer. Samples incubated with Alexa Fluor 647-labeled CD47 antibody were processed for flow cytometry analysis without incubation with secondary antibody. FSC vs SSC gating was used to identify red blood cells. At least 3,000 live red blood cells were collected for each sample and corresponding fluorescent signal intensity histograms were analyzed. The mean fluorescence intensity (MFI) was determined using ForeCyt analysis software for each antibody concentration.

$EC_{50}$ Calculations.

To calculate $EC_{50}$ values, the MFI was plotted against antibody concentration (semi-log graph) and the data were fitted to a non-linear regression curve using GraphPad Prism 8 Software (La Jolla, Calif.).

Results

The $EC_{50}$ and maximum MFI values for CID103 (aCD38-b-348) and daratumumab binding to RBCs from each of the three donors are shown in Table 2 below. The $EC_{50}$ and maximum MFI values for the IgG1 isotype control (negative control) and anti-human CD47 (positive control) are also included.

TABLE 2

| Antibody | Donor | EC50 (ng/mL) | Max MFI |
|---|---|---|---|
| CID103 (aCD38-b-348) | 1 | N/A | 4994 |
| | 2 | N/A | 3452 |
| | 3 | N/A | 3110 |

TABLE 2-continued

| Antibody | Donor | EC50 (ng/mL) | Max MFI |
|---|---|---|---|
| Daratumumab | 1 | N/A | 7790 |
| | 2 | N/A | 5226 |
| | 3 | N/A | 5053 |
| IgG1 isotype control | 1 | N/A | 2562 |
| | 2 | N/A | 2114 |
| | 3 | N/A | 1959 |
| Anti-human CD47 | 1 | 1913 | *107419 |
| | 2 | 2107 | *112755 |
| | 3 | 2127 | *130744 |

*directly conjugated antibody

The dose-response curves for binding to RBCs from each of the three donors are shown in FIGS. 4, 5 and 6.

Summary

Daratumumab showed a dose-dependent increase in binding with RBCs from all three donors. CID103 (aCD38-b-348) showed a dose-dependent increase in binding with RBCs from all three donors, but with lower overall MFI values compared to daratumumab. The IgG1 isotype control did not demonstrate binding to RBCs from any of the three donors, except at the highest concentration tested. The positive control, AF647 conjugated anti-human CD47, showed a dose-response binding curve with RBCs from all three donors.

Example 3: Pre-Transfusion Testing of CID103 (aCD38-b-348) and Daratumumab by IAT Tube Method Materials & Methods
Sample Preparation.

CID103 (aCD38-b-348) and daratumumab were prepared at concentrations of 250 ug/ml and 1000 ug/ml in inert AB plasma. Samples of AB plasma only were used as a control.

RBCs.

RBCs having the following Rh phenotypes were used: RhD positive (R1R1, R2R2) and RhD negative (rr). RBCs were prepared from whole blood samples according to standard protocols.

IAT Tube Method Protocol.

RBCs were incubated in polyethylene glycol (PEG) enhancement media with anti-human globulin (Ortho Diagnostics) and CID103 (aCD38-b-348), daratumumab or control plasma according to standard protocols.

Data Analysis.

After incubation, tubes were visually assessed by trained personnel at the New York Blood Center, and graded on a scale of 4+ to 0 for the level of reactivity observed, where 4+, 3+, 2+ and 1+ all indicate reactivity and 0 or 0? indicate no or questionable reactivity. Reactivity observed in any of the experiments indicates interference by the anti-CD38 antibody present in the sample.

Results

The results are shown in Table 3.

TABLE 3

| RBC Rh phenotype | CID103 (aCD38-b-348) ug/ml | | Daratumumab (ug/ml) | Plasma only (negative control) |
|---|---|---|---|---|
| | 250 | 1000 | 250 | N/A |
| R1R1 | 0 | 0 | 1+ | 0 |
| R2R2 | 0 | 0 | 1+ | 0 |
| rr | 0 | 0 | 1+ | 0 |

Summary.

Daratumumab exhibited a reading of 1+ for every RBC phenotype tested, whilst CID103 (aCD38-b-348) did not result in any detectable interference even at high concentrations of 1000 ug/ml. In a blood bank setting, a reading of 1+ would indicate an incompatible match between donor and recipient. Therefore, whilst treatment of a patient with daratumumab may falsely indicate incompatibility between recipient and donor RBCs, treatment of a patient with CID103 (aCD38-b-348) would not be expected to cause such interference.

Example 4: Pre-Transfusion Testing of CID103 (aCD38-b-348) and Daratumumab on Untreated RBCs Using Column Agglutination Technology Materials & Methods
Sample Preparation.

CID103 (aCD38-b-348) and daratumumab were prepared at concentrations of 1 ug/ml, 10 ug/ml, 100 ug/ml and 250 ug/ml in inert AB plasma. Additional samples of CID103 (aCD38-b-348) were prepared at concentrations of 625 ug/ml and 1000 ug/ml in inert AB plasma. Samples of inert AB plasma only were used as a control.

RBCs.

RBCs having the following Rh phenotypes were used: RhD positive (R1R1, R2R2) and RhD negative (rr). RBCs were prepared from whole blood sample according to standard protocols.

Column Agglutination Technology.

IgG gel cards were obtained from Ortho MTS. RBCs were incubated with CID103(aCD38-b-348), daratumumab or control plasma according to manufacturer's instructions. Following incubation, samples were centrifuged for 10 minutes at 900 rpm, according to manufacturer's instructions.

Data Analysis.

After centrifugation, tubes were visually assessed by trained personnel at the New York Blood Center, and graded on a scale of 4+ to 0 for the level of reactivity observed, where 4+, 3+, 2+ and 1+ all indicate reactivity and 0 or 0? indicate no or questionable reactivity. φ indicates no drug present in the sample (plasma control). Reactivity observed in any of the experiments indicates interference by the anti-CD38 antibody present in the sample.

Results

Gel card results for CID103 (aCD38-b-348) and daratumumab at each of the concentrations tested are shown in FIGS. 7A-C and 8A-D.

Figure 8A:
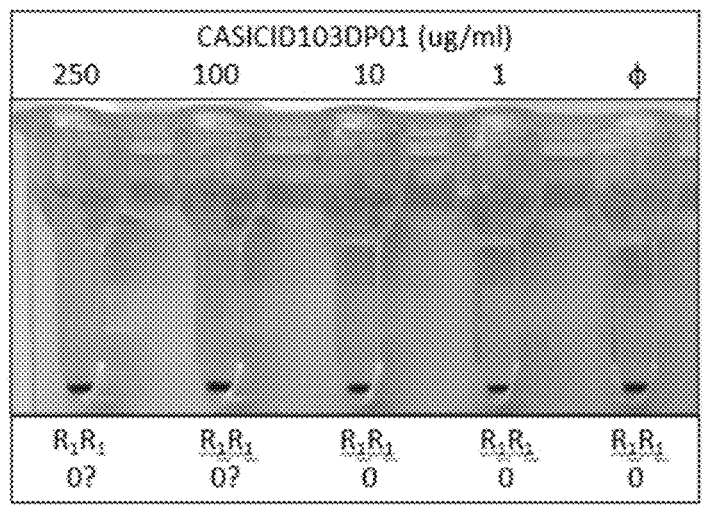
FIGS. 8A-D show the results at each concentration tested and for each Rh phenotype. Daratumumab concentration is indicated above each microtube, ϕ indicates no drug is present. Rh phenotype is indicated below each microtube. IgG gel cards were scored by trained personnel according to the degree of agglutination observed, with 4+, 3+, 2+ and 1+ all indicating the presence of an agglutination reaction. A rating of 0 or 0? indicates no agglutination or questionable agglutination. Agglutination ratings are shown below each microtube.
Figure 8B:
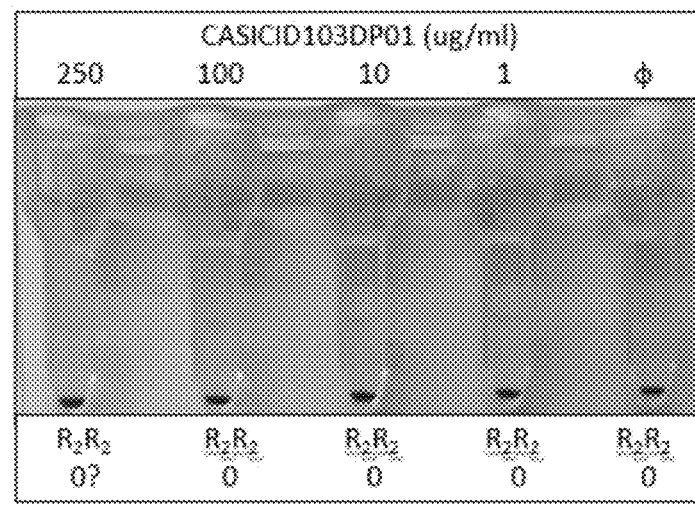
Figure 8C:
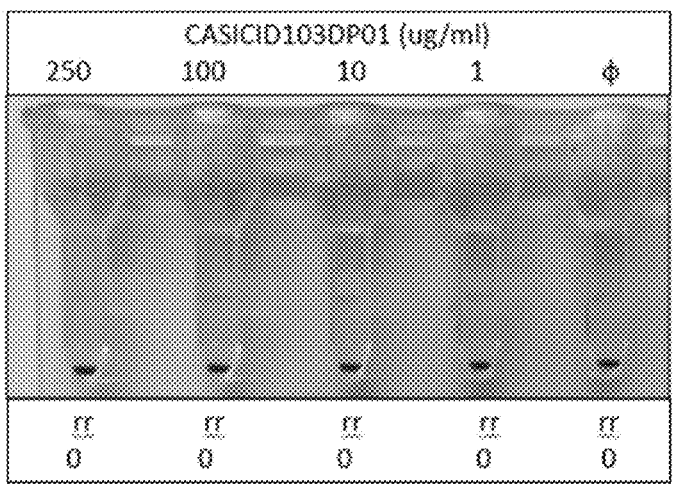
Figure 8D:
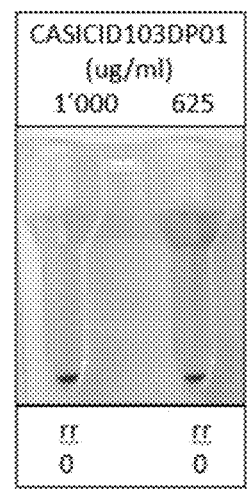
Figure 9A:
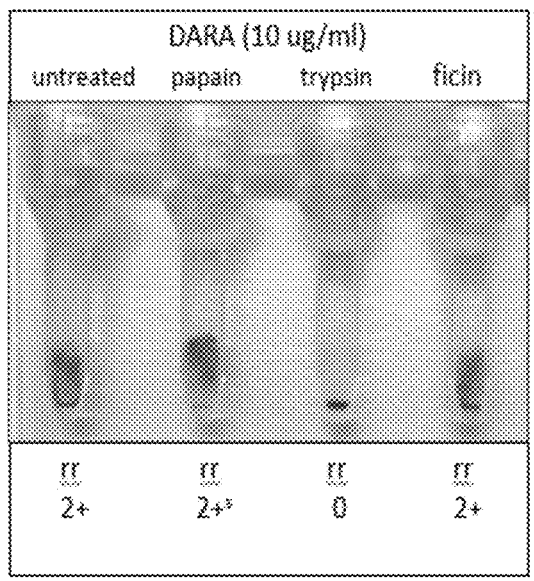
FIGS. 9A-D show the results at each concentration tested and for each RBC treatment condition. RBC treatment is indicated above each microtube. IgG gel cards were scored by trained personnel according to the degree of agglutination observed, with 4+, 3+, 2+ and 1+ all indicating the presence of an agglutination reaction. A rating of 0 or +/− indicates no agglutination or questionable agglutination. Agglutination ratings are shown below each microtube.
Figure 9B:
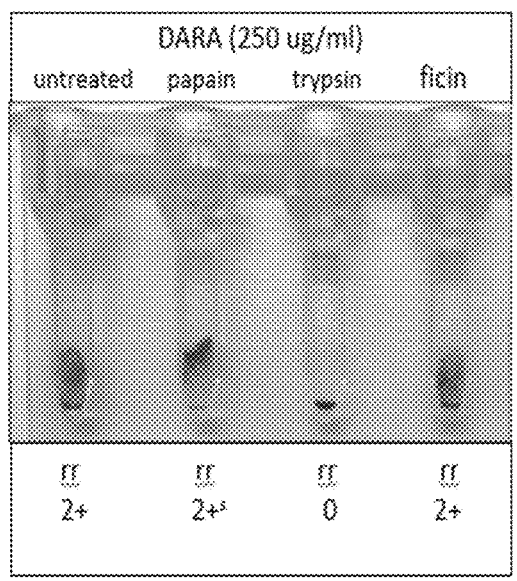
Figure 9C:
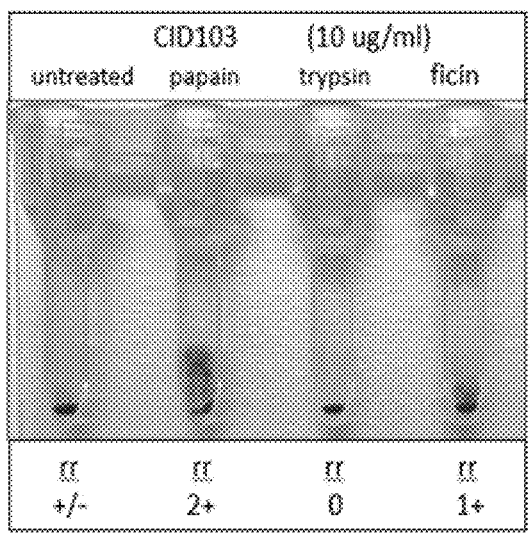
Figure 9D:
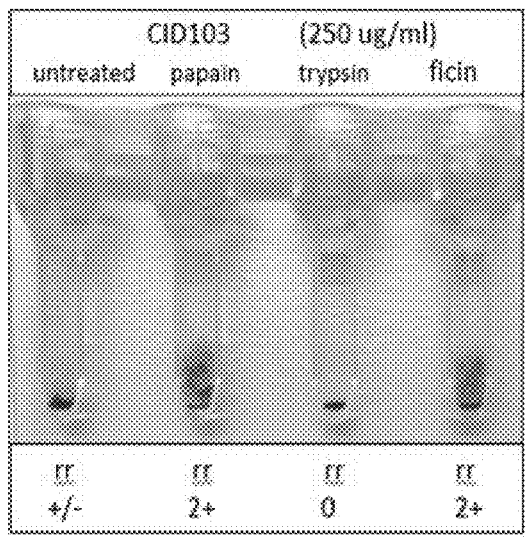

As can be seen from FIGS. 7A-C, daratumumab robustly caused interference between 1+ and 2+, even at low concentrations of 1 ug/l. Interference was seen for daratumumab for all the RBC Rh phenotypes tested. In contrast, as can be seen from FIGS. 8A-D, CID103 (aCD38-b-348) caused minimal interference, with questionable interference only detected at higher concentrations of 100 and 250 ug/ml in the Rh positive RBCs tested. No interference at all was observed for the Rh negative RBCs, even at very high concentrations of 625 and 1000 ug/ml (FIG. 8D).

Example 5: Pre-Transfusion Testing of CID103 (aCD38-b-348) and Daratumumab on Enzyme or DTT-Treated RBCs Using Column Agglutination Technology Materials & Methods
Sample Preparation.

CID103 (aCD38-b-348) and daratumumab were prepared at concentrations of 10 ug/ml and 250 ug/ml in inert AB plasma. Samples of inert AB plasma only were used as a control.

RBCs.

RBCs having an RhD negative (rr) phenotype were used. RBCs were prepared from whole blood samples according to standard protocols. Both untreated and pre-treated RBCs were used. For pre-treated RBCs, RBCs were treated with commercially prepared ficin according to manufacturer's instructions, or with in-house prepared papain, trypsin or 0.2M DTT as described by Judd, Johnson & Storry (2008) *Judd's Methods in Immunohematology* 3$^{rd}$ Ed.

Column Agglutination Technology.

IgG gel cards were obtained from Ortho MTS. RBCs were incubated with CID103 (aCD38-b-348), daratumumab or control plasma according to manufacturer's instructions. Following incubation, samples were centrifuged for 10 minutes at 900 rpm, according to manufacturer's instructions.

Data Analysis.

After centrifugation, tubes were visually assessed by trained personnel at the New York Blood Center, and graded on a scale of 4+ to 0 for the level of reactivity observed, where 4+, 3+, 2+ and 1+ all indicate reactivity and 0 or +/− indicate no or questionable reactivity. φ indicates no drug present in the sample (plasma control). Reactivity observed in any of the experiments indicates interference by the anti-CD38 antibody present in the sample.

Results

Gel card results for plasma containing daratumumab or CID103 (aCD38-b-348) with untreated RBCs or with RBCs treated with papain, trypsin or ficin are shown in FIG. 9.

For untreated RBCs, as previously demonstrated daratumumab causes robust interference of 2+ at both 10 and 250 ug/ml, whilst CID103 (aCD38-b-348) resulted in minimal interference at both concentrations tested. Treatment of RBCs with papain and ficin does not resolve the observed daratumumab interference at either concentration. Treatment of RBCs with papain and ficin causes interference to be observed on CID103 (aCD38-b-348) samples.

Treatment of RBCs with trypsin resolves the interference seen at both 10 and 250 ug/ml of daratumumab. No interference was observed with CID103 (aCD38-b-348) on trypsin-treated RBCs.

Treatment of RBCs with DTT also resolved the interference seen at both 10 and 250 ug/ml of daratumumab. No interference was observed with CID103 (aCD38-b-348) on DTT-treated RBCs.

Example 6: Pre-Transfusion Testing of CID103 (aCD38-b-348) Using Automated Platforms Materials & Methods CID103 (aCD38-b-348) was prepared at a concentration of 250 ug/ml in inert AB plasma. RBCs were prepared from whole blood samples according to standard protocols. Samples were run on two different automated analysers, IH-1000 (BioRad) and Tango (BioRad), according to manufacturer's instructions.

Results

Figure 10:
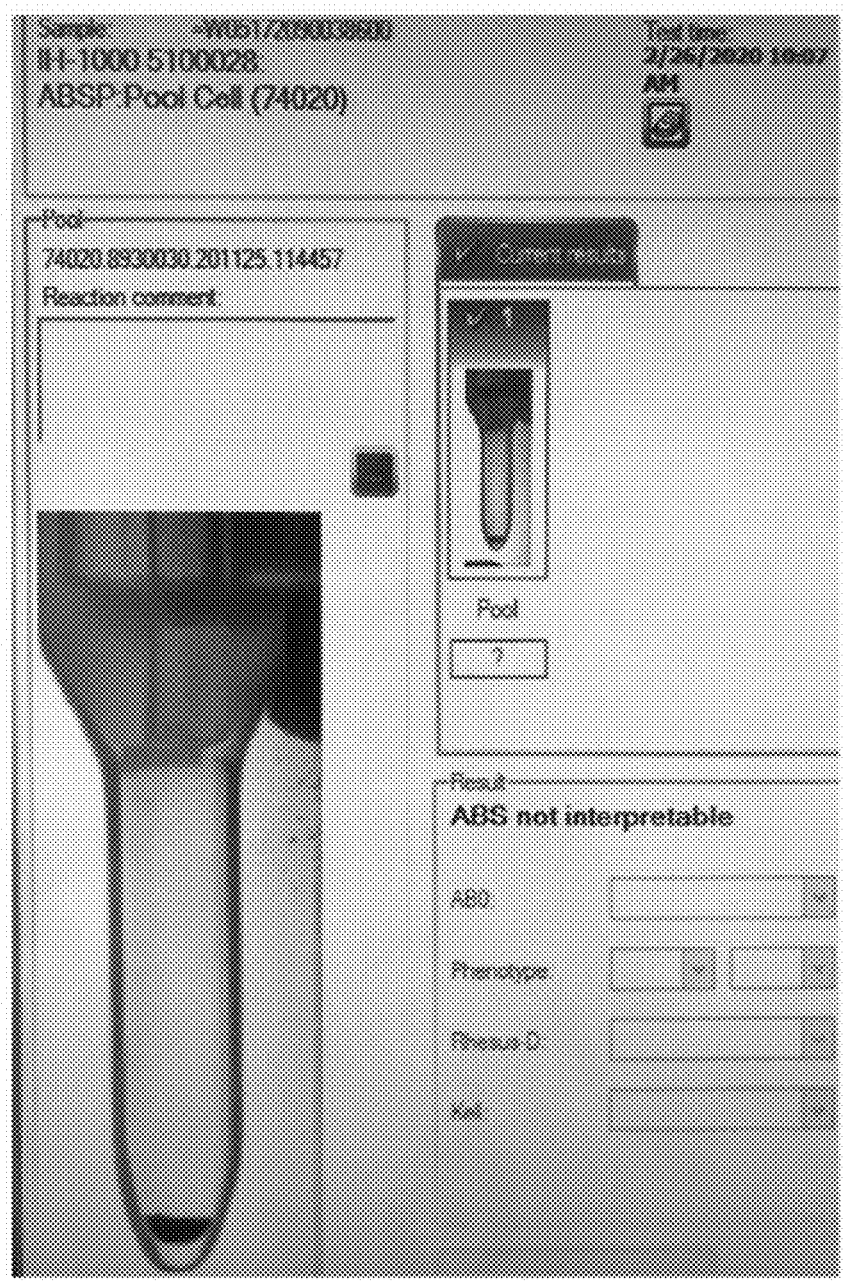
FIG. 10: Screening of CID103 (aCD38-b-348) with untreated RBCs on the automated platform IH-1000 Untreated RBCs were incubated with 250 ug/ml of CID103 (aCD38-b-348) in inert AB plasma and assayed for interference (i.e. the presence of an agglutination reaction despite no clinically significant alloantibodies being present in the sample) using the automated IH-1000 platform (BioRad).

No reactivity was detected using CID103 (aCD38-b-348) at 250 ug/ml on the Tango (BioRad) automated platform. The IH-1000 platform (BioRad) returned an undetermined result, as can be seen in FIG. 10. In accordance with standard protocols this result was evaluated by trained personnel and was reported as non-reactive.

Example 7: Amino Acid Sequences

The present disclosure makes reference to a number of different amino acid sequences, as follows:

| SEQ ID NO | Description of sequence | Sequence |
| --- | --- | --- |
| 1 | CD38-b-348-HCDR1 | GSISSSDYYWG |
| 2 | aCD38-b-348-HCDR2 | SIYYSGSTYYNPSLKS |
| 3 | aCD38-b-348-HCDR3 | ARGQYSSGWYAYPFDM |
| 4 | aCD38-b-348-LCDR1 | RASQSVRSSYLA |
| 5 | aCD38-b-348-LCDR2 | GASSRAT |
| 6 | aCD38-b-348-LCDR3 | QQDGNVYT |
| 7 | aCD38-b-348 VH (also aCD38-b-348-m1 VH, aCD38-b-348-m2 VH, aCD38-b-348-m3 VH, aCD38-b-348-m4 VH) | QLQLQESGPGLVKPSETLSLTCTVSGGSISSSDYYWGWIR QPPGKGLEWIGSIYYSGSTYYNPSLKSRVTISVDTSKNQF SLKLSSVTAADTAVYYCARGQYSSGWYAYPFDMWGQGTMV TVSS |
| 8 | aCD38-b-348 VL | EIVLTQSPGTLSLSPGERATLSCRASQSVRSSYLAWYQQK PGQAPRLLIYGASSRATGIPDRFSGSGSGTDFTLTISRLE PEDFAVYYCQQDGNVYTFGGGTKVEIK |
| 9 | aCD38-b-348-m1 - LCDR3 | QQEANVYT |
| 10 | aCD38-b-348-m2 - LCDR3 | QQDSNVYT |
| 11 | aCD38-b-348-m3 - LCDR3 | QQDANVYT |

| SEQ ID NO | Description of sequence | Sequence |
|---|---|---|
| 12 | aCD38-b-348-m4 - LCDR3 | QQEGNVYT |
| 13 | aCD38-b-348-m1 VL | EIVLTQSPGTLSLSPGERATLSCRASQSVRSSYLAWYQQK PGQAPRLLIYGASSRATGIPDRFSGSGSGTDFTLTISRLE PEDFAVYYCQQEANVYTFGGGTKVEIK |
| 14 | aCD38-b-348-m2 VL | EIVLTQSPGTLSLSPGERATLSCRASQSVRSSYLAWYQQK PGQAPRLLIYGASSRATGIPDRFSGSGSGTDFTLTISRLE PEDFAVYYCQQDSNVYTFGGGTKVEIK |
| 15 | aCD38-b-348-m3 VL | EIVLTQSPGTLSLSPGERATLSCRASQSVRSSYLAWYQQK PGQAPRLLIYGASSRATGIPDRFSGSGSGTDFTLTISRLE PEDFAVYYCQQDANVYTFGGGTKVEIK |
| 16 | aCD38-b-348-m4 VL | EIVLTQSPGTLSLSPGERATLSCRASQSVRSSYLAWYQQK PGQAPRLLIYGASSRATGIPDRFSGSGSGTDFTLTISRLE PEDFAVYYCQQEGNVYTFGGGTKVEIK |
| 17 | aCD38-b-329-HCDR1 | GSISSSDYYWG |
| 18 | aCD38-b-329-HCDR2 | SIYYSGSTYYNPSLKS |
| 19 | aCD38-b-329-HCDR3 | ARGQYSSGWYAYPFDM |
| 20 | aCD38-b-329-LCDR1 | RASQSVRSSYLA |
| 21 | aCD38-b-329-LCDR2 | GASSRAT |
| 22 | aCD38-b-329-LCDR3 | QQDGAVFT |
| 23 | aCD38-b-329 VH (also aCD38-b-329-m6 VH and aCD38-b-329-m7 VH) | QLQLQESGPGLVKPSETLSLTCTVSGGSISSSDYYWGWIR QPPGKGLEWIGSIYYSGSTYYNPSLKSRVTISVDTSKNQF SLKLSSVTAADTAVYYCARGQYSSGWYAYPFDMWGQGTMV TVSS |
| 24 | aCD38-b-329 VL | EIVLTQSPGTLSLSPGERATLSCRASQSVRSSYLAWYQQK PGQAPRLLIYGASSRATGIPDRFSGSGSGTDFTLTISRLE PEDFAVYYCQQDGAVFTFGGGTKVEIK |
| 25 | aCD38-b-329-m6 - LCDR3 | QQDEAVFT |
| 26 | aCD38-b-329-m7 - LCDR3 | QQDSAVFT |
| 27 | aCD38-b-329-m6 VL | EIVLTQSPGTLSLSPGERATLSCRASQSVRSSYLAWYQQK PGQAPRLLIYGASSRATGIPDRFSGSGSGTDFTLTISRLE PEDFAVYYCQQDEAVFTFGGGTKVEIK |
| 28 | aCD38-b-329-m7 VL | EIVLTQSPGTLSLSPGERATLSCRASQSVRSSYLAWYQQK PGQAPRLLIYGASSRATGIPDRFSGSGSGTDFTLTISRLE PEDFAVYYCQQDSAVFTFGGGTKVEIK |
| 29 | Human CD38 | MANCEFSPVSGDKPCCRLSRRAQLCLGVSILVLILVVVLA VVVPRWRQQWSGPGTTKRFPETVLARCVKYTEIHPEMRHV DCQSVWDAFKGAFISKHPCNITEEDYQPLMKLGTQTVPCN KILLWSRIKDLAHQFTQVQRDMFTLEDTLLGYLADDLTWC GEFNTSKINYQSCPDWRKDCSNNPVSVFWKTVSRRFAEAA CDVVHVMLNGSRSKIFDKNSTFGSVEVHNLQPEKVQTLEA WVIHGGREDSRDLCQDPTIKELESIISKRNIQFSCKNIYR PDKFLQCVKNPEDSSCTSEI |
| 30 | Epitope (aCD38-b-ep) | ARCVKYTEIHPEMRH |
| 31 | Daratumumab heavy chain | EVQLLESGGGLVQPGGSLRLSCAVSGFTFNSFAMSWVRQA PGKGLEWVSAISGSGGGTYYADSVKGRFTISRDNSKNTLY LQMNSLRAEDTAVYFCAKDKILWFGEPVFDYWGQGTLVTV SSASTKGPSVFPLAPSSKSTSGGTAALGCLVKDYFPEPV TVSWNSGALTSGVHTFPAVLQSSGLYSLSSVVTVPSSSLG TQTYICNVNHKPSNTKVDKRVEPKSCDKTHTCPPCPAPEL LGGPSVFLFPPKPKDTLMISRTPEVTCVVVDVSHEDPEVK FNWYVDGVEVHNAKTKPREEQYNSTYRVVSVLTVLHQDW LNGKEYKCKVSNKALPAPIEKTISKAKGQPREPQVYTLPP SREEMTKNQVSLTCLVKGFYPSDIAVEWESNGQPENNYKT TPPVLDSDGSFFLYSKLTVDKSRWQQGNVFSCSVMHEALH NHYTQKSLSLSPGK |

| SEQ ID NO | Description of sequence | Sequence |
|---|---|---|
| 32 | Daratumumab light chain | EIVLTQSPATLSLSPGERATLSCRASQSVSSYLAWYQQKP GQAPRLLIYDASNRATGIPARFSGSGSGTDFTLTISSLEP EDFAVYYCQQRSNWPPTFGQGTKVEIKRTVAAPSVFIFPP SDEQLKSGTASVVCLLNNFYPREAKVQWKVDNALQSGNS QESVTEQDSKDSTYSLSSTLTLSKADYEKHKVYACEVTHQ GLSSPVTKSFNRGEC |
| 33 | Isatuximab heavy chain | QVQLVQSGAEVAKPGTSVKLSCKASGYTFTYWMQWVKQRP GQGLEWIGTIYPGDGDTGYAQKFQGKATLTADKSSKTVYM HLSSLASEDSAVYYCARGDYYGSNSLDYWGQGTSVTVSSA STKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKKVEPKSCDKTHTCPPCPAPELLGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSRDE LTKNQVSLTCLVKGFYPSDIAVEWESNGQPENNYKTTPPV LDSDGSFFLYSKLTVDKSRWQQGNVFSCSVMHEALHNHYT QKSLSLSPGK |
| 34 | Isatuximab light chain | DIVMTQSHLSMSTSLGDPVSITCKASQDVSTVVAWYQQKP GQSPRRLIYSASYRYIGVPDRFTGSGAGTDFTFTISSVQA EDLAVYYCQQHYSPPYTFGGGTKLEIKRTVAAPSVFIFPP SDEQLKSGTASVVCLLNNFYPREAKVQWKVDNALQSGNSQ ESVTEQDSKDSTYSLSSTLTLSKADYEKHKVYACEVTHQG LSSPVTKSFNRGEC |

EQUIVALENTS AND SCOPE

Those skilled in the art will appreciate that the present invention is defined by the appended claims and not by the Examples or other description of certain embodiments included herein.

Similarly, the singular forms "a", "an", and "the" include plural referents unless the context clearly dictates otherwise.

Unless defined otherwise above, all technical and scientific terms used herein have the same meaning as commonly understood by one of ordinary skill in the art to which this invention belongs. Any methods and materials similar or equivalent to those described herein can also be used in the practice or testing of the present invention. Generally, nomenclatures used in connection with, and techniques of, cell and tissue culture, molecular biology, immunology, genetics and protein and nucleic acid chemistry described herein are those well known and commonly used in the art, or according to manufacturer's specifications.

All publications mentioned herein are incorporated herein by reference to disclose and describe the methods and/or materials in connection with which the publications are cited.

REFERENCES

Chevrier S et al. 2017. Cell. 169:736-749
Darzalex package insert. Horsham Pa.: Janssen Biotech, 2015
Ellington et al. Nature. 1990; 346(6287): 818-822
Handbook of Therapeutic Antibodies, Wiley, 2014, Chapter 6, Antibody Affinity (pages 115-140)
Hendrickson & Tormey, 2016, Hematol Oncol Clin N Am, 30:635-651
Jarasch A et al., 2015. J Pharm Sci. 104:1885-1898
Judd, Johnson & Storry (2008) Judd's Methods in Immunohematology 3rd Ed.
Kearns J D et al., 2015. Mol Cancer Ther. 14:1625-36
Kijanka M et al., 2015. Nanomedicine. 10:161-174.
Liu L, 2015. J Pharm Sci. 104:1866-84.
Ni et al., Curr Med Che 2011; 18(27):4206-14
Oostendorp et al. 2015, Transfusion, 55:1555-62
Rajpal et al., Proc Natl Acad Sci USA, 2005, 102(24):8466-71
Redman J M et al., 2015. Mol Immunol. 67: 28-45.
Regan & Markowitz, 2016, American Association of Blood Banks, Bulletin #16-02
Sliwkowski M & Mellman I, 2013. Science. 341:1192-8.
Steinwand et al., MAbs, 2014, 6(1):204-18
Tormey & Hendrickson, 2019, Blood, 133:1821-1830
Tuerk et al., Science. 1990; 249(4968):505-510
Vazquez-Lombardi R et al., 2015. Drug Discov Today. 20:1271-83

CLAUSES

The invention includes at least the following numbered clauses:

1. A method of screening a blood sample obtained from a patient, wherein the patient has been administered an anti-CD38 antibody or antigen binding fragment thereof, the method comprising:
   a) providing a blood sample from the patient;
   b) providing a blood sample from a donor, wherein the donor blood sample comprises donor red blood cells; and
   c) screening the patient blood sample, comprising determining the presence or absence of one or more patient antibodies in the patient blood sample that specifically bind to one or more red blood cell antigens expressed on the surface of the donor red blood cells.
2. The method of clause 1, wherein the method does not comprise a step of contacting the patient blood sample or the donor blood sample with an agent that inhibits binding of the anti-CD38 antibody or antigen binding fragment thereof to membrane-bound CD38 present on the surface of the one or more donor red cells.

3. The method of clause 2, wherein the agent that inhibits binding of the anti-CD38 antibody or antigen binding fragment thereof to membrane-bound CD38 present on the surface of the one or more donor red cells is a soluble CD38 antigen, an anti-CD38 idiotype antibody, or an antigen-stripping agent.
4. The method of clause 3, wherein the antigen-stripping agent is a redox reagent or an enzyme.
5. The method of clause 4, wherein the redox reagent is DTT.
6. The method of clause 4, wherein the enzyme is a protease.
7. The method of clause 6, wherein the protease is selected from the group consisting of trypsin, alpha chymotrypsin, papain, and ficin.
8. The method of any preceding clause, wherein the anti-CD38 antibody or antigen binding fragment thereof specifically binds to an epitope of human CD38, wherein the epitope comprises one or more amino acid residues comprised in amino acids 65-79 of SEQ ID NO: 29 (human CD38).
9. The method of any preceding clause, wherein the anti-CD38 antibody or antigen binding fragment thereof specifically binds to an epitope of human CD38, wherein the epitope comprises amino acids 65-79 of SEQ ID NO: 29 (human CD38).
10. The method of any preceding clause, wherein the anti-CD38 antibody or antigen binding fragment thereof comprises an HCDR3 comprising the amino acid sequence of SEQ ID NO: 3 or SEQ ID NO: 19.
11. The method of any preceding clause, wherein the anti-CD38 antibody or antigen binding fragment thereof comprises:
    a) an HCDR1 comprising the amino acid sequence SEQ ID NO: 1;
       an HCDR2 comprising the amino acid sequence SEQ ID NO: 2;
       an HCDR3 comprising the amino acid sequence SEQ ID NO: 3;
       an LCDR1 comprising the amino acid sequence SEQ ID NO: 4;
       an LCDR2 comprising the amino acid sequence SEQ ID NO: 5; and
       an LCDR3 comprising an amino acid sequence selected from the group consisting of SEQ ID NOs: 6, 9, 10, 11 and 12; or
    b) an HCDR1 comprising the amino acid sequence of SEQ ID NO: 17;
       an HCDR2 comprising the amino acid sequence of SEQ ID NO: 18;
       an HCDR3 comprising the amino acid sequence of SEQ ID NO: 19;
       an LCDR1 comprising the amino acid sequence of SEQ ID NO: 20;
       an LCDR2 comprising the amino acid sequence of SEQ ID NO: 21; and
       an LCDR3 comprising an amino acid sequence selected from the group consisting of SEQ ID NO: 22, 25 and 26.
12. The method of any preceding clause, wherein the anti-CD38 antibody or antigen binding fragment thereof comprises:
    a) an HCDR1 comprising the amino acid sequence of SEQ ID NO: 1;
       an HCDR2 comprising the amino acid sequence of SEQ ID NO: 2;
       an HCDR3 comprising the amino acid sequence of SEQ ID NO: 3;
       an LCDR1 comprising the amino acid sequence of SEQ ID NO: 4;
       an LCDR2 comprising the amino acid sequence of SEQ ID NO: 5; and
       an LCDR3 comprising the amino acid sequence of SEQ ID NOs: 6; or
    b) an HCDR1 comprising the amino acid sequence of SEQ ID NO: 17
       an HCDR2 comprising the amino acid sequence of SEQ ID NO: 18;
       an HCDR3 comprising the amino acid sequence of SEQ ID NO: 19;
       an LCDR1 comprising the amino acid sequence of SEQ ID NO: 20;
       an LCDR2 comprising the amino acid sequence of SEQ ID NO: 21; and
       an LCDR3 comprising the amino acid sequence of SEQ ID NO: 22.
13. The method of any preceding claim, wherein the anti-CD38 antibody or antigen binding fragment thereof comprises:
    a) a variable light chain comprising an amino acid sequence having at least 90%, at least 95%, at least 98% or at least 99% identity to SEQ ID NO: 7 and/or a variable heavy chain comprising an amino acid sequence having at least 90%, at least 95%, at least 98% or at least 99% identity to SEQ ID NO: 8;
    b) a variable light chain comprising an amino acid sequence having at least 90%, at least 95%, at least 98% or at least 99% identity to SEQ ID NO: 23 and/or a variable heavy chain comprising an amino acid sequence having at least 90%, at least 95%, at least 98% or at least 99% identity to SEQ ID NO: 24;
    c) a variable light chain comprising an amino acid sequence having at least 90%, at least 95%, at least 98% or at least 99% identity to SEQ ID NO: 7 and/or a variable heavy chain comprising an amino acid sequence having at least 90%, at least 95%, at least 98% or at least 99% identity to SEQ ID NO: 13;
    d) a variable light chain comprising an amino acid sequence having at least 90%, at least 95%, at least 98% or at least 99% identity to SEQ ID NO: 7 and/or a variable heavy chain comprising an amino acid sequence having at least 90%, at least 95%, at least 98% or at least 99% identity to SEQ ID NO: 14;
    e) a variable light chain comprising an amino acid sequence having at least 90%, at least 95%, at least 98% or at least 99% identity to SEQ ID NO: 7 and/or a variable heavy chain comprising an amino acid sequence having at least 90%, at least 95%, at least 98% or at least 99% identity to SEQ ID NO: 15;
    f) a variable light chain comprising an amino acid sequence having at least 90%, at least 95%, at least 98% or at least 99% identity to SEQ ID NO: 7 and/or a variable heavy chain comprising an amino acid sequence having at least 90%, at least 95%, at least 98% or at least 99% identity to SEQ ID NO: 16;
    g) a variable light chain comprising an amino acid sequence having at least 90%, at least 95%, at least 98% or at least 99% identity to SEQ ID NO: 23 and/or a variable heavy chain comprising an amino acid sequence having at least 90%, at least 95%, at least 98% or at least 99% identity to SEQ ID NO: 27; or h) a variable light chain comprising an amino acid sequence having at least 90%, at least 95%, at least 98% or at least 99% identity to SEQ ID NO: 23 and/or a variable heavy chain comprising an amino acid sequence having at least 90%, at least 95%, at least 98% or at least 99% identity to SEQ ID NO: 28.

14. The method of any preceding clause, wherein the anti-CD38 antibody or antigen binding fragment thereof comprises:
   a) a variable light chain comprising the amino acid sequence of SEQ ID NO: 7 or a variable light chain region sequence having up to 2 amino acid substitutions compared to SEQ ID NO: 7 and a variable heavy chain comprising the amino acid sequence of SEQ ID NO: 8 or a variable heavy chain region sequence having up to 2 amino acid substitutions compared to SEQ ID NO: 8;
   b) a variable light chain comprising the amino acid sequence of SEQ ID NO: 23 or a variable light chain region sequence having up to 2 amino acid substitutions compared to SEQ ID NO: 23 and a variable heavy chain comprising the amino acid sequence of SEQ ID NO: 24 or a variable heavy chain region sequence having up to 2 amino acid substitutions compared to SEQ ID NO: 24;
   c) a variable light chain comprising the amino acid sequence of SEQ ID NO: 7 or a variable light chain region sequence having up to 2 amino acid substitutions compared to SEQ ID NO: 7 and a variable heavy chain comprising the amino acid sequence of SEQ ID NO: 13 or a variable heavy chain region sequence having up to 2 amino acid substitutions compared to SEQ ID NO: 13;
   d) a variable light chain comprising the amino acid sequence of SEQ ID NO: 7 or a variable light chain region sequence having up to 2 amino acid substitutions compared to SEQ ID NO: 7 and a variable heavy chain comprising the amino acid sequence of SEQ ID NO: 14 or a variable heavy chain region sequence having up to 2 amino acid substitutions compared to SEQ ID NO: 14;
   e) a variable light chain comprising the amino acid sequence of SEQ ID NO: 7 or a variable light chain region sequence having up to 2 amino acid substitutions compared to SEQ ID NO: 7 and a variable heavy chain comprising the amino acid sequence of SEQ ID NO: 15 or a variable heavy chain region sequence having up to 2 amino acid substitutions compared to SEQ ID NO: 15;
   f) a variable light chain comprising the amino acid sequence of SEQ ID NO: 7 or a variable light chain region sequence having up to 2 amino acid substitutions compared to SEQ ID NO: 7 and a variable heavy chain comprising the amino acid sequence of SEQ ID NO: 16 or a variable heavy chain region sequence having up to 2 amino acid substitutions compared to SEQ ID NO: 16;
   g) a variable light chain comprising the amino acid sequence of SEQ ID NO: 23 or a variable light chain region sequence having up to 2 amino acid substitutions compared to SEQ ID NO: 23 and a variable heavy chain comprising the amino acid sequence of SEQ ID NO: 27 or a variable heavy chain region sequence having up to 2 amino acid substitutions compared to SEQ ID NO: 27; or
   h) a variable light chain comprising the amino acid sequence of SEQ ID NO: 23 or a variable light chain region sequence having up to 2 amino acid substitutions compared to SEQ ID NO: 23 and a variable heavy chain comprising the amino acid sequence of SEQ ID NO: 28 or a variable heavy chain region sequence having up to 2 amino acid substitutions compared to SEQ ID NO: 8.

15. The method of any preceding clause, wherein the anti-CD38 antibody or antigen binding fragment thereof comprises:
   a) a variable light chain comprising the amino acid sequence of SEQ ID NO: 7 and a variable heavy chain comprising the amino acid sequence of SEQ ID NO: 8;
   b) a variable light chain comprising the amino acid sequence of SEQ ID NO: 23 and a variable heavy chain comprising the amino acid sequence of SEQ ID NO: 24;
   c) a variable light chain comprising the amino acid sequence of SEQ ID NO: 7 and a variable heavy chain comprising the amino acid sequence of SEQ ID NO: 13;
   d) a variable light chain comprising the amino acid sequence of SEQ ID NO: 7 and a variable heavy chain comprising the amino acid sequence of SEQ ID NO: 14;
   e) a variable light chain comprising the amino acid sequence of SEQ ID NO: 7 and a variable heavy chain comprising the amino acid sequence of SEQ ID NO: 15;
   f) a variable light chain comprising the amino acid sequence of SEQ ID NO: 7 and a variable heavy chain comprising the amino acid sequence of SEQ ID NO: 16;
   g) a variable light chain comprising the amino acid sequence of SEQ ID NO: 23 and a variable heavy chain comprising the amino acid sequence of SEQ ID NO: 27; or
   h) a variable light chain comprising the amino acid sequence of SEQ ID NO: 23 and a variable heavy chain comprising the amino acid sequence of SEQ ID NO: 28.

16. The method of any preceding clause, wherein the anti-CD38 antibody or antigen binding fragment thereof is a monoclonal antibody, a domain antibody, a single chain antibody, a Fab fragment, a F(ab')2 fragment, a single chain variable fragment (scFv), a scFv-Fc fragment, a single chain antibody (scAb), an aptamer, or a nanobody.

17. The method of any preceding clause, wherein the anti-CD38 antibody or antigen binding fragment thereof is a rabbit, mouse, chimeric, humanized or fully human antigen-binding antibody.

18. The method of any preceding clause, wherein the anti-CD38 antibody or antigen binding fragment thereof is an IgG antibody.

19. The method of any preceding clause, wherein the anti-CD38 antibody or antigen binding fragment thereof is selected from the group consisting of IgG1, IgG2, IgG3, and IgG4 isotype antibodies.

20. The method of any preceding clause, wherein the anti-CD38 antibody or antigen binding fragment thereof is an IgG1 antibody.

21. The method of any preceding clause, wherein the anti-CD38 antibody or antigen binding fragment thereof is comprised in a bispecific antibody, a multispecific antibody, or an immunoconjugate further comprising a therapeutic or diagnostic agent.

22. The method of any preceding clause, wherein the anti-CD38 antibody or antigen binding fragment thereof binds the extracellular domain of human CD38.
23. The method of any preceding clause, wherein the patient blood sample is selected from the group consisting of a whole blood sample, a plasma sample and a serum sample.
24. The method of any preceding clause, wherein the patient blood sample is a whole blood sample, and the method comprises a step of removing the patient red blood cells from the patient blood sample.
25. The method of any preceding clause, wherein the antibodies are alloantibodies
26. The method of any preceding clause, wherein the patient antibodies specifically bind to red blood cell antigens other than any red blood cell antigens expressed by the patient's red blood cells.
27. The method of any preceding clause, wherein the patient antibodies are clinically significant patient antibodies.
28. The method of any preceding clause, wherein the presence of patient antibodies that specifically bind to one or more red blood cell antigens present on the one or more red blood cells from the donor blood sample is indicated by agglutination or haemolysis.
29. The method of any preceding clause, wherein the presence of patient antibodies that specifically bind to one or more red blood cell antigens present on the one or more red blood cells from the donor blood sample indicates the donor blood sample is incompatible with the patient.
30. The method of any preceding clause, wherein the absence of patient antibodies that specifically bind to one or more red blood cell antigens present on the one or more red blood cells from the donor blood sample indicates the donor blood sample is compatible with the patient.
31. The method of any preceding clause, wherein the patient antibodies are IgG antibodies and/or IgM antibodies.
32. The method of any preceding clause, wherein the patient is a human.
33. The method of any preceding clause, wherein the patient has or is suffering from cancer, or where the patient is undergoing treatment for cancer.
34. The method of 33, wherein the cancer is a solid tumour which expresses CD38 on the cell surface.
35. The method of 33, wherein the cancer is a haematological malignancy which expresses CD38 on the cell surface.
36. The method of any one of clauses 33-35, wherein the cancer is a T or B cell non-Hodgkin's lymphoma, chronic lymphocytic leukemia, plasmacytoma, or multiple myeloma.
37. The method of any preceding clause, wherein the one or more red blood cell antigens expressed on the surface of the donor red blood cells are selected from the group consisting of Ab, ABO, Cromer, Diego, Duffy, Gerbich, GLOB, Indian, Kell, Kidd, Knops, Lewis, Lutheran, LW, MNS, P1, Rh, XK, Xg, and Yt.
38. The method of any preceding clause, wherein the one or more red blood cell antigens expressed on the surface of the donor red blood cells are selected from the group consisting of Ab, Rh, MNS, P1, Lewis, Kell, Duffy, KIDD, Lutheran and Xg.
39. The method of any preceding clause, further comprising a step of administering the anti-CD38 antibody or antigen binding fragment thereof to the patient prior to step (a).
40. The method of any preceding clause, wherein the patient has been administered the anti-CD38 antibody or antigen binding fragment thereof less than 1 year, less than 6 months, less than 3 months, less than 2 months, less than 1 month, less than 4 weeks, less than 3 weeks, less than 2 weeks or less than 1 week prior to the sample being obtained from the patient.
41. The method of any preceding clause, wherein the screening of step (b) is performed using an assay selected from the group consisting of a column agglutination assay, an indirect antiglobulin test (IAT) tube assay, and a solid phase assay.
42. The method of any preceding clause, further comprising, prior to the screening of step (c), contacting the patient blood sample with the donor red blood cells from the donor blood sample to provide a patient blood/donor red blood cell mixture.
43. The method of clause 42, further comprising a step of incubating the patient blood/donor red blood cell mixture to enable any one or more patient antibodies in the patient blood sample, if present, to bind to one or more red blood cell antigens present on the donor red blood cells, to form one or more patient antibody/donor red blood cell antigen complexes.
44. The method of clause 42 or 43, further comprising a step of separating, if present, the any one or more patient antibody/donor red blood cell antigen complexes from the patient blood/donor red blood cell mixture, optionally wherein the separating step comprises centrifugation.
45. The method of any one of clauses 42 to 44, further comprising centrifuging the patient blood/donor red blood cell mixture.
46. The method of any preceding clause, comprising:
    a) providing a blood sample from a patient;
    b) providing a blood sample from a donor, wherein the donor blood sample comprises donor red blood cells;
    c) contacting the patient blood sample with one or more donor red blood cells from the donor blood sample to provide a patient blood/donor red blood cell mixture;
    d) incubating the patient blood/donor red blood cell mixture to enable any one or more patient antibodies in the patient blood sample, if present, to bind to one or more red blood cell antigens present on the one or more donor red blood cells, to form one or more patient antibody/donor red blood cell antigen complexes;
    e) optionally separating, if present, the any one or more patient alloantibody/donor red blood cell antigen complexes from the patient blood/donor red blood cell mixture, optionally wherein the separating step comprises centrifugation; and
    f) determining the presence or absence of patient antibodies in the patient blood sample that specifically bind to one or more red blood cell antigens expressed on the one or more donor red blood cells.
47. The method of clause 46, further comprising centrifuging the patient blood/donor red blood cell mixture.
48. The method of any preceding clause, further comprising a step of adding an agglutination agent that specifically binds together any antibodies present in the patient blood sample.

49. The method of clause 48, wherein the agglutination agent that specifically binds together one or more patient antibodies in the patient blood sample is an anti-human globulin reagent.
50. The method of any preceding clause, further comprising generating a report, wherein the report indicates the presence or absence of patient antibodies in the patient blood sample and/or the suitability of the donor to provide a blood or red blood cell donation to the patient.
51. The method of any preceding clause, further comprising a step of screening the patient blood sample against a red blood cell panel prior to step (b) to determine the presence or absence of any patient antibodies in the patient blood sample that specifically bind to any red blood cell antigens present on the surface of any red blood cells in the red blood cell panel.
52. The method of clause 51, wherein the donor red blood cells in the donor blood sample do not express any red blood cell antigens capable of being specifically bound by any of the patient antibodies identified as specifically binding to any red blood cell antigens expressed on the surface of any red blood cells in the red blood cell panel.
53. A method of treating a cancer in a patient, the method comprising providing a blood sample from the patient, and screening the blood sample according to the method of any of clauses 1 to 52.
54. The method of clause 53, wherein the patient has been administered an anti-CD38 antibody or antigen binding fragment thereof.
55. The method of clause 53 or clause 54, wherein the method comprises a step of obtaining the sample from the patient.
56. The method of clause 53, wherein the method comprises:
    a) administering to the patient an anti-CD38 antibody or antigen binding fragment thereof;
    b) obtaining a blood sample from the patient after administration of the anti-CD38 antibody or antigen binding fragment thereof; and
    c) screening the patient blood sample according to the method of any one of clauses 1 to 52.
57. The method of any one of clauses 53 to 56, wherein the cancer is a solid tumour which expresses CD38 on the cell surface.
58. The method of any one of clauses 53 to 56, wherein the cancer is a haematological malignancy which expresses CD38 on the cell surface.
59. The method of any one of clauses 53 to 58, wherein the cancer is a T or B cell non-Hodgkin's lymphoma, chronic lymphocytic leukemia, plasmacytoma, or multiple myeloma.
60. The method of any one of clauses 53 to 59, further comprising a step of administering blood or red blood cells from the donor if the donor is found to be compatible with the patient.
61. An anti-CD38 antibody or antigen binding fragment thereof for use in a method of treating a cancer in a patient, the method comprising the method of any one of clauses 53 to 60.

The invention claimed is:

1. A method of screening a blood sample obtained from a patient, wherein the patient has been administered an anti-CD38 antibody or antigen binding fragment thereof, the method comprising:
   a) providing a blood sample from the patient;
   b) providing a blood sample from a donor, wherein the donor blood sample comprises donor red blood cells; and
   c) screening the patient blood sample, comprising determining the presence or absence of one or more patient antibodies in the patient blood sample that specifically bind to one or more red blood cell antigens expressed on the surface of the donor red blood cells,
   wherein the method does not comprise a step of contacting the patient blood sample or the donor blood sample with an agent that inhibits binding of the anti-CD38 antibody or antigen binding fragment thereof to membrane-bound CD38 present on the surface of the one or more donor red blood cells,
   wherein anti-CD38 antibody or antigen binding fragment thereof comprises
   a) an HCDR1 comprising the amino acid sequence SEQ ID NO: 1;
   an HCDR2 comprising the amino acid sequence SEQ ID NO: 2;
   an HCDR3 comprising the amino acid sequence SEQ ID NO: 3;
   an LCDR1 comprising the amino acid sequence SEQ ID NO: 4;
   an LCDR2 comprising the amino acid sequence SEQ ID NO: 5; and
   an LCDR3 comprising an amino acid sequence selected from the group consisting of SEQ ID NOs: 6, 9, 10, 11 and 12; or
   b) an HCDR1 comprising the amino acid sequence of SEQ ID NO: 17;
   an HCDR2 comprising the amino acid sequence of SEQ ID NO: 18;
   an HCDR3 comprising the amino acid sequence of SEQ ID NO: 19;
   an LCDR1 comprising the amino acid sequence of SEQ ID NO: 20;
   an LCDR2 comprising the amino acid sequence of SEQ ID NO: 21; and
   an LCDR3 comprising an amino acid sequence selected from the group consisting of SEQ ID NO: 22, 25 and 26.

2. The method of claim 1 wherein the agent that inhibits binding of the anti-CD38 antibody or antigen binding fragment thereof to membrane-bound CD38 present on the surface of the one or more donor red blood cells is a soluble CD38 antigen, an anti-CD38 idiotype antibody, or an antigen-stripping agent.

3. The method of claim 2 wherein the antigen-stripping agent is a redox reagent, optionally DTT, or an enzyme, optionally a protease.

4. The method of claim 3 wherein the protease is selected from the group consisting of trypsin, alpha chymotrypsin, papain, and ficin.

5. The method of claim 1, wherein the anti-CD38 antibody or antigen binding fragment thereof comprises:
   a) a variable light chain comprising the amino acid sequence of SEQ ID NO: 7 and a variable heavy chain comprising the amino acid sequence of SEQ ID NO: 8; or
   b) a variable light chain comprising the amino acid sequence of SEQ ID NO: 23 and a variable heavy chain comprising the amino acid sequence of SEQ ID NO: 24; or
   c) a variable light chain comprising the amino acid sequence of SEQ ID NO: 7 and a variable heavy chain comprising the amino acid sequence of SEQ ID NO: 13; or d) a variable light chain comprising the amino acid sequence of SEQ ID NO: 7 and a variable heavy chain comprising the amino acid sequence of SEQ ID NO: 14; or e) a variable light chain comprising the amino acid sequence of SEQ ID NO: 7 and a variable heavy chain comprising the amino acid sequence of SEQ ID NO: 15; or f) a variable light chain comprising the amino acid sequence of SEQ ID NO: 7 and a variable heavy chain comprising the amino acid sequence of SEQ ID NO: 16; or g) a variable light chain comprising the amino acid sequence of SEQ ID NO: 23 and a variable heavy chain comprising the amino acid sequence of SEQ ID NO: 27; or h) a variable light chain comprising the amino acid sequence of SEQ ID NO: 23 and a variable heavy chain comprising the amino acid sequence of SEQ ID NO: 28.

6. The method of claim 1, wherein the anti-CD38 antibody or antigen binding fragment thereof is a monoclonal antibody, a domain antibody, a single chain antibody, a Fab fragment, a F (ab')2 fragment, a single chain variable fragment (scFv), a scFv-Fc fragment, a single chain antibody (scAb), an aptamer, or a nanobody.

7. The method of claim 1, wherein the anti-CD38 antibody or antigen binding fragment thereof is an IgG antibody, optionally an IgG1 antibody.

8. The method of claim 1, wherein the patient antibodies are alloantibodies, and/or wherein the patient antibodies specifically bind to red blood cell antigens other than any red blood cell antigens expressed by the patient's red blood cells, and/or wherein the patient antibodies are clinically significant patient antibodies, and/or wherein the patient antibodies are IgG antibodies and/or IgM antibodies.

9. The method of claim 1, wherein the patient has or is suffering from cancer, or where the patient is undergoing treatment for cancer.

10. The method of claim 9, wherein the cancer is a solid tumour which expresses CD38 on the cell surface or wherein the cancer is a haematological malignancy which expresses CD38 on the cell surface.

11. The method of claim 9, wherein the cancer is a T or B cell non-Hodgkin's lymphoma, chronic lymphocytic leukemia, plasmacytoma, or multiple myeloma.

12. The method of claim 1, wherein the one or more red blood cell antigens expressed on the surface of the donor red blood cells are selected from the group consisting of Ab, ABO, Cromer, Diego, Duffy, Gerbich, GLOB, Indian, Kell, Kidd, Knops, Lewis, Lutheran, LW, MNS, P1, Rh, XK, Xg, and Yt.

13. The method of claim 1, wherein the one or more red blood cell antigens expressed on the surface of the donor red blood cells are selected from the group consisting of Ab, Rh, MNS, P1, Lewis, Kell, Duffy, KIDD, Lutheran and Xg.

14. The method of claim 1, wherein the patient has been administered the anti-CD38 antibody or antigen binding fragment thereof less than 1 year prior to the sample being obtained from the patient.

15. The method of claim 1, comprising:
a) providing a blood sample obtained from a patient;
b) providing a blood sample obtained from a donor, wherein the donor blood sample comprises donor red blood cells;

c) contacting the patient blood sample with one or more donor red blood cells from the donor blood sample to provide a patient blood/donor red blood cell mixture;

d) incubating the patient blood/donor red blood cell mixture to enable any one or more patient antibodies in the patient blood sample, if present, to bind to one or more red blood cell antigens present on the one or more donor red blood cells, to form one or more patient antibody/donor red blood cell antigen complexes;

e) optionally separating, if present, the any one or more patient alloantibody/donor red blood cell antigen complexes from the patient blood/donor red blood cell mixture, optionally wherein the separating step comprises centrifugation; and f) determining the presence or absence of patient antibodies in the patient blood sample that specifically bind to one or more red blood cell antigens expressed on the one or more donor red blood cells;

optionally further comprising centrifuging the patient blood/donor red blood cell mixture.

16. The method of claim 1, further comprising a step of adding an agglutination agent that specifically binds together any antibodies present in the patient blood sample.

17. The method of claim 16 wherein the agglutination agent that specifically binds together one or more patient antibodies in the patient blood sample is an anti-human globulin reagent.

18. The method of claim 1, further comprising a step of screening the patient blood sample against a red blood cell panel prior to step (b) to determine the presence or absence of any patient antibodies in the patient blood sample that specifically bind to any red blood cell antigens present on the surface of any red blood cells in the red blood cell panel; optionally wherein the donor red blood cells in the donor blood sample do not express any red blood cell antigens capable of being specifically bound by any of the patient antibodies identified as specifically binding to any red blood cell antigens expressed on the surface of any red blood cells in the red blood cell panel.

19. A method of treating a cancer in a patient, the method comprising providing a blood sample from the patient, and screening the blood sample according to the method of claim 1.

20. The method of claim 19, wherein the patient has been administered an anti-CD38 antibody or antigen binding fragment thereof.

21. The method of claim 20, wherein the method comprises:
a) administering to the patient the anti-CD38 antibody or antigen binding fragment thereof;
b) obtaining a blood sample from the patient after administration of the anti-CD38 antibody or antigen binding fragment thereof; and
c) screening the patient blood sample according to the method of claim 1.

22. The method of claim 19, wherein the cancer is a solid tumour which expresses CD38 on the cell surface.

23. The method of claim 19, wherein the cancer is a haematological malignancy which expresses CD38 on the cell surface.

24. The method of claim 19, wherein the cancer is a T or B cell non-Hodgkin's lymphoma, chronic lymphocytic leukemia, plasmacytoma, or multiple myeloma.

25. The method of claim 19, further comprising a step of administering blood or red blood cells from the donor if the donor is found to be compatible with the patient.

26. The method of claim 1, wherein the anti-CD38 antibody or antigen binding fragment thereof comprises a variable light chain comprising the amino acid sequence of SEQ ID NO: 7 and a variable heavy chain comprising the amino acid sequence of SEQ ID NO: 8.

* * * * *